(12) United States Patent
Aravena et al.

(10) Patent No.: US 7,588,559 B2
(45) Date of Patent: Sep. 15, 2009

(54) INJECTION SYSTEMS

(75) Inventors: Ines M. Aravena, Camarillo, CA (US);
Ajay Kumar, Palmdale, CA (US);
Hamid Abedi, Newport Coast, CA (US)

(73) Assignee: W&H Dentalwerk Bürmoos GmbH, Bürmoos (AT)

( * ) Notice: Subject to any disclaimer, the term of this patent is extended or adjusted under 35 U.S.C. 154(b) by 368 days.

(21) Appl. No.: 11/089,446

(22) Filed: Mar. 24, 2005

(65) Prior Publication Data
US 2006/0106363 A1 May 18, 2006

Related U.S. Application Data

(60) Provisional application No. 60/584,260, filed on Jul. 1, 2004, provisional application No. 60/584,321, filed on Jul. 1, 2004, provisional application No. 60/645,210, filed on Jan. 19, 2005.

(51) Int. Cl.
*A61M 5/00* (2006.01)
*A61M 31/00* (2006.01)
*A61B 17/20* (2006.01)

(52) U.S. Cl. .................. 604/188; 604/22; 604/506; 604/207

(58) Field of Classification Search .................. 604/19, 604/22, 48, 500, 506, 181, 187, 188, 200, 604/201, 205–208, 211, 272; 606/92, 93; 222/386, 389–391
See application file for complete search history.

(56) References Cited

U.S. PATENT DOCUMENTS

| | | | |
|---|---|---|---|
| 2,773,500 A | 12/1956 | Young | |
| 4,381,777 A | 5/1983 | Garnier | |
| 4,787,893 A * | 11/1988 | Villette | ........... 604/188 |
| 4,944,677 A | 7/1990 | Alexandre | |
| 5,057,013 A | 10/1991 | Dillon | |
| 5,173,050 A | 12/1992 | Dillon | |
| 5,269,762 A | 12/1993 | Armbruster et al. | |
| 5,456,670 A | 10/1995 | Neer et al. | |

(Continued)

FOREIGN PATENT DOCUMENTS

FR 2540385 A1 8/1994

(Continued)

OTHER PUBLICATIONS

Nov. 22, 2005 "PCT Invitation to Pay Additional Fees," which includes an "Annex to Form PCT/ISA/206- Communication Relating to the Results of the Partial International Search," from the International Searching Authority (EPO/ISA), 6 pages total.

(Continued)

*Primary Examiner*—Kevin C Sirmons
*Assistant Examiner*—Bhisma Mehta
(74) *Attorney, Agent, or Firm*—Klarquist Sparkman, LLP

(57) ABSTRACT

An intraosseous injection device includes a tool having a distal portion, a proximal portion, and a solution dispensing opening. The distal portion has one or more cutting surfaces. The tool can be coupled with a protective carrier. The tool can be rotatably coupled to a tool actuation mechanism. A housing has a distal end and a proximal end. The housing releasably receives a solution cartridge containing a solution. A solution dispensing mechanism dispenses solution from the solution cartridge. A gripping member grips a proximal portion of the tool. A rotation device rotates the gripping member and thereby rotates the tool about an axis. The proximal portion of the tool connects directly to the solution cartridge such that solution from the cartridge can be delivered through the solution dispensing opening. The tool is configured to rotate relative to the solution cartridge.

57 Claims, 98 Drawing Sheets

U.S. PATENT DOCUMENTS

| | | | |
|---|---|---|---|
| 5,554,154 A | 9/1996 | Rosenberg | |
| 5,672,155 A | 9/1997 | Riley et al. | |
| 5,690,618 A | 11/1997 | Smith et al. | |
| 5,762,639 A | 6/1998 | Gibbs | |
| 5,779,708 A | 7/1998 | Wu | |
| 5,807,334 A | 9/1998 | Hodosh et al. | |
| 5,927,976 A * | 7/1999 | Wu | 433/82 |
| 6,159,161 A | 12/2000 | Hodosh | |
| 6,183,442 B1 | 2/2001 | Athanasiou et al. | |
| 6,217,561 B1 | 4/2001 | Gibbs | |
| 6,245,043 B1 | 6/2001 | Villette | |
| 6,247,928 B1 | 6/2001 | Meller et al. | |
| 6,273,715 B1 | 8/2001 | Meller et al. | |
| 6,287,114 B1 | 9/2001 | Meller et al. | |
| 6,468,248 B1 | 10/2002 | Gibbs | |
| 6,520,928 B1 | 2/2003 | Junior | |
| 6,547,561 B2 | 4/2003 | Meller et al. | |
| 6,575,745 B2 | 6/2003 | Meller et al. | |
| 6,582,405 B2 | 6/2003 | Kawagishi et al. | |
| 6,626,887 B1 | 9/2003 | Wu | |
| 6,695,782 B2 * | 2/2004 | Ranucci et al. | 600/439 |
| 2003/0032939 A1 | 2/2003 | Gibbs | |
| 2003/0114858 A1 | 6/2003 | Athanasiou et al. | |
| 2003/0225344 A1 | 12/2003 | Miller | |
| 2003/0225411 A1 | 12/2003 | Miller | |
| 2004/0073168 A1 | 4/2004 | Takatsuka et al. | |
| 2004/0092882 A1 | 5/2004 | Wu | |
| 2005/0065473 A1 | 3/2005 | Martin | |
| 2006/0036212 A1 * | 2/2006 | Miller | 604/48 |

FOREIGN PATENT DOCUMENTS

WO   WO 98/53757   12/1998

OTHER PUBLICATIONS

Jun. 15, 2006 "PCT Notification Concerning Transmittal of International Application as Published or Republished," which includes copy of WO 2006/007590 A3 with International Search Report, 7 pages total.

* cited by examiner

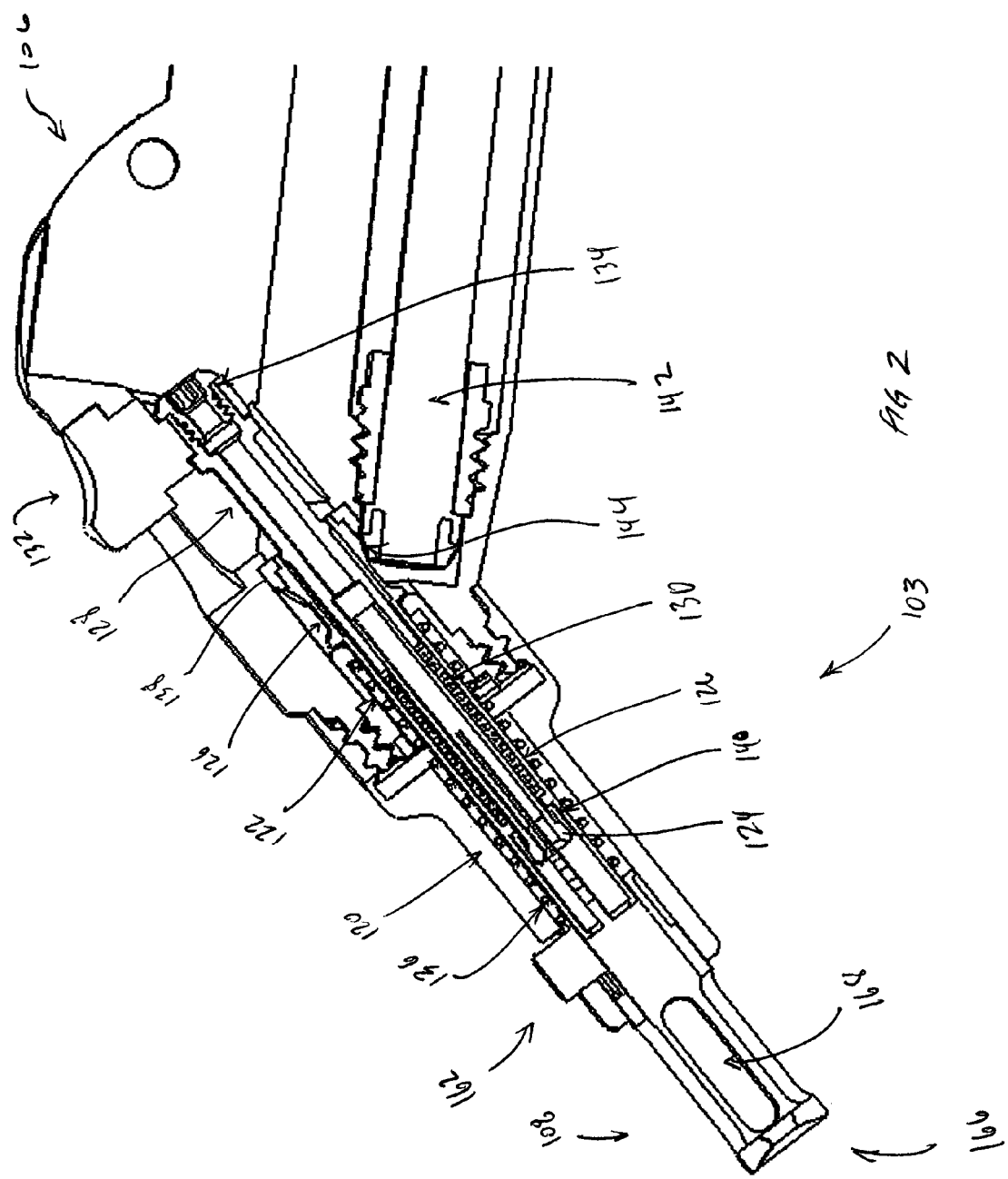

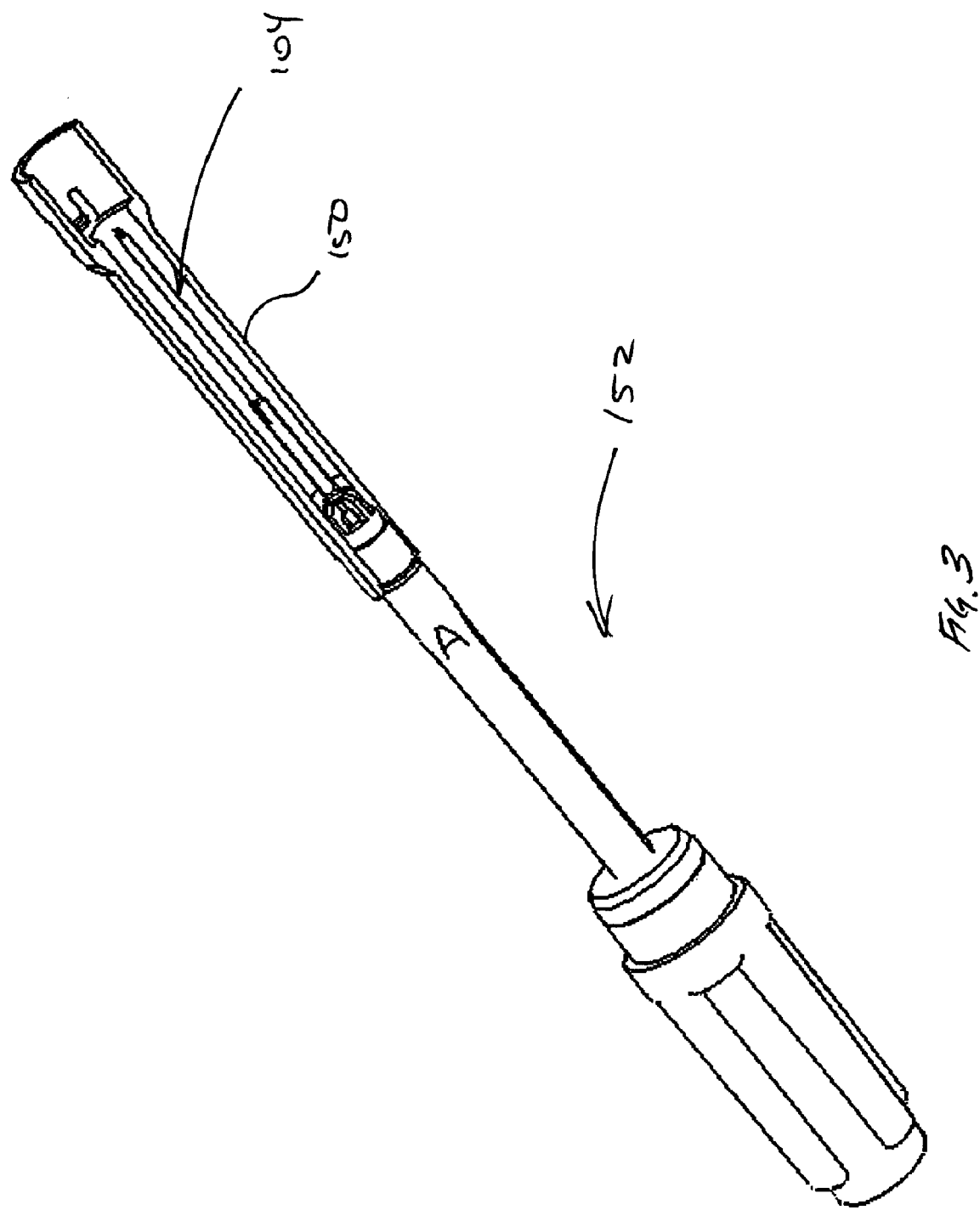

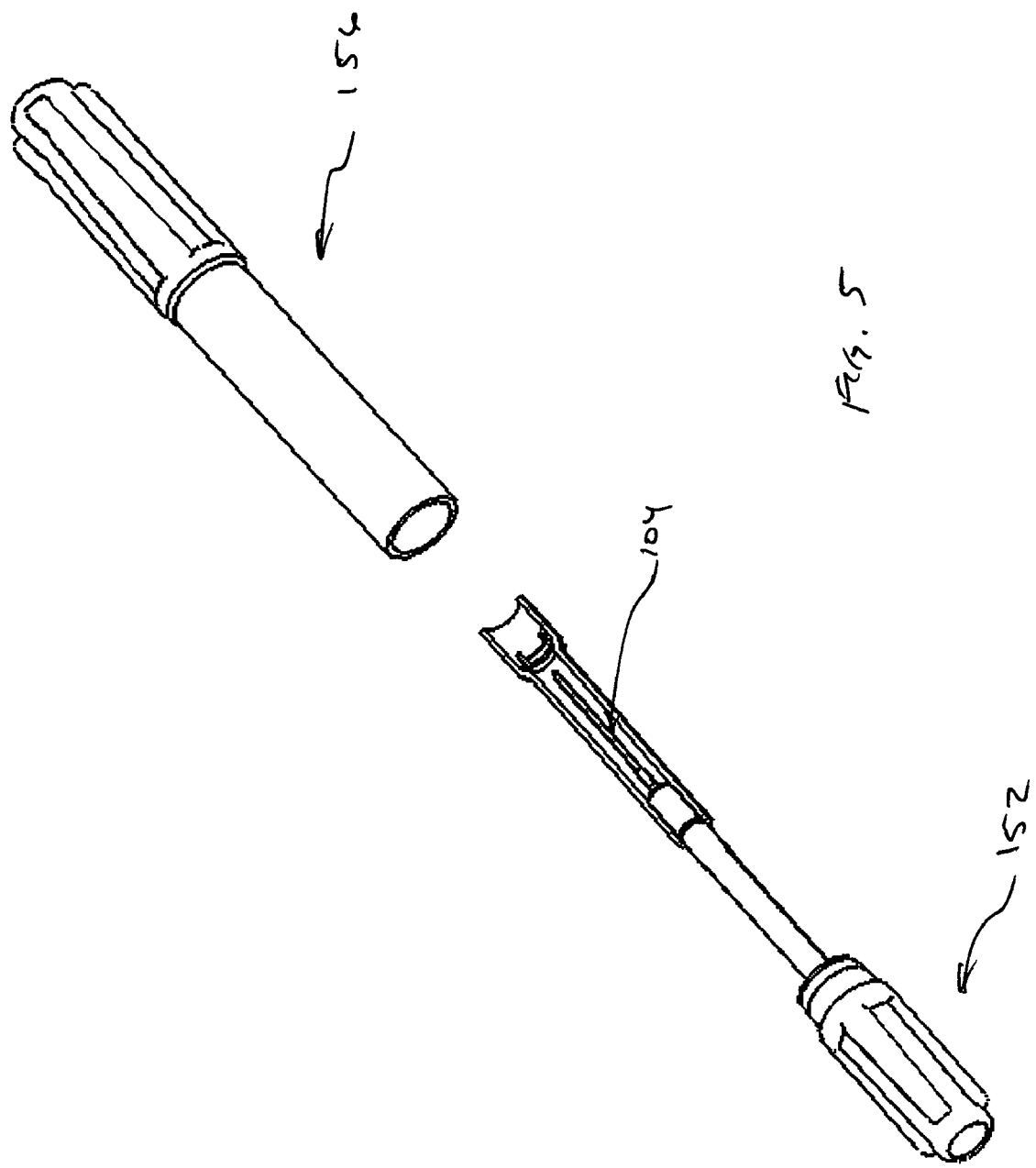

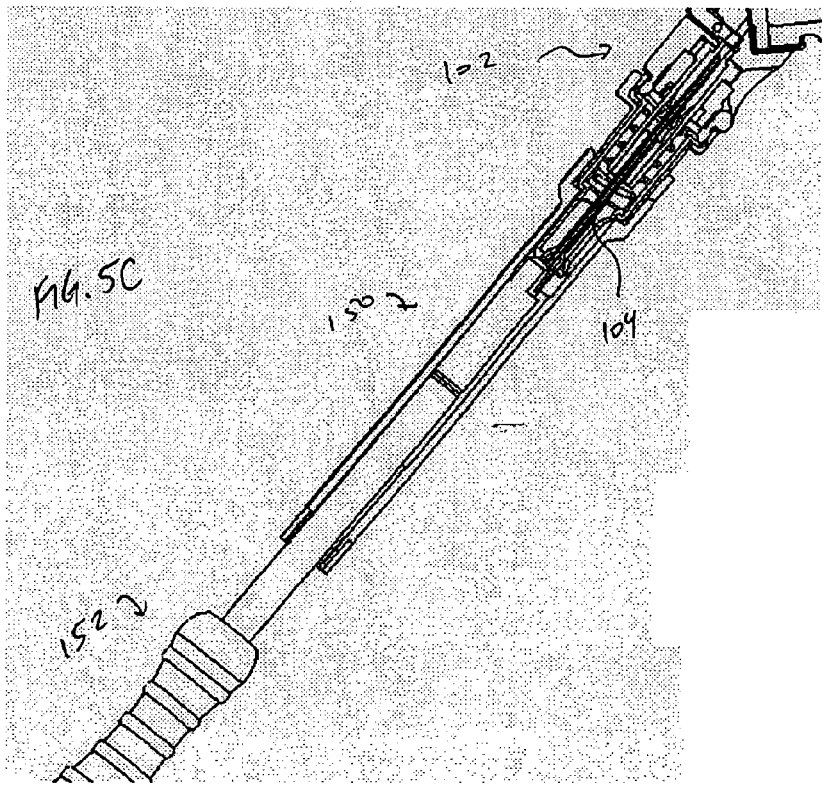
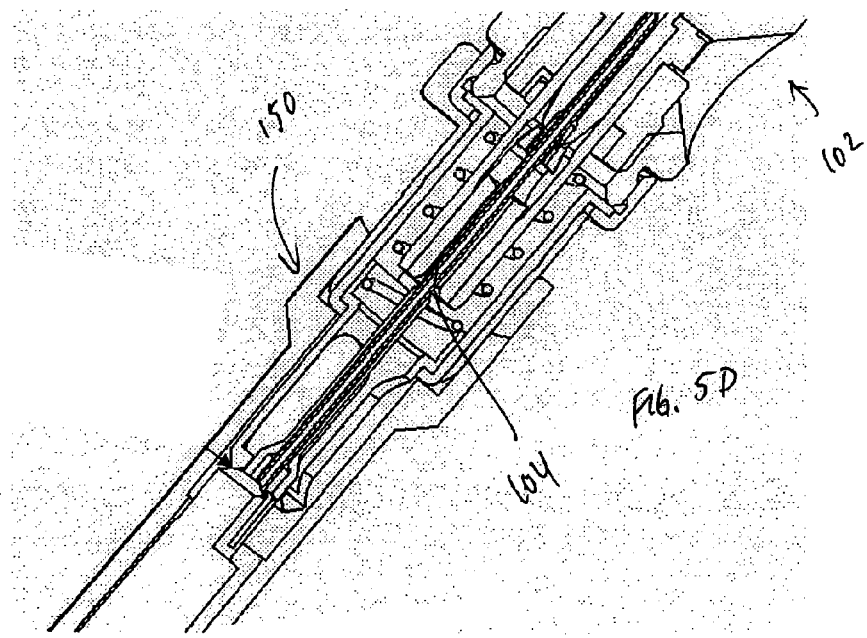

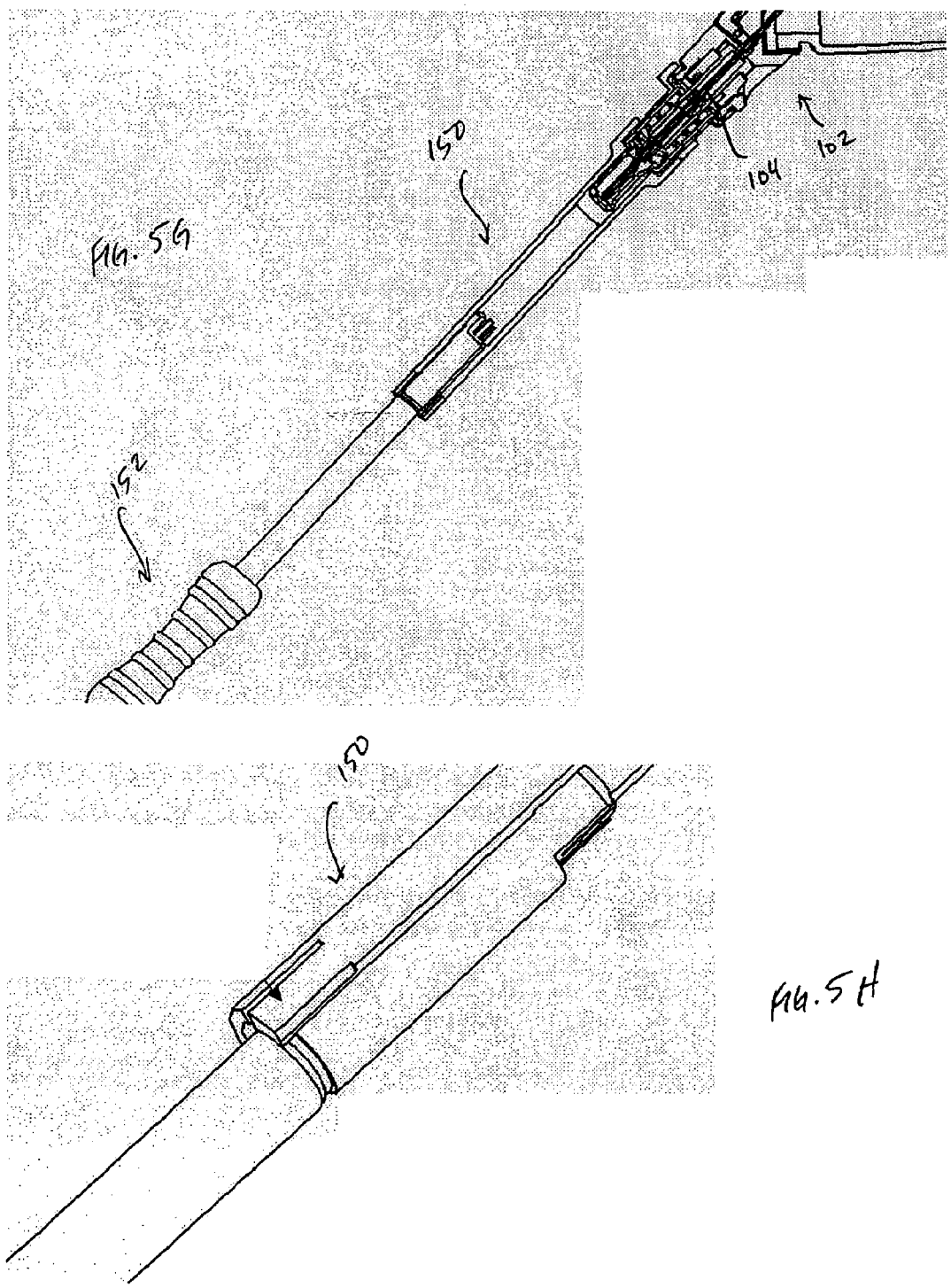

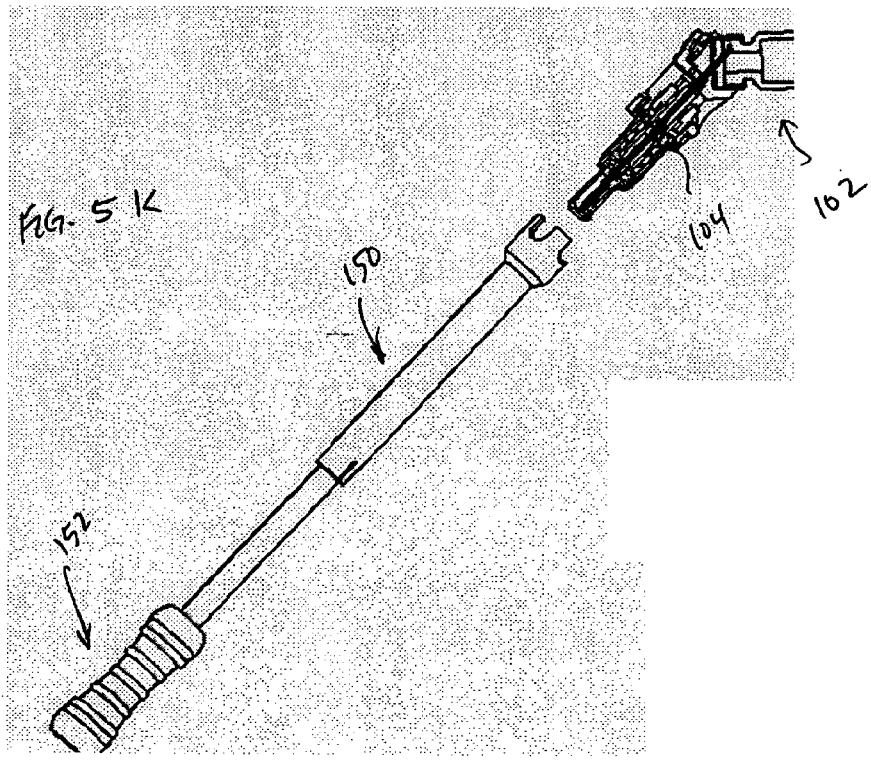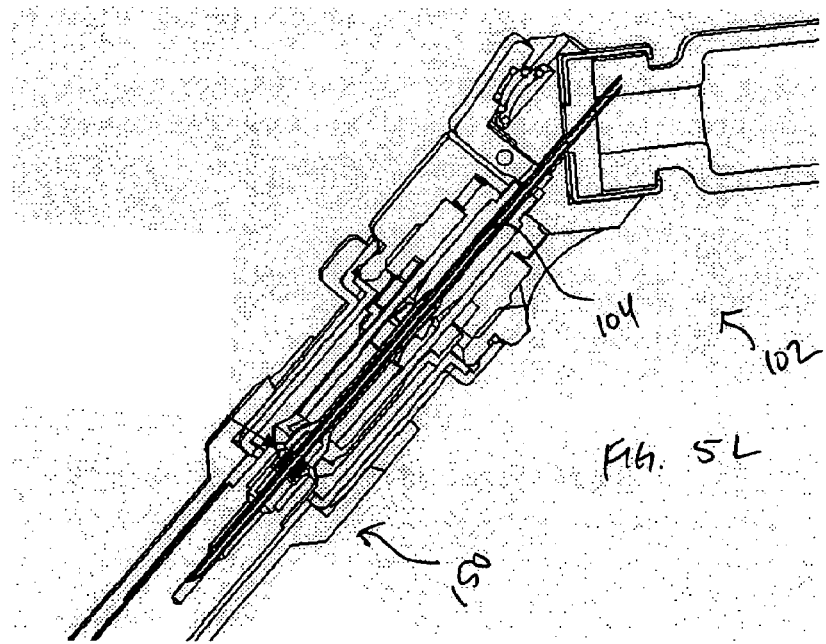

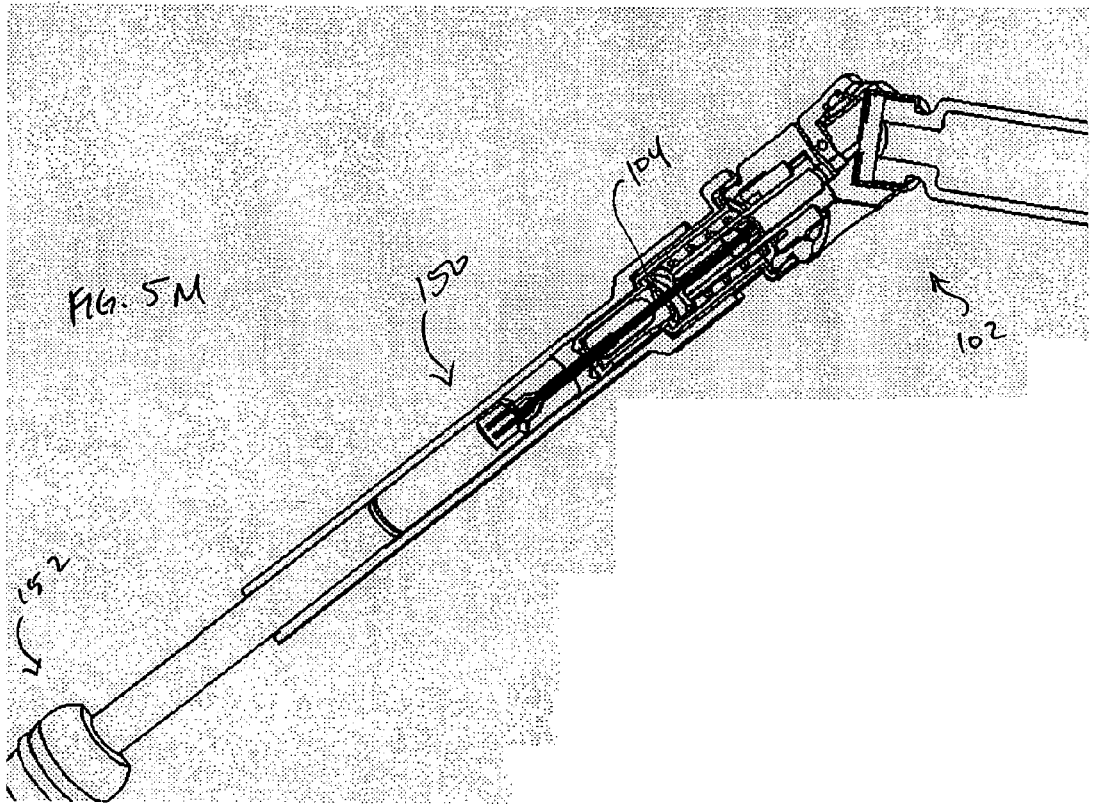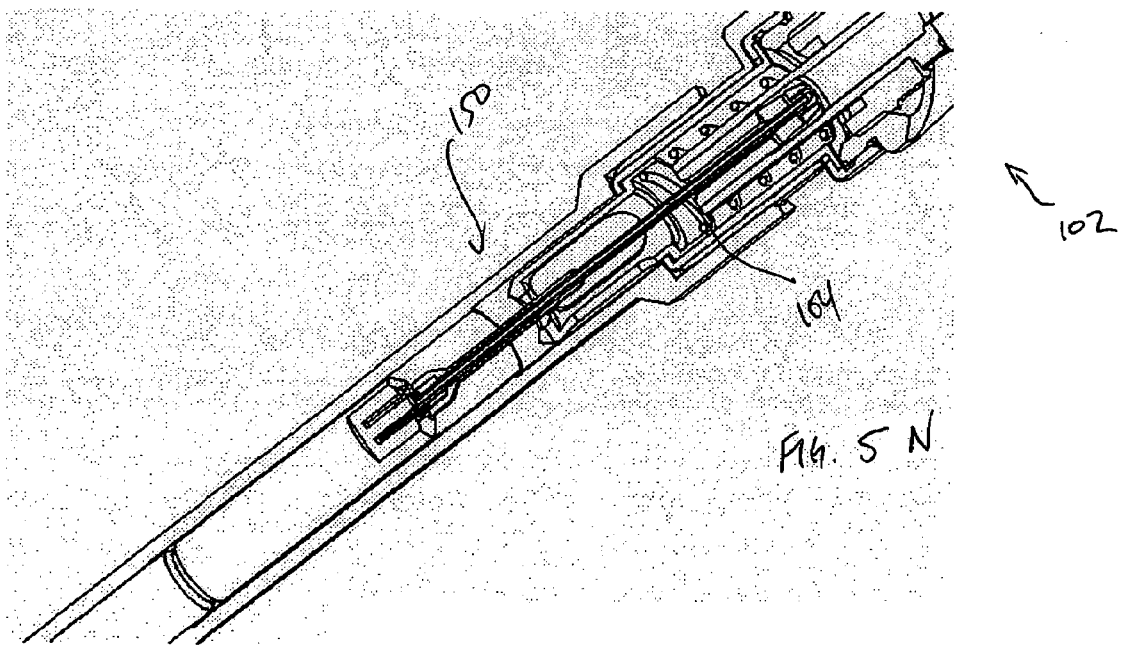

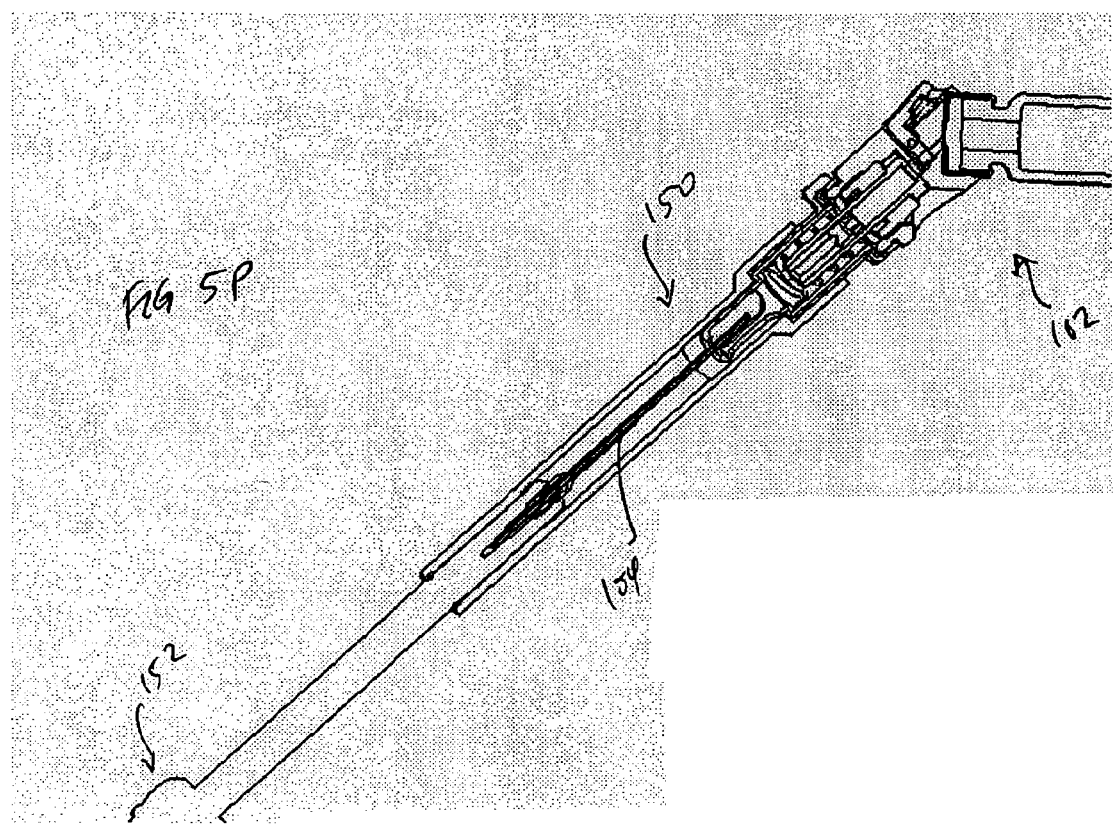

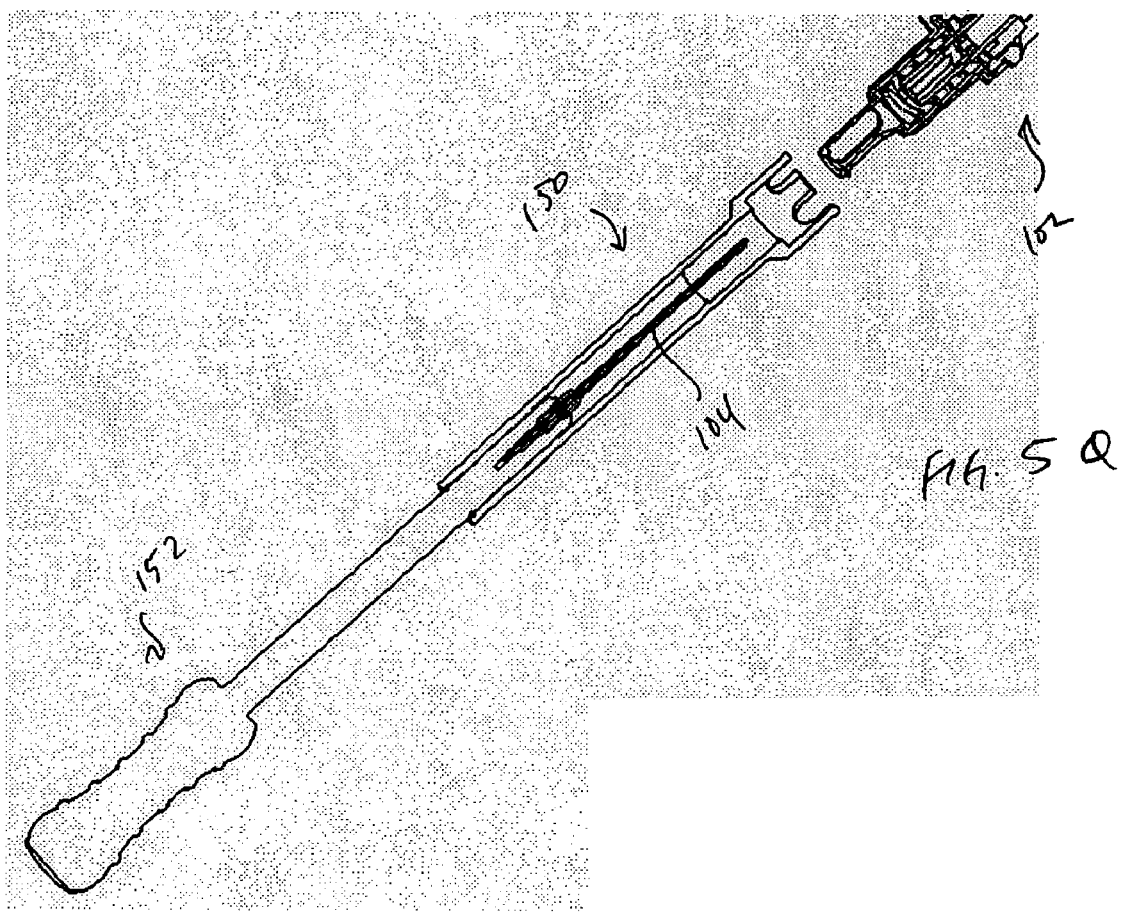

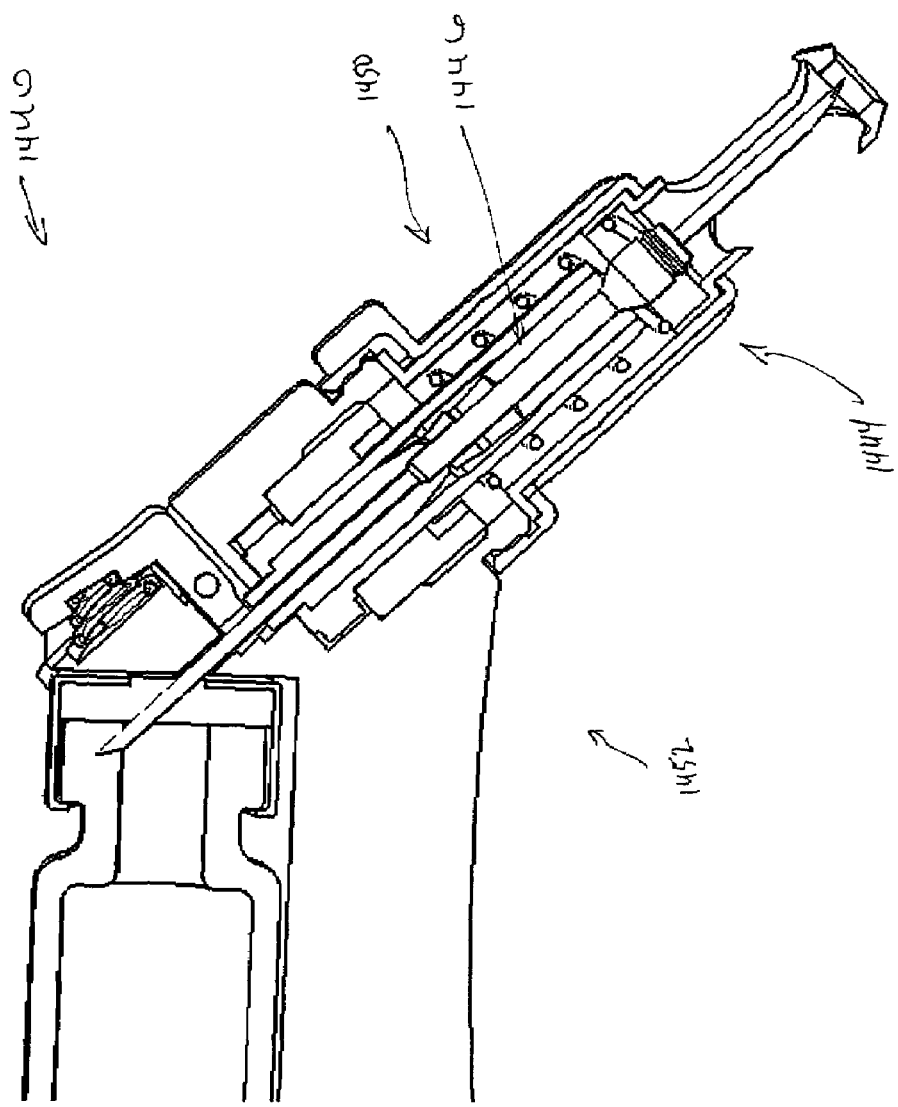

INJECTION SYSTEMS

PRIORITY INFORMATION

This application is based on and claims priority to U.S. Provisional Patent Applications No. 60/584,260 (filed Jul. 1, 2004), 60/584,321 (filed Jul. 1, 2004), and 60/645,210 (filed Jan. 19, 2005), the entire contents of each of which are hereby expressly incorporated by reference herein and made a part of this specification.

BACKGROUND OF THE INVENTION

1. Field of the Invention

This application relates to medical instruments generally, and in particular relates to injection systems for intraosseous and or dental injection of medical solution.

2. Description of the Related Art

Intraosseous injection of anesthetic is a commonly used technique to provide a small amount of anesthetic solution to a localized area, such as the jawbone of a patient for a dental or endodontic procedure. In some cases, anesthetic solution is delivered in the trabecular bone rather than delivering the anesthesia to the soft tissue of the patient. Using an intraosseous injection system can result in profound anesthesia in less than thirty seconds, while delivery of anesthetic solution to the soft tissue can take more than seven minutes for the anesthetic to take effect.

Intraosseous injection requires the perforation of the cortical plate, which is very hard. Some intraosseous injection systems have disadvantages in the perforation or injection process. Some systems require the use of at least two tools, a perforator and a separate injector needle, making the injection procedure complicated and time consuming. With some systems, it is difficult to find the initial hole created by the perforator to inject the anesthetic. In some cases where a guide sleeve is used, the guide sleeve can be difficult to remove. Some systems have a needle that serves both as a perforator and an injector, however, these systems often become clogged with bone chips which can prevent the injection of the anesthetic solution.

Some endodontic techniques require tool rotation to penetrate the site. A needle, a perforator, a file, or another endodontic tool can be connected to an intermediate component to engage a driving device. In some systems, the tools tend to heat up during cortical plate penetration and can wear-out prematurely. Excessive heat generated during cortical plate penetration can cause the intermediate component holding the needle or perforator to meltdown and in some cases detach from the needle or perforator. The detached needle or perforator can lead to further complications. In some cases, driving devices having motorized portions can break the tools by applying excessive torque to the tool.

Some intraosseous injection systems require an intermediate piece to transfer anesthetic from an ampoule to the needle. Some intraosseous injection systems have a static needle arrangement where it is difficult and/or time consuming to replace the needle and may increase the risk of needle-prick injuries. For example, some syringe connections have threaded features that require turning a hub several times for attaching or removing a needle from the system.

Additionally, safety concerns generally call for capping the needle for transport to or from the point of use. Some needle receptacles have covering mechanisms, such as shields, that require the end user to push them down to cover the needle after the needle is used. However, in some systems, the needle is not shielded at all times and the chances of injury still exist. For example, the end user is less protected after the cap or other covering mechanism is removed or withdrawn. Exposure of the needle increases the chances of pricking the patient and/or the end user.

SUMMARY OF THE INVENTION

Accordingly, there is a need in the art for improved systems and methods for delivery of anesthetic. In some embodiments, a single needle can perforate bone without over heating and/or clogging to allow for direct delivery of anesthetic solution. In some embodiments, a handpiece mechanism reduces the chances of dislodging the tool, avoids over torque of the tool, permits direct insertion of the tool into the ampoule, and offers quick connections between the tool and the handpiece to reduce the chances of injuries to the patient and end-user, reduce the length of procedures, and reduce overall cost. In some embodiments, the tool is covered by a retractable sleeve to reduce the risk of injuries.

In one embodiment, an injection device comprises a tool having a distal portion, a proximal portion, and a solution dispensing opening. A housing has a distal end and a proximal end. The housing is configured to releasably receive a solution cartridge containing a solution. A solution dispensing mechanism is configured to dispense solution from the solution cartridge. A gripping member is positioned within the distal end of the housing. The gripping member is configured to grip a proximal portion of the tool. A rotation device is configured to rotate the gripping member and thereby rotate the tool about an axis. The device is configured such that the proximal portion of the tool is positioned at least partially within the solution cartridge while the tool is rotated.

In another embodiment, a method of dispensing a solution comprises loading an ampoule of solution into a housing. A tool is placed in a gripping mechanism of the housing until at least a portion of the tool enters the ampoule to place the tool in direct communication with an interior portion of the ampoule. A distal end of the tool is placed into a patient. The tool is rotated. Solution is delivered from the ampoule into the patient through the tool.

In another embodiment, a method of dispensing a solution comprises loading an ampoule of solution into a housing. A tool is placed in a gripping mechanism of the housing until at least a portion of the tool enters the ampoule to place the tool in direct communication with an interior portion of the ampoule. A distal end of the tool is placed into a patient. The ampoule of solution is rotated. Solution is delivered from the ampoule into the patient through the tool.

In another embodiment, an injection tool delivery system for an intraosseous inject device comprises a intraosseous drill bit having a distal portion, a proximal portion, and a solution dispensing opening. A protective carrier comprises a base portion and a cap portion. The base portion includes a gripping member configured to grip the distal portion drill bit. The cap portion comprises a first end configured to be coupled to the base portion and a cavity for receiving the proximal portion of the drill bit when the cap portion is coupled to the base portion.

In another embodiment, an intraosseous injection tool delivery system for an intraosseous inject device comprises a intraosseous drill bit having a distal portion, a proximal portion, and a solution dispensing opening. A protective carrier comprises a base, the base including a gripping member configured to grip the distal portion drill bit.

In another embodiment, a medication injection device comprises a housing for grasping by an operator, the housing having a distal end and a proximal end. A cartridge receiving mechanism is coupled to the housing and configured to releasably receive a solution cartridge containing a solution. The cartridge receiving mechanism is moveable between a cartridge loading position and a solution dispensing position. The cartridge receiving mechanism is positioned further from the housing in the cartridge loading position as compared to the solution dispensing position. A rotatable gripping mechanism is configured to grip a tool having a distal portion, a proximal portion, and a solution dispensing opening. A rotation mechanism is configured to rotate the gripping mechanism about an axis. A solution dispensing mechanism is configured to reduce the volume of the solution cartridge positioned in the cartridge receiving mechanism.

In another embodiment, a medication injection device comprises a housing for grasping by an operator, the housing having a distal end and a proximal end. A cartridge receiving mechanism is coupled to the housing and configured to releasably receive a solution cartridge containing a solution. The cartridge receiving mechanism is moveable between a cartridge loading position and a solution dispensing position. The cartridge receiving mechanism is positioned further from the housing in the cartridge loading position as compared to the solution dispensing position. A gripping mechanism is configured to grip a tool having a distal portion, a proximal portion, and a solution dispensing opening. A solution dispensing mechanism is configured to reduce the volume of the solution cartridge positioned in the cartridge receiving mechanism.

In another embodiment, an injection device comprises a tool having a distal portion, a proximal portion, and a solution dispensing opening. A housing has a distal end and a proximal end. The housing is configured to releasably receive a solution cartridge containing a solution. A solution dispensing mechanism is configured to dispense solution from the solution cartridge. A gripping member is positioned within the distal end of the housing. The gripping member is configured to grip a proximal portion of the tool. A rotation device is configured to rotate the gripping member and thereby rotate the tool about an axis. An adjustable protective sleeve mechanism is configured to cover the distal portion of the tool.

In another embodiment, an injection system comprises a housing having a distal end and a proximal end. The housing is configured to releasably receive a solution cartridge containing a solution. A solution dispensing mechanism is configured to dispense solution from the solution cartridge. A gripping member is positioned within the distal end of the housing. The gripping member comprises a chucking mechanism configured to grip a proximal portion of an intraosseous injection tool. A rotation device is configured to rotate the gripping member and thereby rotate the tool about an axis.

In another embodiment, an injection device comprises a tool having a distal portion, a proximal portion, and a solution dispensing opening. A housing has a distal end and a proximal end. The housing comprises a receiving portion configured to releasably receive a solution cartridge containing a solution. A solution dispensing mechanism is configured to dispense solution from the solution cartridge. A gripping member is positioned within the distal end of the housing. The gripping member is configured to grip the proximal portion of the tool. A rotation device is configured to rotate the gripping member and thereby rotate the tool about an axis. The device is configured such that the proximal portion of the tool is positioned at least partially within the solution cartridge while the tool is rotated and the cartridge receiving section is configured to allow the solution cartridge to rotate as the tool is rotated.

In another embodiment, an injection device comprises a tool having a distal portion, a proximal portion, and a solution dispensing opening. The distal portion of the tool has one or more bevels. A housing has a distal end and a proximal end. The housing is configured to receive a solution cartridge containing a solution. A solution dispensing mechanism is configured to dispense solution from the solution cartridge. A gripping member is positioned within the distal end of the housing. The gripping member is configured to grip a proximal portion of the tool. The device is configured such that the proximal portion of the tool is positioned at least partially within the solution cartridge while the distal portion of the tool contacts the working site.

In another embodiment, a method of coupling a tool with a handpiece comprises providing a housing comprising a gripping mechanism and an ampoule of solution. A tool is provided having a distal portion, a proximal portion, and a solution dispensing opening. The tool is coupled with a protective carrier comprising a base portion and a cap portion. The base portion includes a gripping member configured to grip the distal portion drill bit. The cap portion comprises a first end configured to be coupled to the base portion and a cavity for receiving the proximal portion of the drill bit when the cap portion is coupled to the base portion. The cap portion of the protective carrier is removed to expose a proximal portion of the tool. In some other embodiments, the cap portion is not included. In some other embodiments, an alignment sleeve is included. The base portion of the protective carrier is held by the user. The proximal portion of the tool is inserted through the gripping mechanism of the housing into the ampoule of solution. The tool is gripped with the gripping mechanism of the housing. The base portion of the protective carrier is removed to expose the tool.

In another embodiment, an injection system comprises an injection device. The injection device comprises a housing having a distal end and a proximal end, the housing configured to releasably receive a solution cartridge containing a solution. A solution dispensing mechanism configured to dispense solution from the solution cartridge. A gripping member positioned within the distal end of the housing, the gripping member configured to grip a proximal portion of the tool. A rotation device configured to rotate the gripping member and thereby rotate the tool about an axis. The device is configured such that the proximal portion of the tool is positioned at least partially within the solution cartridge while the tool is rotated. The injection system comprises a tool delivery system comprising a tool having a distal portion, a proximal portion, and a solution dispensing opening. A protective carrier comprises a base portion and a cap portion. The base portion includes a gripping member configured to grip the distal portion drill bit. The cap portion comprises a first end configured to be coupled to the base portion and a cavity for receiving the proximal portion of the drill bit when the cap portion is coupled to the base portion.

In another embodiment, a method of using an intraosseous injection device comprises removing an outer packaging, e.g., a cap portion, of a protective carrier to expose a proximal portion of an intraosseous drill bit. The drill bit comprises a proximal portion and a distal portion. The distal portion is supported within a base portion of the protective carrier. The proximal portion of the drill bit is inserted into the intraosseous injection device while the distal portion of the drill bit remains within the base portion of the carrier. The intraosseous injection device is used to inject a solution into a patient through the drill bit. The distal end of the drill bit is inserted into the base portion of the protective carrier while the proximal end of the drill bit remains in the intraosseous injection device. The proximal portion of the drill bit is removed from the intraosseous injection device.

In another embodiment, a method of using an intraosseous injection device, comprises removing a protective carrier and alignment sleeve from its outer packaging, the alignment sleeve at least partially housing an intraosseous drill bit, the drill bit comprising a proximal portion and a distal portion, the distal portion being supported within a base portion of the protective carrier. The proximal portion of the drill bit is inserted into the intraosseous injection device while the distal portion of the drill bit remains within a base portion of the carrier. The intraosseous injection device is used to inject a solution into a patient through the drill bit. The distal end of the drill bit is inserted into the base portion of the protective carrier while the proximal end of the drill bit remains in the intraosseous injection device. The proximal portion of the drill bit is removed from the intraosseous injection device such that the alignment sleeve at least partially houses the intraosseous drill bit.

In one embodiment, an intraosseous injection device comprises a tool having a distal portion, a proximal portion, and a solution dispensing opening. The distal portion of the tool has one or more cutting surfaces. The tool is configured to be rotatably coupled to a tool actuation mechanism. A housing has a distal end and a proximal end. The housing is configured to releasably receive a solution cartridge containing a solution. A solution dispensing mechanism is configured to dispense different types of solutions from the solution cartridge. A gripping member is configured to grip a proximal portion of the tool. A rotation device is configured to rotate the gripping member and thereby rotate the tool about an axis. The device is configured such that the proximal portion of the tool connects directly to the solution cartridge such that solution from the cartridge can be delivered through the solution dispensing opening. The tool is configured to rotate relative to the solution cartridge.

In another embodiment, a method of dispensing a solution comprises loading an ampoule of solution into a housing. A tool is placed in a gripping mechanism of the housing until the tool enters the ampoule to place the tool in communication with an interior portion of the ampoule. A distal end of the tool is placed into a patient. Solution is forced into the patient.

In another embodiment, an intraosseous injection tool delivery system comprises a tool having a distal portion, a proximal portion, and a solution dispensing opening. The distal portion of the tool has one or more bevels. The tool is configured to be rotatably coupled to a tool actuation mechanism. The tool is configured to be coupled to a protective carrier. A protective carrier is configured to be coupled to the distal portion of the tool for positioning the tool relative a gripping member and solution cartridge of an intraosseous injection device.

In another embodiment, an intraosseous injection device comprises a tool having a distal portion, a proximal portion, and a solution dispensing opening. The distal portion of the tool has one or more bevels. The tool is configured to be rotatably coupled to a tool actuation mechanism. A housing has a distal end and a proximal end. The housing has a cartridge receiving mechanism configured to releasably receive a solution cartridge containing a solution. The cartridge receiving mechanism is actuatable between a cartridge loading configuration and a solution dispensing configuration. A solution dispensing mechanism is configured to dispense solution from the solution cartridge through the tool when the cartridge receiving mechanism is in the solution dispensing configuration.

In another embodiment, an intraosseous injection device comprises a tool having a distal portion, a proximal portion, and a solution dispensing opening. The distal portion of the tool has one or more bevels. The tool is configured to be rotatably coupled to a tool actuation mechanism to rotate relative a solution cartridge. A housing couples the solution cartridge, a solution dispensing mechanism, a gripping member configured to grip a proximal portion of the tool, and a rotation device configured to rotate the gripping member and thereby rotate the tool about an axis. An adjustable protective sleeve mechanism at least partially covers the tool.

In another embodiment, an intraosseous injection system comprises a tool having a distal portion, a proximal portion, and a solution dispensing opening. The distal portion of the tool has one or more bevels. The tool is configured to be rotatably coupled to a tool actuation mechanism. The tool is configured to be coupled to a protective carrier. A protective carrier is configured to be coupled to the distal portion of the tool for positioning the tool relative a gripping member and solution cartridge of an intraosseous injection device. A handpiece comprises a housing having a cartridge receiving mechanism configured to releasably receive a solution cartridge containing a solution, a solution dispensing mechanism, a gripping member configured to grip a proximal portion of the tool, and a rotation device configured to rotate the gripping member and thereby rotate the tool about axis. The system is configured such that the proximal portion of the tool is connectable directly to the solution cartridge such that solution from the cartridge can be delivered through the solution dispensing opening. The tool is configured to rotate relative to the solution cartridge.

In another embodiment, an intraosseous injection device comprises a tool having a distal portion, a proximal portion, and a solution dispensing opening. The distal portion of the tool has one or more bevels. The tool is configured to be rotatably coupled to a tool actuation mechanism to rotate the tool, which can include a needle, about a first axis. A housing couples a solution cartridge, a solution dispensing mechanism, a gripping member configured to grip a proximal portion of the tool, and a rotation device. The rotation device is configured to rotate the gripping member and thereby rotate the tool about a first axis and rotate the solution cartridge about a second axis, the second axis being at an angle with respect to the first axis.

In another embodiment, an intraosseous injection device comprises a handpiece having a tool actuation mechanism and a solution dispensing mechanism. The solution dispensing mechanism comprises a solution cartridge. A tool has a distal portion, a proximal portion, and a solution dispensing opening. The distal portion of the tool has one or more bevels. In a particularly preferred embodiment, the distal portion of the tool has one or more cutting surfaces. The tool is configured to be rotatably coupled to the tool actuation mechanism. The proximal portion of the tool is configured to be coupled directly to the solution cartridge such that solution from the cartridge can be delivered through the solution dispensing opening. The tool is configured to rotate relative to the solution cartridge.

In one variation of the embodiment, the distal portion of the tool comprises a first right-handed cutting edge and a second left-handed cutting edge. In another variation, the distal portion of the tool comprises a steeped secondary angle. In another variation, the distal portion of the tool comprises a fluted outer surface. In another variation, the tool comprises one of a needle, a file, a drill bit, and a burr. In another variation, the tool is configured to be coupled to a carrier to facilitate coupling the tool to the handpiece. In another variation, the tool actuation mechanism is configured to oscillate the tool. In another variation, the tool actuation mechanism comprises one or more of a collet, a chucking a quick connection mechanism, a motor, a gear, a shaft, a spring, and a bearing. In another variation the tool is gripped by a collet or chucking mechanism that is configured not to have a rotating or oscillating motion. In another variation, the handpiece is configured for cordless operation. In another variation, the handpiece additionally comprises a sleeve mechanism. In another variation, the solution dispensing mechanism additionally comprises a cartridge receiving mechanism that is actuatable between a tilted cartridge loading configuration and a solution dispensing configuration. In another variation, the solution dispensing mechanism is configured to be manually controlled. In another variation, the solution dispensing mechanism additionally comprises one or more of a lever, rod, spring, gear, rack, and motor. In another variation, the solution dispensing mechanism controls the rate of delivery of solution.

BRIEF DESCRIPTION OF THE DRAWINGS

Further objects, features and advantages of the invention will become apparent from the following detailed description taken in conjunction with the accompanying figures showing illustrative embodiments of the invention, in which:

FIG. 2 is a sectional view of a front portion of the handpiece of the system of FIG. 1.

FIG. 3 is a perspective partial sectional view of a tool and tool carrier assembly of the system of FIG. 1.

FIG. 26 is another side view of the tool of FIG. 24, showing a notched portion.

FIG. 51B is an enlarged schematic view of a portion of the injection system of FIG. 51A.

Figure 1:
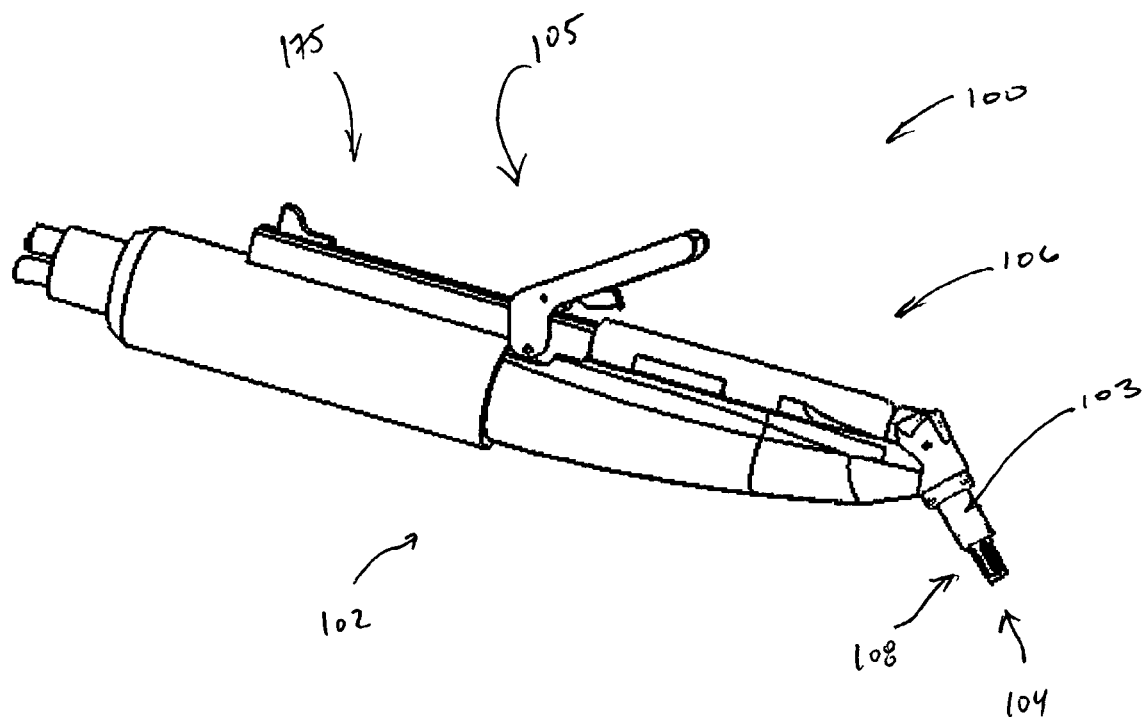
FIG. 1 is a perspective view of one embodiment of an injection system having a handpiece and a tool.

Throughout the figures, the same reference numerals and characters, unless otherwise stated, are used to denote like features, elements, components or portions of the illustrated embodiments. Moreover, while the subject matter of this application will now be described in detail with reference to the figures, it is done so in connection with the illustrative embodiments. It is intended that changes and modifications can be made to the described embodiments without departing from the true scope and spirit of the subject invention as defined by the appended claims.

DETAILED DESCRIPTION OF THE PREFERRED EMBODIMENTS

As should be understood in view of the following detailed description, this application is primarily directed to, though not necessarily limited to, a handpiece for medical applications, such as, for example, an intraosseous injection system.

FIGS. 1-17 illustrate one embodiment of an intraosseous injection system 100. FIG. 1 is a side perspective view of the intraosseous injection system 100. The system 100 comprises a handpiece 102 having a tool actuation mechanism 103 and a solution dispensing mechanism 105. A tool 104 (see FIG. 3) is configured to be rotatably coupled to the tool actuation mechanism 103. The actuation mechanism 103 is preferably coupled to a distal portion of the handpiece 102. As will be explained in detail below, the tool actuation mechanism 103 is configured to hold the tool 104, which can be any of a variety of medical instruments, such as, for example, a needle, a file, a dispensing tip, a drill, and/or a burr.

As shown in FIG. 1, the solution dispensing mechanism 105 preferably comprises a solution cartridge 106. The ampoule or cartridge 106 of a solution can be coupled with the handpiece 102. The handpiece 102 is configured to receive a cartridge or ampoule 106 of a solution. The solution can comprise, for example, an anesthetic, antibiotics, or any other fluid or semi-fluid material. As will be explained below, the tool 104 preferably has a distal portion, a proximal portion, and a solution dispensing opening. The distal portion of the tool 104 preferably has one or more bevels. In a particularly preferred embodiment, the distal portion of the tool 104 preferably has one or more cutting surfaces. The tool 104 can be a hollow structure, as will be discussed further below. The proximal portion of the tool 104 is configured to be coupled directly to the solution cartridge 106 such that solution from the cartridge 106 can be delivered through the solution dispensing opening. In some embodiments, the tool 104 is configured to rotate relative to the solution cartridge 106. In other embodiments, the tool 104 and solution cartridge 106 may rotate together or at different rates. In other embodiments, the handpiece is configured to received a tool 104 without rotation or oscillation.

As will be explained below, the system 100 is configured such that the tool 104 may be used to penetrate tissue at an injection site and deliver solution from the cartridge 106 to the injection site. The handpiece 102, in turn, is configured to control the rate of delivery of the solution precisely and safely from the cartridge 106 and through the tool 104 to the patient. In one embodiment, the system is configured to rotate, vibrate and/or oscillate the tool 104 relative to the cartridge 106. For example, the tool 104 may rotate and/or oscillate to perforate tissue while the cartridge 106 is held generally stationary within the handpiece 102. In other particularly preferred embodiments, the tool 104 may rotate and/or oscillate to perforate tissue while the cartridge 106 generally rotates and/or oscillates continuously or intermittently within the handpiece 102.

In one embodiment, the tool 104 punctures the ampoule 106 to place the tool 104 in fluid communication with the cartridge 106. In other embodiments, the tool 104 is directly or indirectly coupled to the cartridge 106 to place the cartridge 106 in fluid communication with the tool. One advantage of using the tool 104 to puncture the cartridge 106 includes minimizing the number of fluid delivery components between the cartridge 106 and the delivery site. Minimizing components preferably avoids leakage at joints and simplifies the manufacturing and assembly process. Additionally, another advantage of minimizing components between the cartridge 106 and the delivery site is that fewer components allow the overall drive train to become smaller. A smaller design is advantageous for positioning the injection system within a patient's mouth. A smaller design is also advantageous for use with younger patients that may have difficulty opening wide enough for a larger injection system.

With reference now to FIG. 2, the tool actuation mechanism 103 of the illustrated embodiment will now be described. The tool actuation mechanism 103 is preferably configured such that the tool 104 may be quickly coupled to the handpiece 102 and quickly removed from the handpiece 102. As shown in FIG. 2, the handpiece 102 comprises a housing 120. A housing retainer 122 preferably is coupled with the housing 120 to hold a collet housing 126 within the housing 120.

As shown in FIG. 2, the tool actuation mechanism 103 comprises a quick connect mechanism such as a collet 124 that is moveably position in a collet housing 126. In the illustrated embodiment, the collet 124 comprises a plurality of radially expandable or collapsible lever arms, which are separated by one or more gaps. However, it should be appreciated that although a specific collet mechanism is shown and described, other types of collets or chucking mechanisms can be successfully used in other embodiments. A collet spring 130 is positioned abut the collet 124 through a collet retainer 128 proximally within the collet housing 126. A button 132 is coupled with a proximal portion of the collet 124 at a button retainer 134 portion. The button 132 is also coupled with the collet retainer 128 that is, in turn, coupled to the collet 124. The button 132 and collet retainer 128 are configured to move the collet 124 distally within the collet housing 126 against a biasing member, such as the biasing force of the collet spring 130. As the collet 124 moves distally, a distal portion of the collet 124 moves relative to a locking bushing 140. The locking bushing can be eliminated in some embodiments, and a locking feature can be part of the collet housing 124. As the distal end of the collet 124 moves past the locking bushing 140, the collet 124 expands such that the collet 124 can receive the tool 104 when the distal portion of the collet 124 is distal of the locking bushing 140. When the button 132 is released, the collet spring 130 applies a proximal force to the collet 124 causing the collet 124 to compress around the tool 104 as the distal end of the collet 124 is compressed by the locking bushing 140. The collet spring 130 thus acts as a biasing member to bias the collet 124. Alternatively, the collet retainer can be used to expand the collet to receive a tool without the use of the spring. In this manner, the collet 124 is configured to hold the tool 104 when the distal portion of the collet 124 is positioned within the locking bushing 140, as described further below in connection with FIGS. 9-10.

FIG. 2 shows the collet housing 126 held within the housing 120 by the housing retainer 122 and one or more bearings 138. The collet housing 126 preferably is rotatable or oscillatable within the housing 120. In this manner, rotation or oscillation of the collet housing 126 rotates or oscillates the collet 124. The collet housing 126 has a mating gear 144 configured to be coupled to a gear shaft 142 of the tool actuation mechanism 103. The gear shaft 142 preferably is coupled to a motor, e.g., an air or electric motor, as will be described in more detail below with reference to FIGS. 15-17.

In the illustrated embodiment, when the tool 104 is held within the collet 124, the tool 104 punctures the ampoule 106 to place the tool 104 in fluid communication with the ampoule 106. One advantage of using the tool 104 to puncture the cartridge 106 includes minimizing the number of fluid delivery components between the cartridge 106 and the delivery site. Minimizing components preferably avoids leakage at joints and simplifies the manufacturing and assembly process. Additionally, another advantage of minimizing components between the cartridge 106 and the delivery site is that fewer components allow the overall drive train to become smaller. When the collet 124 moves distally to open the collet mechanism, the tool 104 may be withdrawn from the cartridge 106 for removal of the tool 104.

As shown in FIG. 2, in the illustrated embodiment, the handpiece also comprises a sleeve 108, which is positioned distally of the collet 124. The sleeve 108 preferably covers at least partially the tool 104 when it is positioned within the collet 124. In one embodiment, topical anesthetic can be applied to the sleeve 108 such that it can be used to transfer topical anesthetic to the injection site. The sleeve 108 can also induce pressure at the topical site and/or be used to control the depth of insertion of the tool 104. A sleeve spring 136 can keep the sleeve 108 automatically down when topical contact is removed. The sleeve 108 can also be used to cool down the tissue to reduce pain, by applying a cooling agent to the sleeve 108 directly by way of ethyl chloride or a freon. The sleeve 108 has a thermally conductive material or coating to be able to hold the cold during function. The sleeve mechanisms are described in greater detail below in connection with FIGS. 9-11.

FIGS. 3-8 illustrate one embodiment of an aligning sleeve 150 and carrier 152 for inserting the tool 104, e.g., a needle, into the tool actuation mechanism 103 of the handpiece 102. As explained below, the tool 104 can be coupled with the carrier 152 to facilitate coupling and removing the tool 104 from the handpiece 102. The carrier 152 is configured to grasp or hold the tool 104 so that the tool 104 can be safely positioned within the handpiece 102. The carrier 152 can be made of any suitable material. In one embodiment, the carrier 152 is made of plastic. The carrier 152 preferably holds the bared needle 104 using gripping elements 152a (e.g., resilient prongs, lever arms, O-rings and the like). The needle 104 can be slip fit between the gripping elements 152a. In another embodiment, the carrier holds a needle and a hub assembly by encapsulating flexing elements of the hub inside a cavity. After the needle is positioned within the handpiece 102 and the procedure is completed, the flexing elements can be reinserted back in the carrier 152 to facilitate the removal of the needle/hub assembly from the collet mechanism.

Figure 3A:
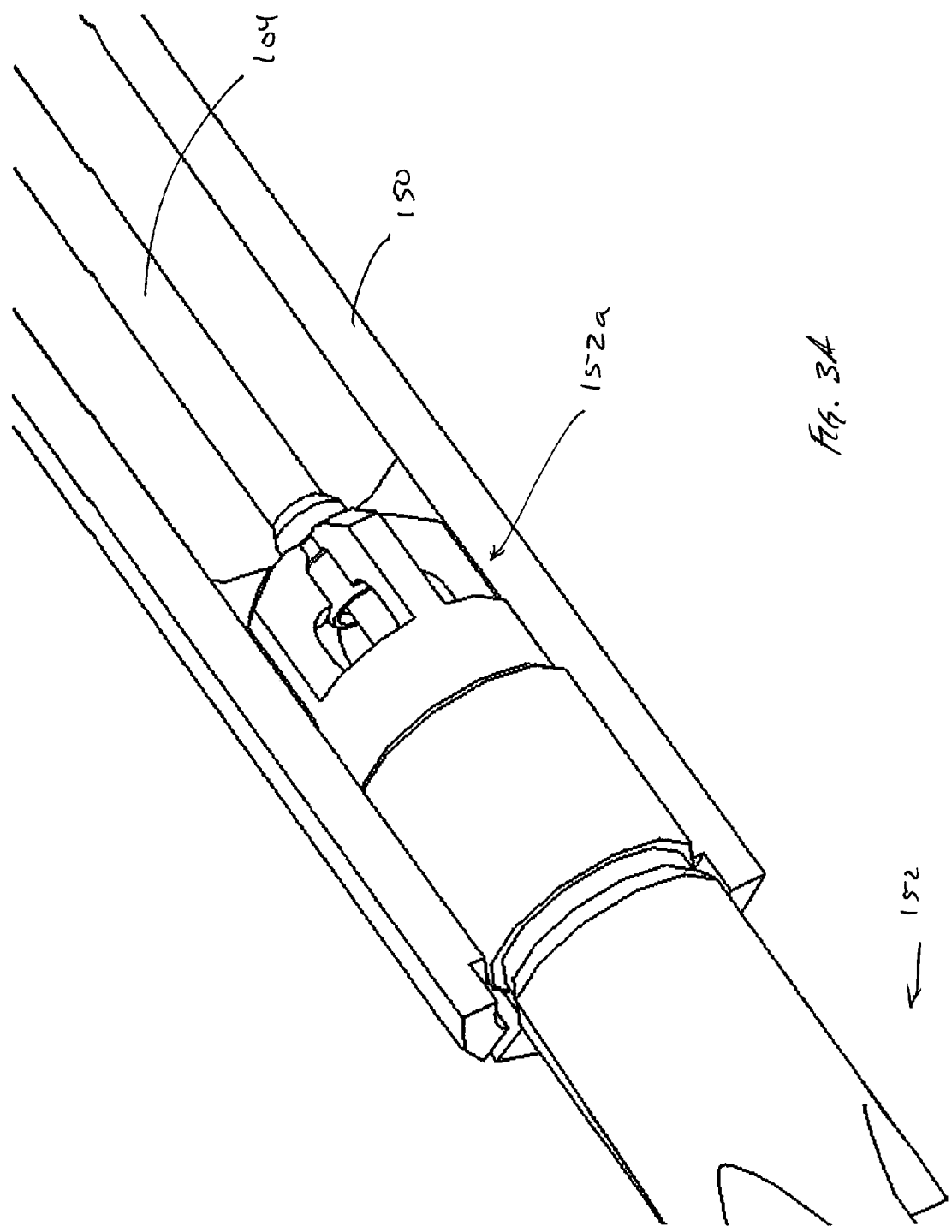
FIG. 3A is an enlarged perspective partial sectional view of a tool and tool carrier of FIG. 3.
Figure 3B:
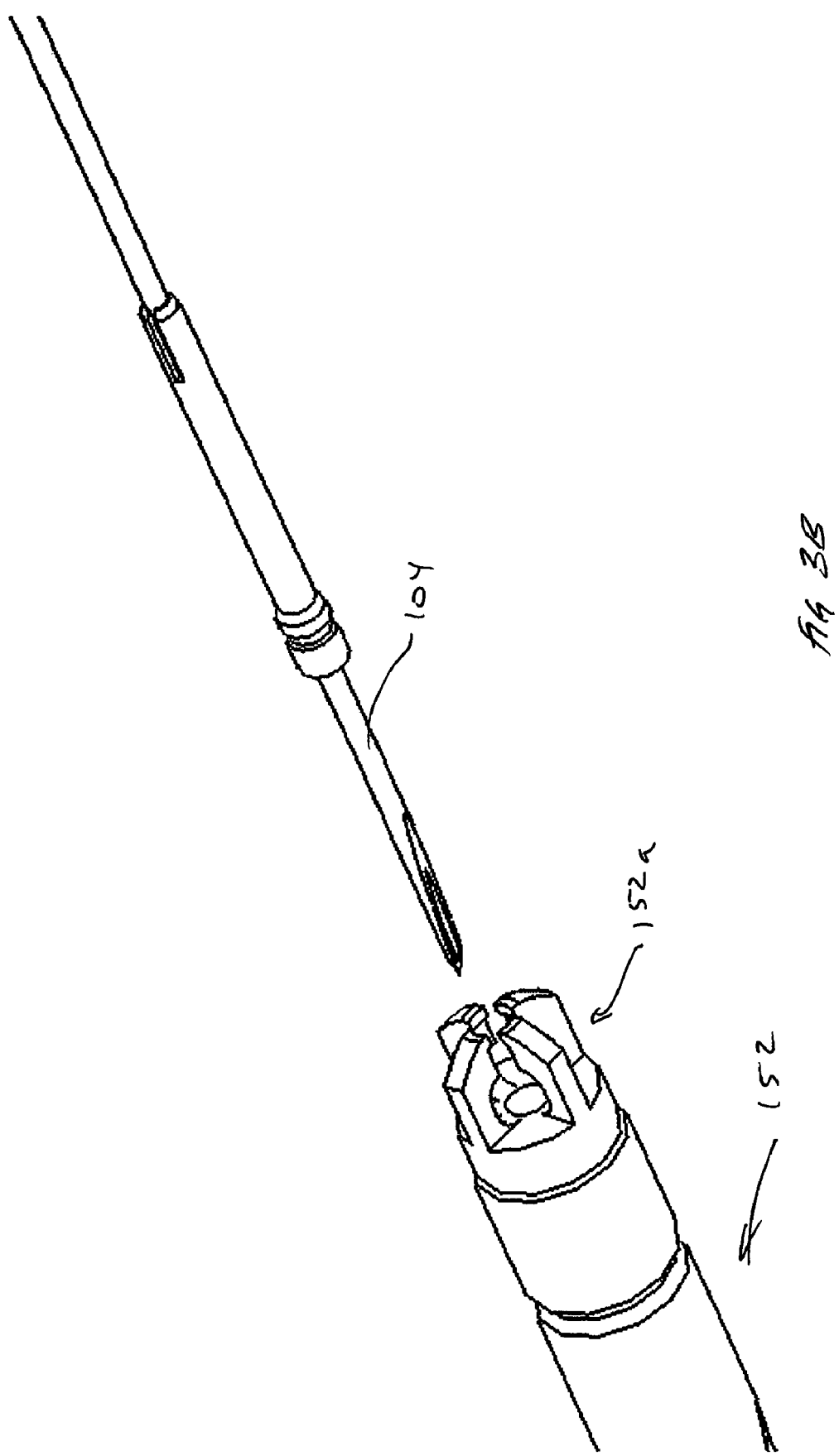
FIG. 3B is an exploded view of the tool and tool carrier assembly of FIG. 3.
Figure 3C:
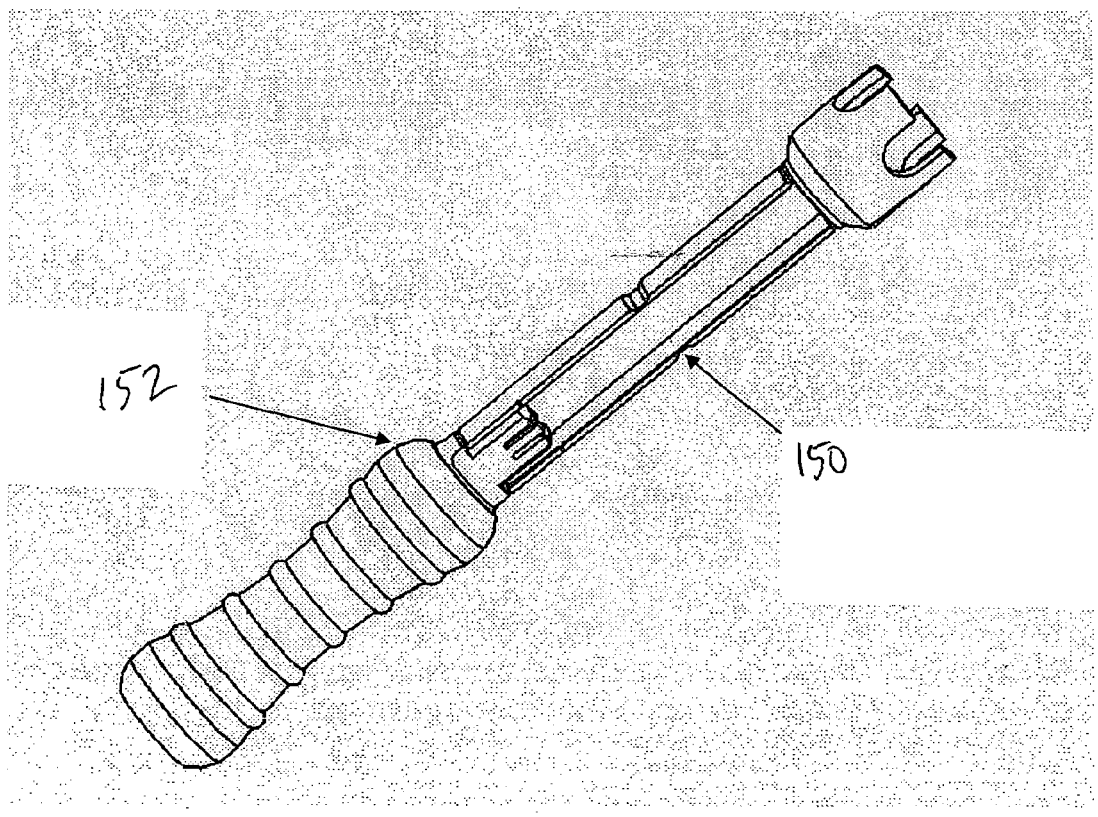
FIG. 3C is a perspective view of another embodiment of a tool carrier assembly and alignment sleeve.
Figure 3D:
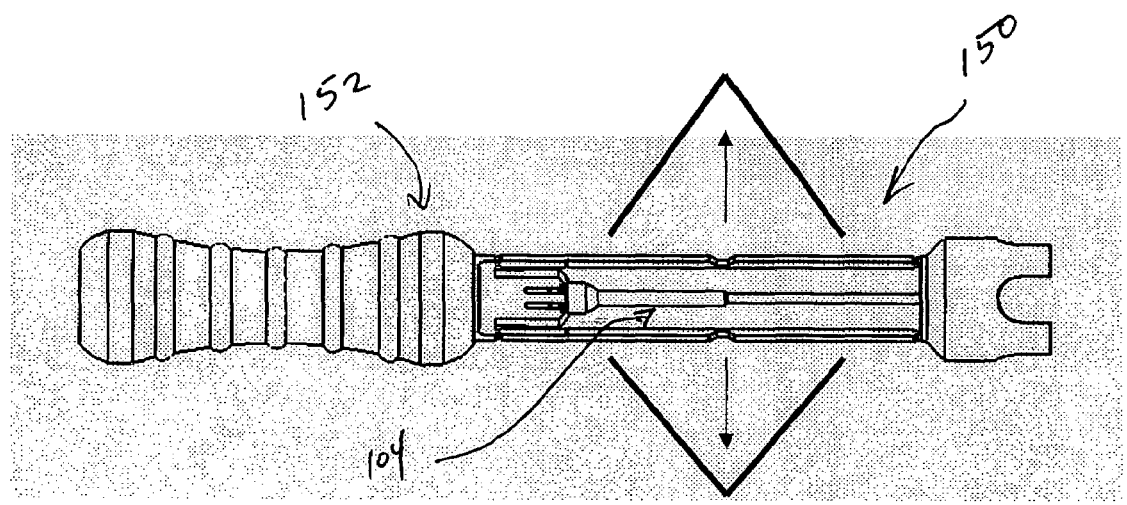
FIG. 3D is a perspective view of the tool carrier assembly and alignment sleeve of FIG. 3C, with a tool.

Flexing elements can also be incorporated on the carrier as shown in FIG. 3A. The flexing elements preferably engage a groove on the hub or the tool and allow for insertion or removal of the tool from the collet or chucking mechanism. Alternatively, the tool can be coupled with the carrier using a thread feature, which requires the end user to open the gripping mechanism, load the tool using the carrier, close the mechanism, and then unthread the carrier from the tool. The needle can be coupled or connected to the hub using current manufacturing methods, such as molding, insert molding, welding, interlocking, sealing, or light-cure adhesive technologies. In another embodiment, the alignment sleeve 150 and carrier 152 can be made as a one piece as shown in FIGS. 3C and 3D. A one-piece design may reduce the cost of manufacturing. In some embodiments, the carrier does not include a cap portion. In some embodiments, the tool can be packaged with a carrier inside a pouch if desired to reduce cost. As shown in FIGS. 3C and 3D, the alignment sleeve can be part of the carrier in some embodiments. The alignment sleeve 150 can have two or more flexing arms in some embodiments. As shown in FIG. 3D, as the carrier 152 and alignment sleeve 150 are pushed against the face of the handpiece, the flexing elements can flex outwardly and the carrier portion can position the tool 104 within the gripping mechanism of the handpiece.

As shown in FIGS. 3-8, the aligning sleeve 150 preferably is configured to be aligned with a distal portion of the handpiece 102. In one embodiment, the aligning sleeve 150 can be positioned within a distal portion of the handpiece 102. In another embodiment, the aligning sleeve 150 can be positioned about a distal portion of the handpiece 102. The aligning sleeve 150 preferably cooperates with the handpiece 102 such that the tool 104 is aligned with the collet mechanism for insertion into the handpiece 102. The alignment sleeve is configured so it has a retaining or frictional feature that engages the distal portion of the handpiece so when the carrier/alignment sleeve assembly is removed the alignment sleeve moves back to its original position to cover the needle during unloading procedures. This unique feature automatically covers the proximal portion of the tool to protect the end user and eliminate the need to recap, as described further below with reference to FIGS. 5A-5Q.

Figure 4:
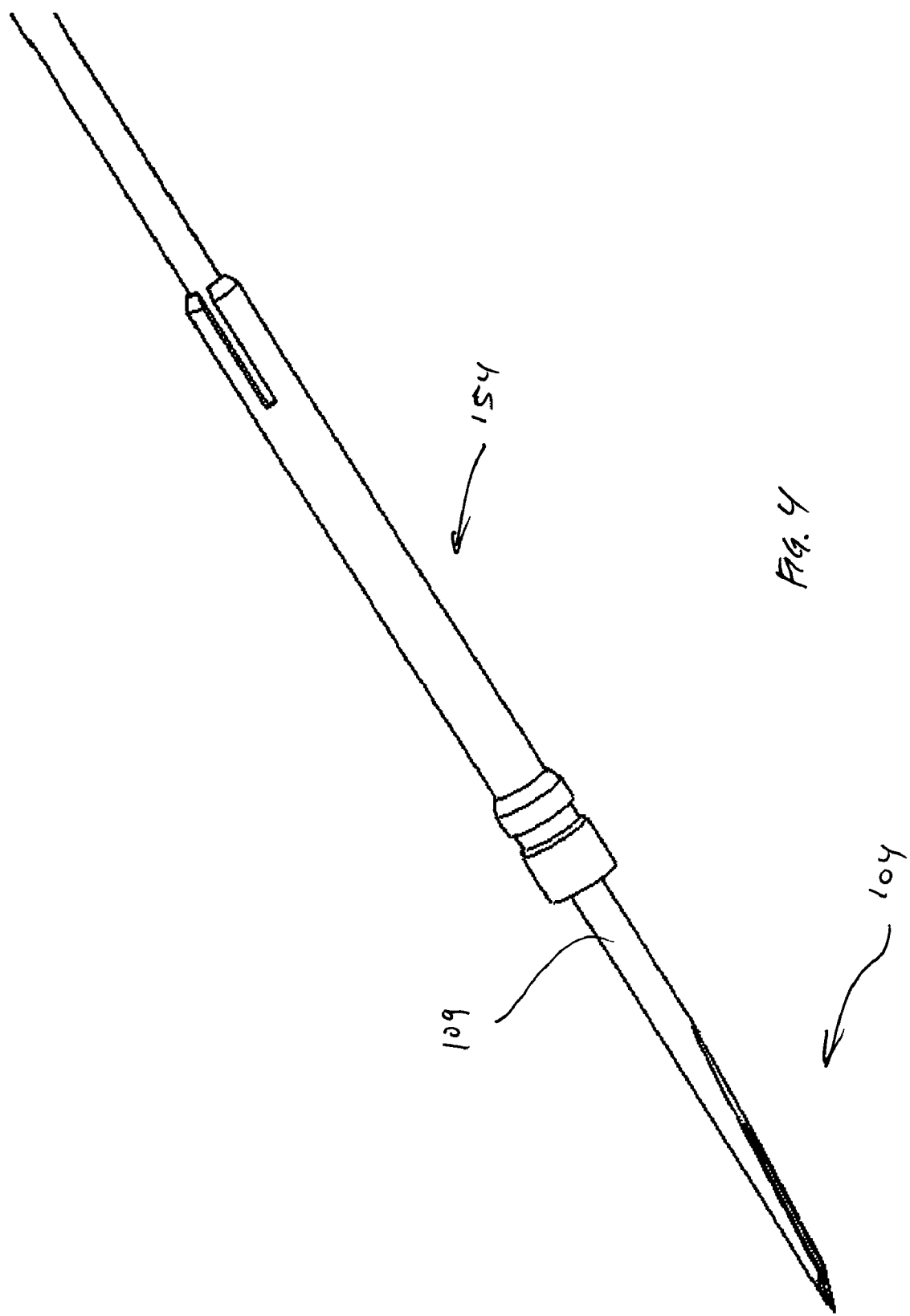
FIG. 4 is a perspective view of the tool showing a hub assembly of the system of FIG. 1.

As shown in FIG. 4, in the illustrated embodiment, the tool 104 includes a hub 154 having a collapsible outer diameter for gripping the tool 104. In another embodiment the hub 154 does not have a collapsible outer diameter to assist in its removal from the gripping mechanism. In other embodiments, the tool 104 does not have a hub. The hub 154 can be made out of any suitable material, e.g., plastic or metal. The hub 154 can be coupled with the needle 104 in any suitable manner. In one embodiment, a metal hub 154 is press-fitted onto the outside diameter of the needle 104. The hub 154 can also be laser welded to the needle 104 in some embodiments. The plastic hub can be insert molded, adhesive bonded, and/or welded to the needle. In some cases, the hub 154 can be formed integrally with the tool 104. In some embodiments, the needle 104 has an amorphous diamond coating 109 to reduce friction and minimize insertion pain. The reduced friction coating 109 also can reduce the risk that the needle 104 will be dislodged or debonded from the hub 154.

As shown in FIGS. 5-8, the tool 104 can be inserted into the handpiece 102 by twisting off a protective cap 156, which is coupled of the distal end of the carrier 152. This cap 156 can be eliminated if other packaging options are desired. It is also understood that the carrier and or the sleeve do not need to be part of the packaging and they may be a separate purchased tool or fixture. The user then pushes down on the button 132 of the handpiece 102 to open the collet 124, as described further below with reference to FIGS. 9-10, and inserts the needle 104 and carrier assembly into the handpiece 102 until the needle 104 stops within the collet 124 and punctures a penetrable seal 107 of the cartridge 106. The button 132 is then released and the packaging carrier 152 is removed while the sleeve 108 moves downwardly to cover the needle 104 automatically, which is described further below with reference to FIGS. 10-11.

Figure 5A:
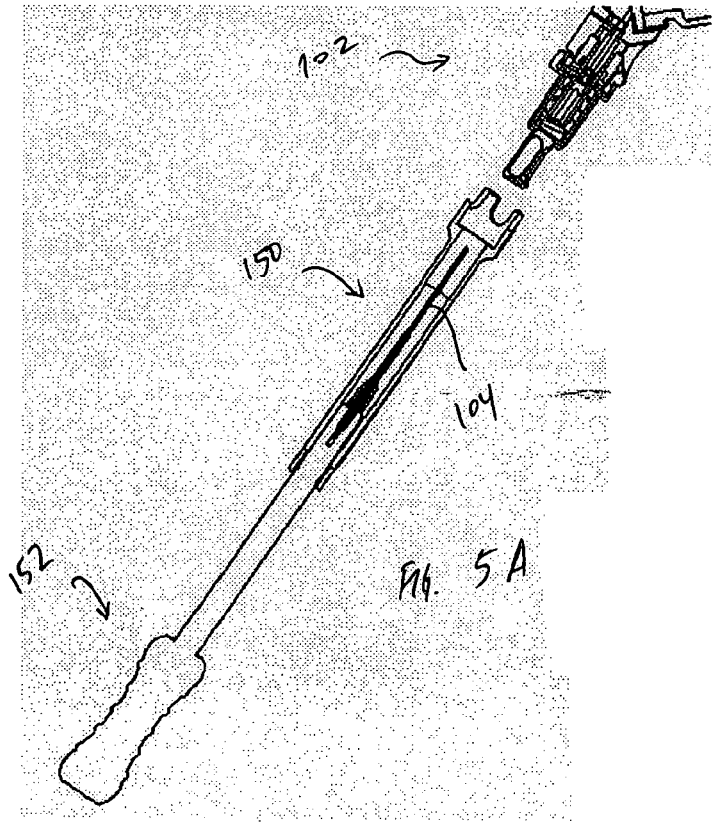
FIGS. 5A-5Q are schematic views illustrating procedures for loading and unloading a tool on a handpiece.
Figure 5B:
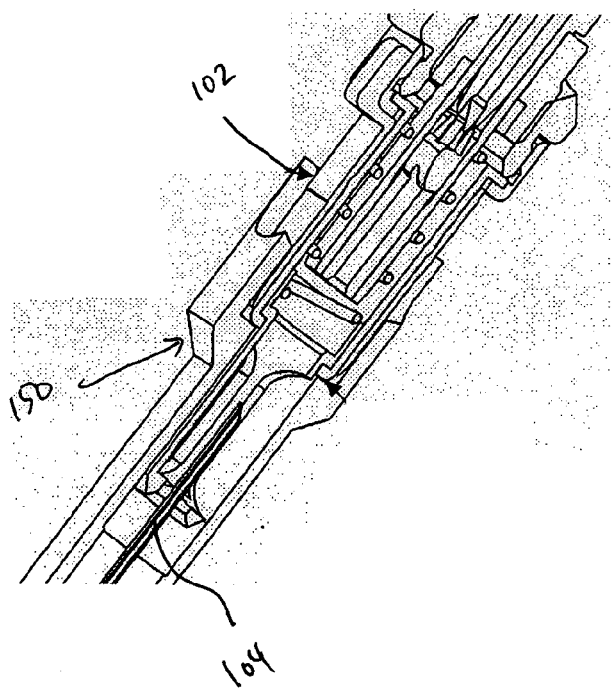
FIG. 5 is a perspective view of the tool and tool carrier assembly of FIG. 3 and a cap, illustrating a portion of a technique for using the system of FIG. 1.
Figure 5E:
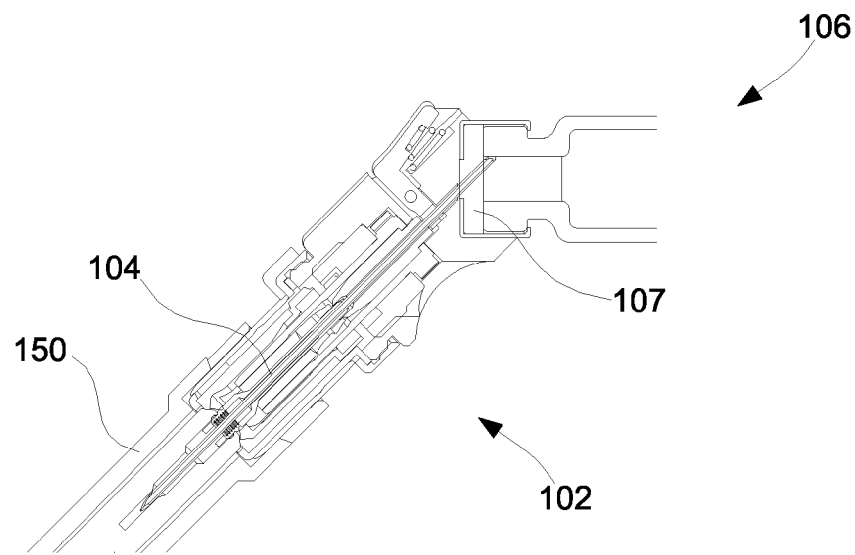
Figure 5F:
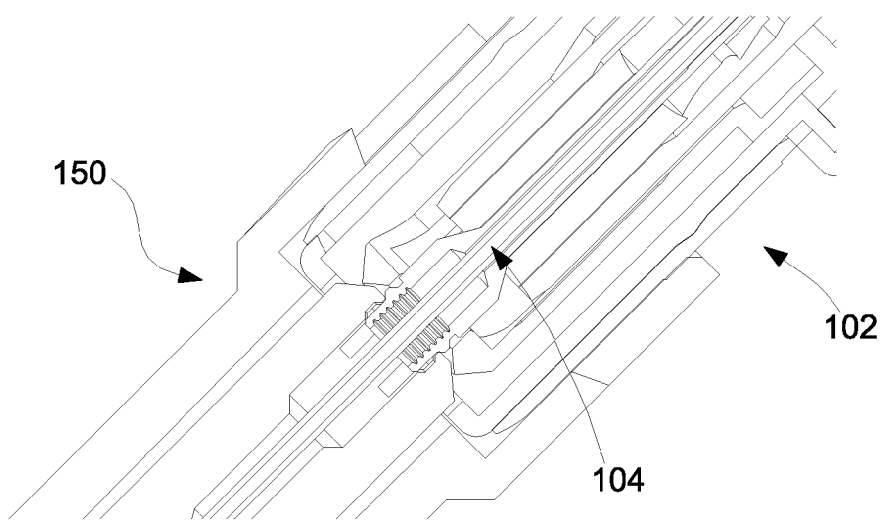
Figure 5J:
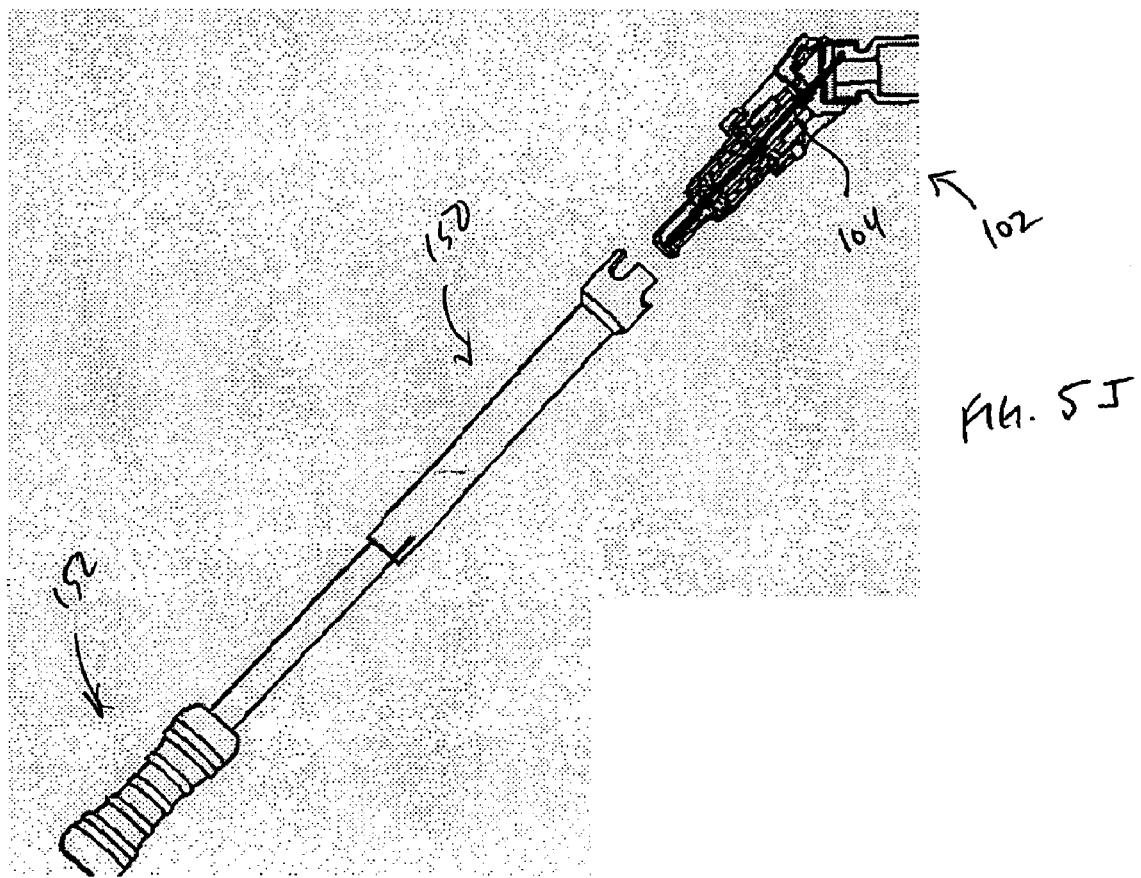
Figure 6:
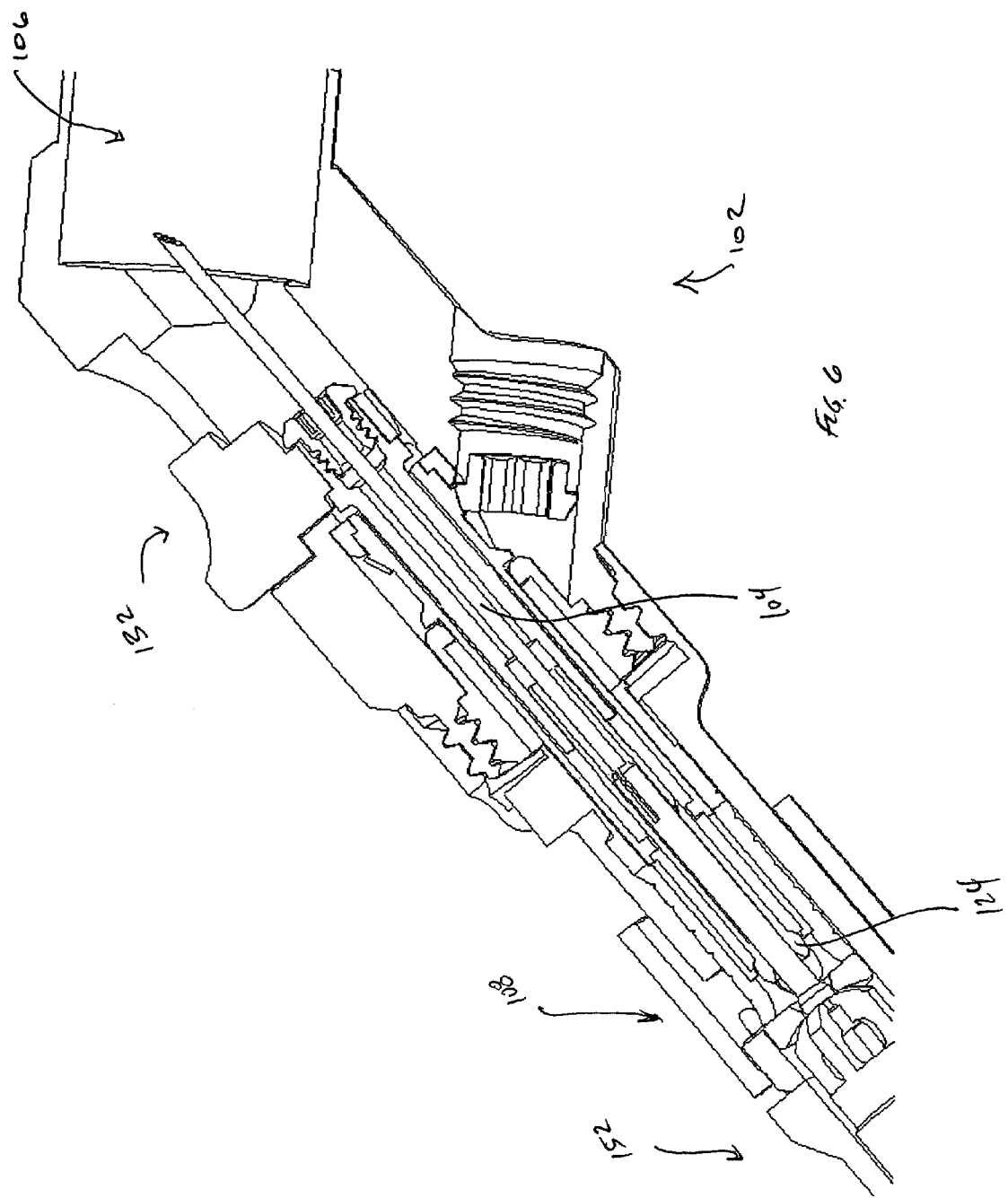
FIG. 6 is a sectional view of the tool and tool carrier assembly of FIG. 3 loading the tool into the handpiece of the system of FIG. 1, with a collet mechanism of the system open to receive the tool.

For example, in one embodiment, as shown in FIGS. 5A-5Q, a tool can be loaded and/or unloaded from the handpiece. FIGS. 5A-5J illustrate a procedure for loading the tool. With reference to FIGS. 5A and 5B, a button on the handpiece is depressed to open the gripping mechanism as the end user moves the assembly towards the handpiece. The alignment sleeve is inserted into the handpiece until it stops up against the surface of the handpiece. At that time the alignment sleeve flexing element are frictionally fitted on the outer diameter of the handpiece. In some embodiments, the button of the gripping mechanism does not need to be depressed since the tool's outer diameter can cause the gripping element to expand by pushing the tool forward. With reference to FIGS. 5C and 5D, the carrier is then advanced forward until it contacts the topical sleeve and begins pushing the sleeve inwardly, which causes the spring to compress. With reference to FIGS. 5L and 5F, the carrier is pushed until it stops when the hub contacts the gripping mechanism. At this time the button is released to grip the tool. Thus, the hub covers a first portion of the outer surface of the tool (e.g. a standard type needle), and the gripping mechanism (e.g. a gripping device) is configured to grip a second portion of the outer surface of the tool not covered by the hub. With reference to FIGS. 5G and 5H, the carrier is moved away from the handpiece, which causes the sleeve to move downwardly as the spring expands. The alignment sleeve is stationary at this time due to the fact that is frictionally fitted on the handpiece. The flexing elements of the alignment sleeve snap into the groove of the carrier as the carrier is moved away. With reference to FIG. 5J, after the flexing fingers of the alignment sleeve snap into the carrier's groove and as the carrier continues to move away from the handpiece the alignment sleeve is now disengaged from the handpiece since the snap force between the carrier and the alignment sleeve is higher than the frictional force or snap force between the alignment sleeve and the outer diameter of the handpiece.

FIGS. 5K-5Q illustrate a procedure for unloading the tool. With reference to FIGS. 5K and 5L, the alignment sleeve/carrier assembly is inserted into the handpiece all the way until the alignment sleeve contacts the face of the handpiece and continues moving the carrier forward, which causes the sleeve to move inwardly into the handpiece as previously described in the loading procedure. At this time the carrier engages the hub. With reference to FIGS. 5M and 5N, the button is depressed to open the gripping mechanism and the carrier, which is now attached to the tool, is removed away from the handpiece. In some embodiments, the griping mechanism can be opened up prior to the carrier engaging the hub. The carrier continues to move away from the handpiece, which causes the sleeve to move downwardly as the spring expands. The alignment sleeve is stationary at this time due to the fact that is frictionally fitted on the handpiece. With reference to FIG. 5P, the carrier continues to move away from the handpiece until the flexing elements of the alignment sleeve snap into the groove of the carrier as previously described on the loading procedure. With reference to FIG. 5Q, after the flexing fingers of the alignment sleeve snap into the carrier's groove and as the carrier continues to move away from the handpiece, the alignment sleeve is now disengaged from the handpiece since the snap force between the carrier and the alignment sleeve is higher than the frictional force or snap force between the alignment sleeve and the outer diameter of the handpiece. The tool, which is automatically covered by the alignment sleeve, can now be disposed of in the appropriate container.

Figure 9:
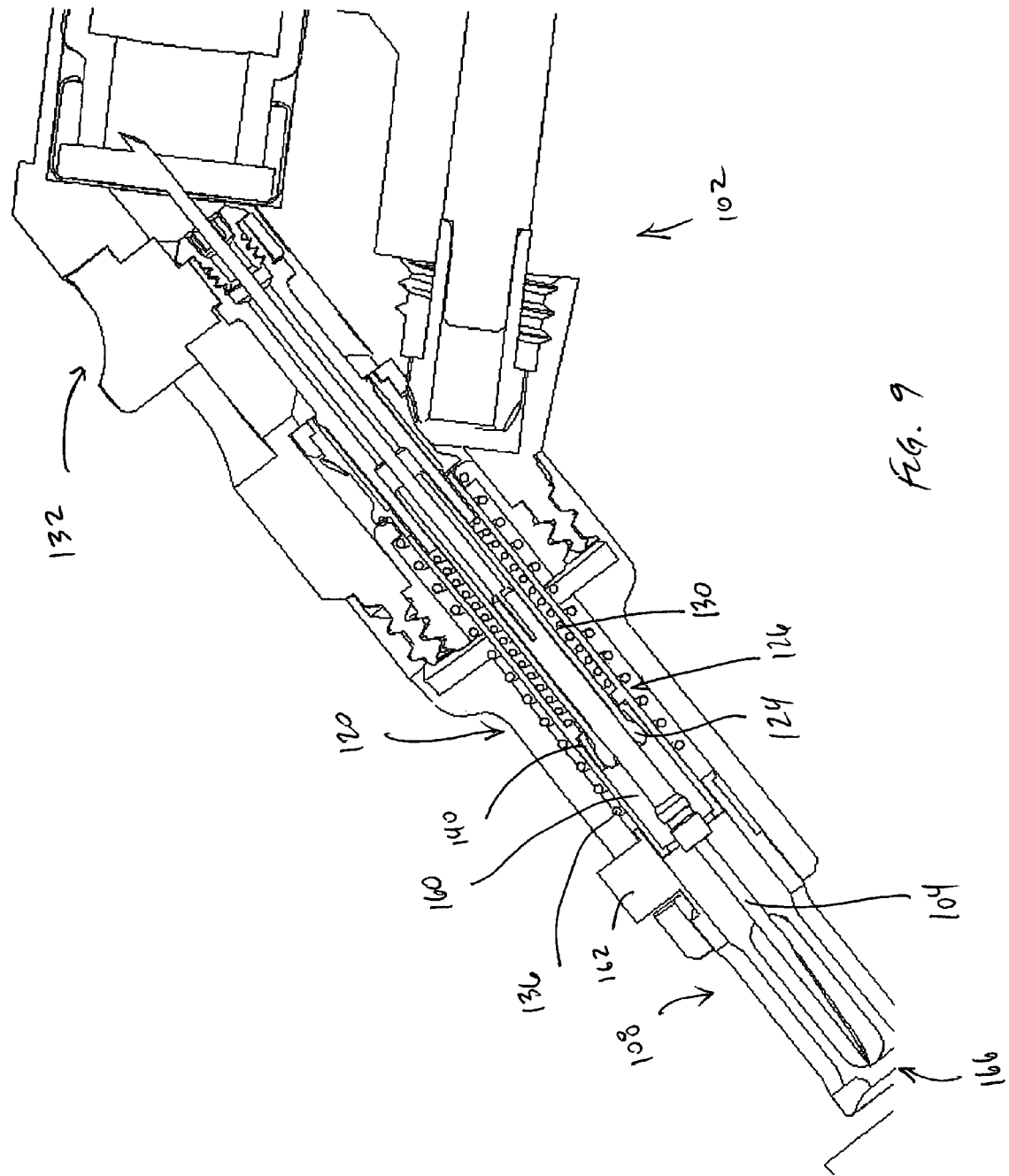
FIG. 9 is a sectional view of a portion of the handpiece of FIG. 1, with the tool held in the handpiece by handpiece components.
Figure 10:
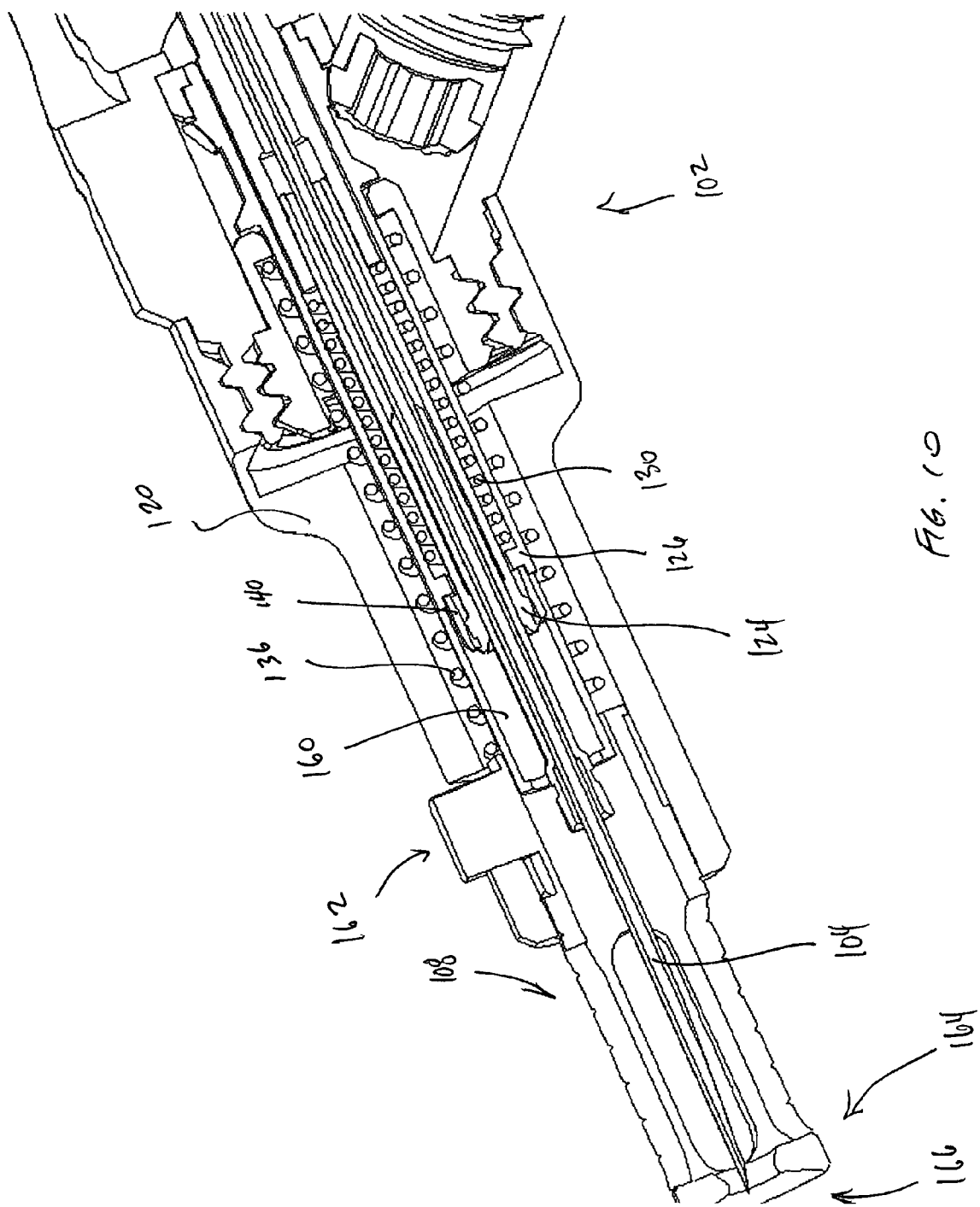
FIG. 10 is an enlarged sectional view of a portion of the system of FIG. 1, illustrating handpiece components holding the tool.

As shown in FIGS. 9-10, the collet opening feature preferably prevents accidental opening of the collet 124 while in use. The spring force of the collet spring 130, when the collet 124 is at the closed position, acts in the same direction as the acting force of the needle 104. The collet 124 in the closed position provides a space 160 between the locking bushing 140 and the collet housing 126 inner surface to allow for downward movement of the collet 124 prior to collet opening, which causes the needle 104 to pullout of the ampoule 106. The clearance should be larger than the space 160 to allow for the collet 124 to surpass the collet housing 126 opening of the distal end. While opening the collet 124, the locking bushing 140 preferably remains enclosed in the housing 126 while the collet 124 moves away and dislodges from the bushing 140.

Figure 11:
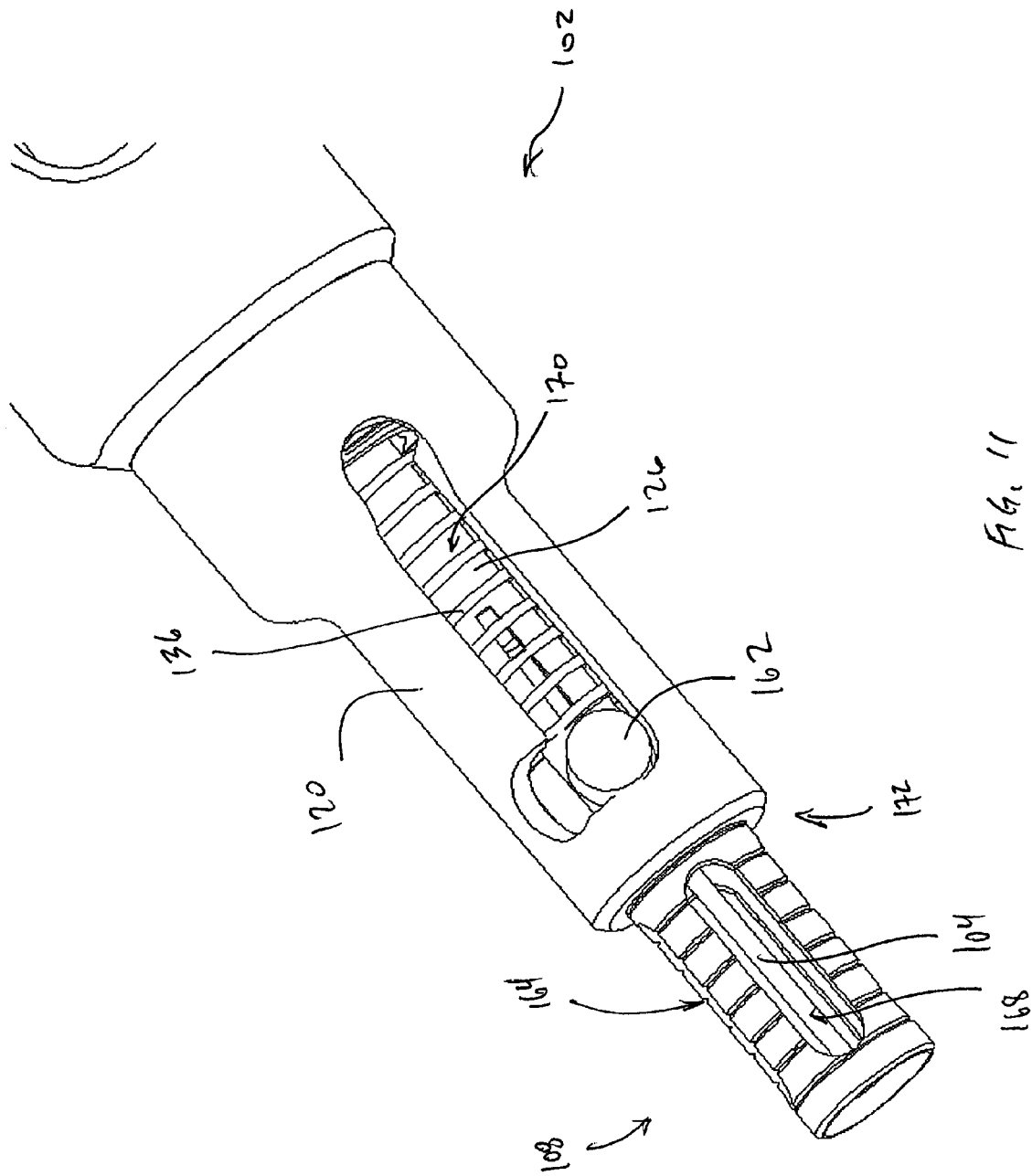
FIG. 11 is an enlarged perspective view of a portion of the system of FIG. 1, illustrating a sleeve of the system.

As shown in FIGS. 9-11, the sleeve spring 136 keeps the sleeve 108 automatically down when topical contact is removed. A locking feature 162, e.g., a tab, prevents upward movement of the sleeve 108 when not in use. Grooves 164 on the sleeve 108 provide visual depth control. The sleeve 108 has a small distal hole 166 to prevent bending of the needle 104. A skeleton body, e.g., a hole 168, and or a see-through material can allow for viewing of needle 104. Axial holes or grooves 170 allow for sleeve axial movement, provide access to the tab, and facilitate assembly. The face 172 provides a stop when assembling the needle 104 using the carrier 152. The protective sleeve 108 preferably is independent of the collet mechanism 124. The locking feature 162 should allow for adequate gripping during locking and unlocking. The sleeve spring 136 is slightly compressed to provide a downward force to keep the sleeve 108 down. The top section of the sleeve 108 preferably can be configured to interface with a standard syringe or a handpiece 102. In one embodiment, the sleeve can be connected to the handpiece such that it has a tendency to self lock. In one embodiment, this can be achieved by having a torsional spring that couples the sleeve to the housing. In some embodiments, a self locking sleeve advantageously reduces the chances of accidental injury.

Figure 12:
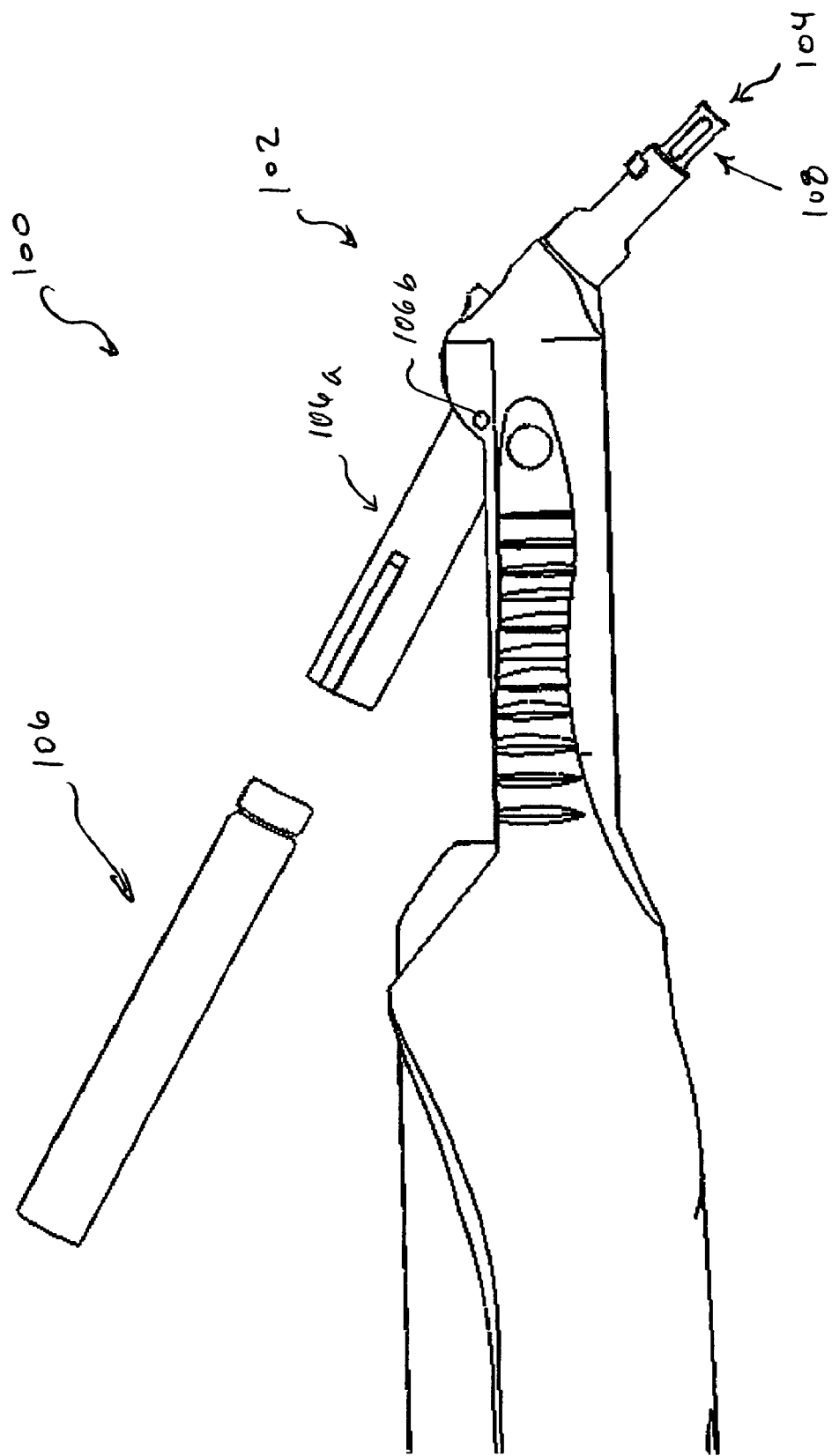
FIG. 12 is an exploded perspective view of the system of FIG. 1, showing a cartridge and a cartridge receiving portion of the handpiece.
Figure 13:
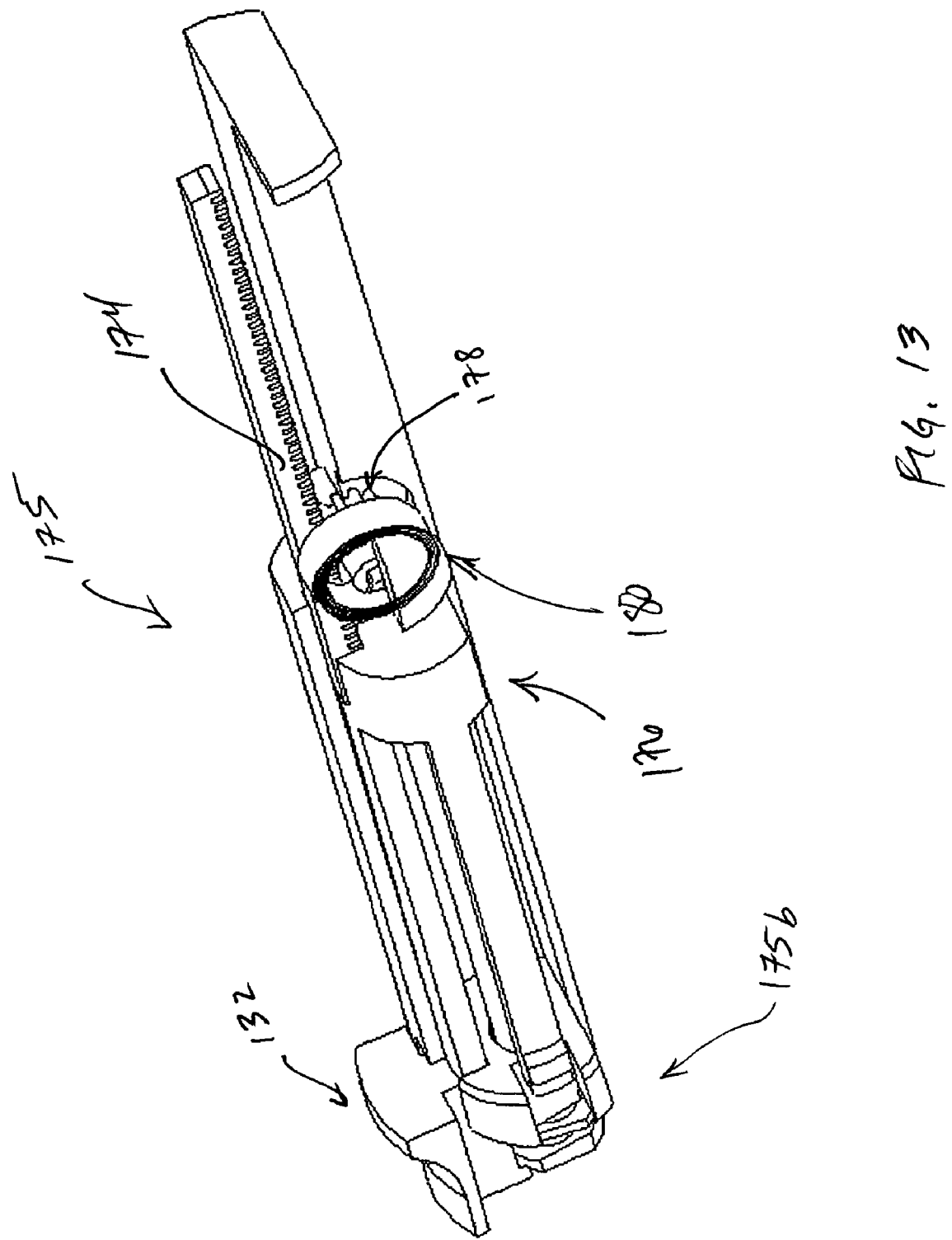
FIG. 13 is a perspective sectional view of a dispensing mechanism of the system of FIG. 1.
Figure 14:
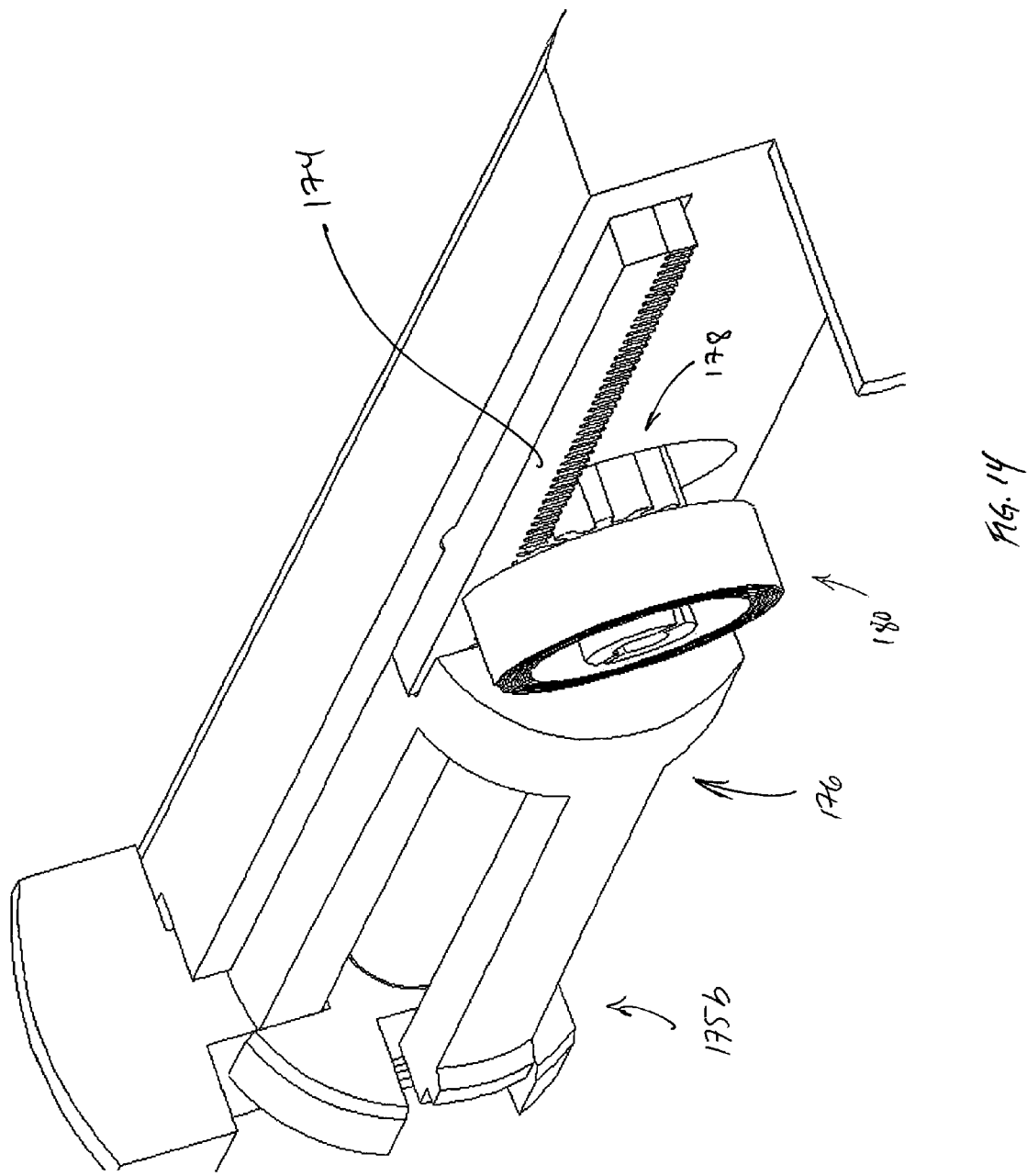
FIG. 14 is an enlarged perspective sectional view of the dispensing mechanism of FIG. 13.

FIG. 12 illustrates one technique for loading the cartridge 106 or ampoule of solution into the handpiece 102. In this embodiment, the handpiece 102 includes a sleeve 106a, which is pivotally connected at a pivot 106b to the handpiece 102. As shown, the sleeve 106a may be pivoted away from the body of the handpiece 102 such that the ampoule 106 may be inserted into the sleeve 106a. The sleeve 106b may then be back towards the handpiece to position the ampoule 106 generally along the longitudinal axis of the handpiece 102.

The contents of the ampoule 106 can be delivered in a variety of manners. For example, in FIGS. 13-15, the injection system 100 includes a mechanism 175, which comprises gear racks 174, gear rods 176, spur gears 178 and a power spring mechanism 180. The gear rod 176 and a lever or button 132 can be combined with the gear 178 and the rack 174 and assembled with a power spring 180. The power spring 180 is wound up when lever and rod 176 combination 175 is locked into the handpiece body (see FIG. 1). The user unlocks the lever 132, which makes the power spring 180 unwind. The spring 180 preferably rotates the gear 178, making the rack 174 move towards the front end of the handpiece 102. The rack 174 is connected to the rod 176, which contacts a dispensing mechanism such as a cartridge plunger 1 75b. The cartridge plunger 1 75b moves relative to the cartridge 106 as it is driven by the gear system. Driving the plunger into the cartridge 106 causes the solution to be dispensed through the tool 104, for example by applying pressure to the solution within the cartridge. Of course, those of skill in the art will recognize that in other embodiments any variety of other types of mechanisms may be used as dispensing mechanisms to dispense the material from the ampoule 106, including but not limited, to other types of plunger mechanisms.

Figure 15:
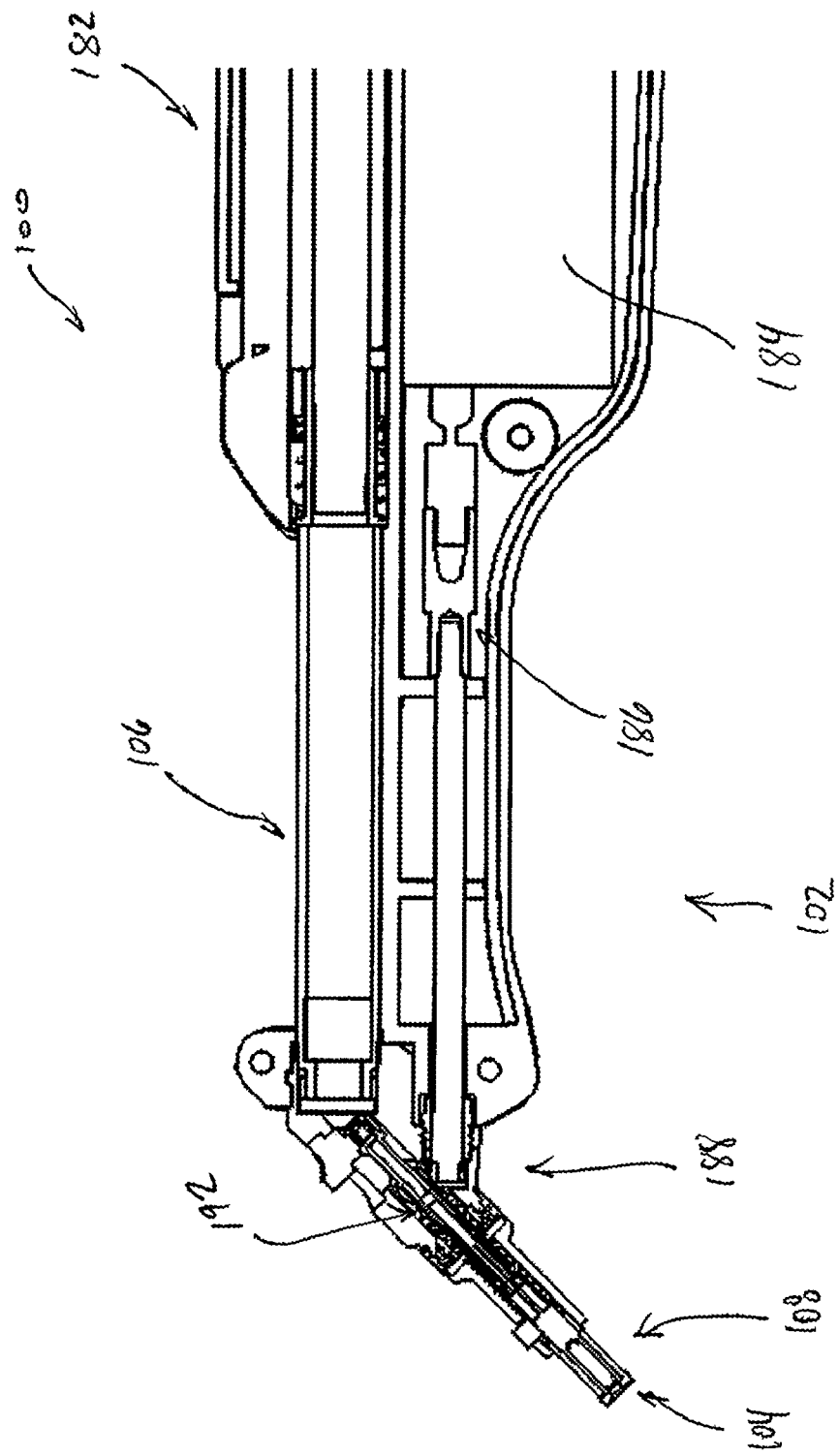
FIG. 15 is a schematic sectional view of a portion of the system of FIG. 1, showing a motor and gear system.
Figure 16:
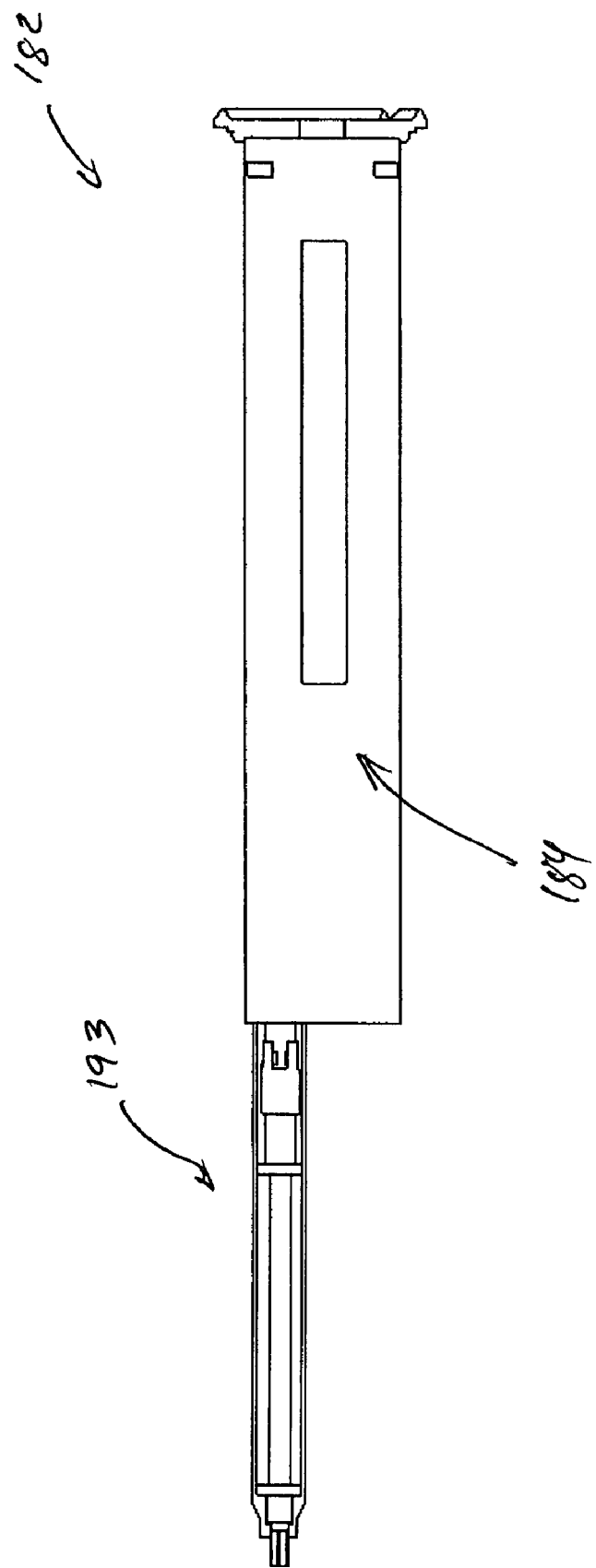
FIG. 16 is a schematic perspective view of the motor and gear system of FIG. 15.
Figure 17A:
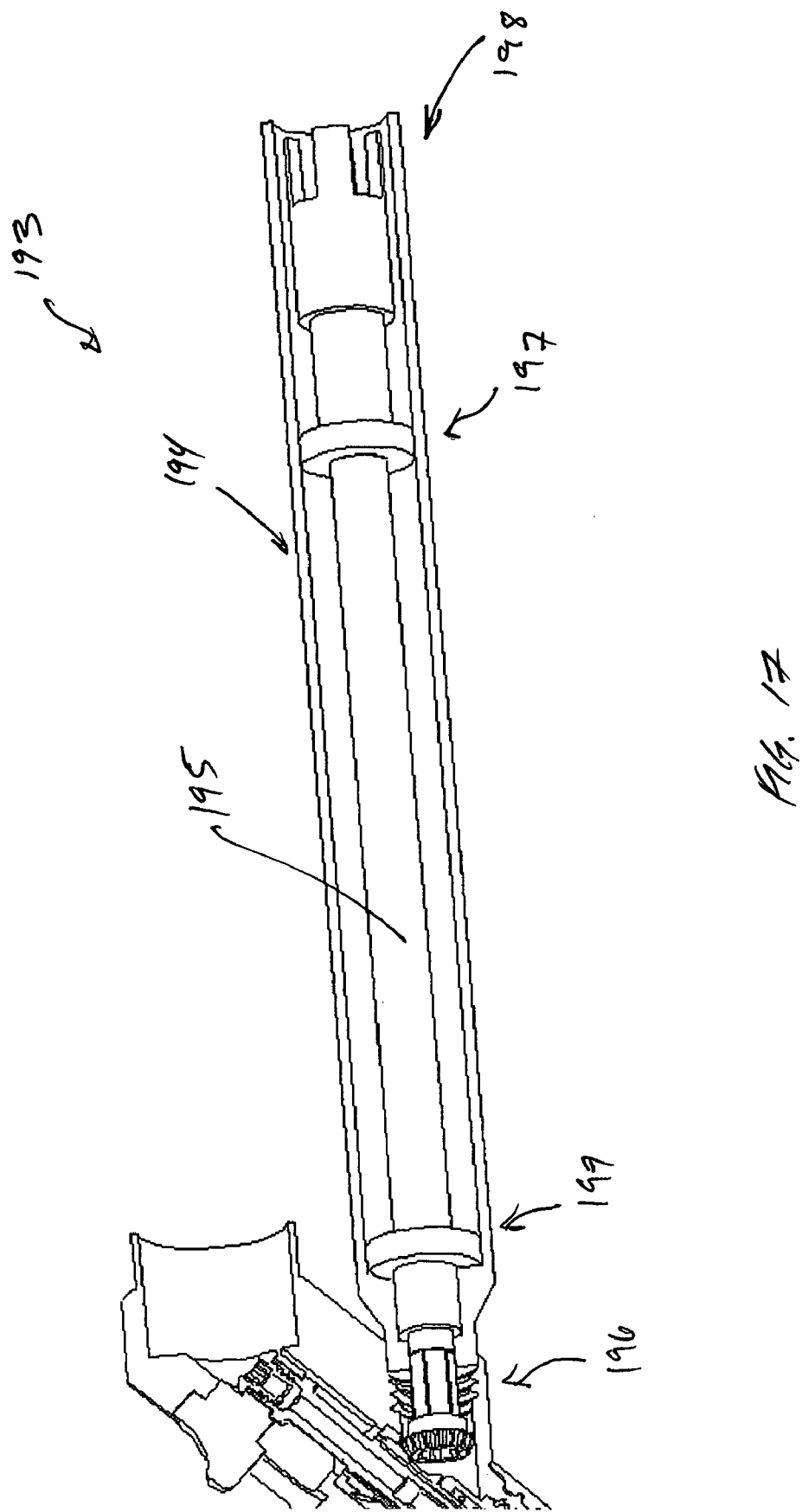
FIG. 17 is a schematic perspective sectional view of the gear system of FIG. 15.

FIG. 15 illustrates a motorized component of one embodiment of the handpiece 102. As shown in FIGS. 16-17, the motorized mechanism 182 comprises a motor 184. The motor size is relatively small and configured to fit within the handpiece 102. The motor 184 preferably comprises a rotating or oscillating portion 186. The rotating or oscillating portion 186 can have prongs configured to cooperate with prongs of a connector 193. The prongs of portion 186 allow for a quick connection and disconnection of the motor 184 and the connector 193. Accordingly, the motor 184 can be removed from the handpiece 102. The rotation of the motor 184 preferably is translated to the shaft or connector 193. The connector 193 has a gear connector housing 194, a shaft 195, a mating gear 196, one or more ball-bearings 197, and a quick connect/disconnect tip 198 for translating the rotation or oscillation to the tool holding or gripping mechanism 192. Gear connections 188 between the connector 193 and the tool gripping mechanism 192 can be optimized to reduce noise and improve performance of the handpiece 102. The gears can be coated with a coating, such as an amorphous diamond coating and/or a ME-92 coating, to minimize frictional losses. The controls for the device are preferably located in a convenient position for single handed function. The motorized mechanism 182 can be configured in some embodiments to operate the tool gripping mechanism 192, the dispensing mechanism 105, or both.

In the illustrated embodiment, the system 100 is configured such that the tool 104 may be used to penetrate tissue at an injection site and deliver solution from the cartridge 106 to the injection site through application of the solution dispensing mechanism. The handpiece 102, in turn, is configured to control the rate of delivery of the solution precisely and safely from the cartridge 106 and through the tool 104 to the patient. For example, the solution dispensing mechanism can be controlled to adjust the delivery of the solution. In one embodiment, the system is configured to rotate, vibrate and/or oscillate the tool 104 relative to the cartridge 106. For example, the tool 104 may rotate and/or oscillate to perforate tissue while the cartridge 106 is held generally stationary within the handpiece 102. In other particularly preferred embodiments, the tool 104 may rotate and/or oscillate to perforate tissue while the cartridge 106 generally rotates and/or oscillates the ampoule continuously or intermittently within the handpiece 102. In some embodiments, the tool 104 can be held generally stationary.

In one embodiment, the tool 104 punctures the ampoule 106 to place the tool 104 in fluid communication with the cartridge 106. The tool 104 preferably punctures the ampoule 106 when the tool 104 is inserted into the tool gripping mechanism by the carrier. In other embodiments, the tool 104 is directly or indirectly coupled to the cartridge 106 to place the cartridge 106 in fluid communication with the tool. As mentioned above, one advantage of using the tool 104 to puncture the cartridge 106 includes minimizing the number of fluid delivery components between the cartridge 106 and the delivery site. Minimizing components preferably avoids leakage at joints and simplifies the manufacturing and assembly process. Additionally, another advantage of minimizing components between the cartridge 106 and the delivery site is that fewer components allow the overall drive train to become smaller.

In some embodiments, the intraosseous injection system 100 the handpiece 102 is configured to be cordless (e.g., battery operated). In some embodiments, the handpiece 102 is configured to have a fiber optic light to bring additional illumination to the operating area and or curing light systems to facilitate dental applications. The handpiece 102 can have a light-weight ergonomic design by making the handpiece out of titanium alloy and or incorporating ceramic balls instead of stainless steel balls with cordless motor controls. In some embodiments, the system may be configured to oscillate the tool 104 instead of rotating the tool 104. Oscillating the tool 104 may reduce the torque generated during bone perforation as compared to rotation. For example, a quarter turn rotation of the tool 104 reduces the torsional overloading on the tool 104 and minimizes the chances of tool failure. Oscillating the tool 104 also allows for a smaller sized tool to be used, compared with tools used for full rotation applications. Using a smaller tool size advantageously reduces the pain caused by injection of the tool 104 into the patient.

Figure 18:
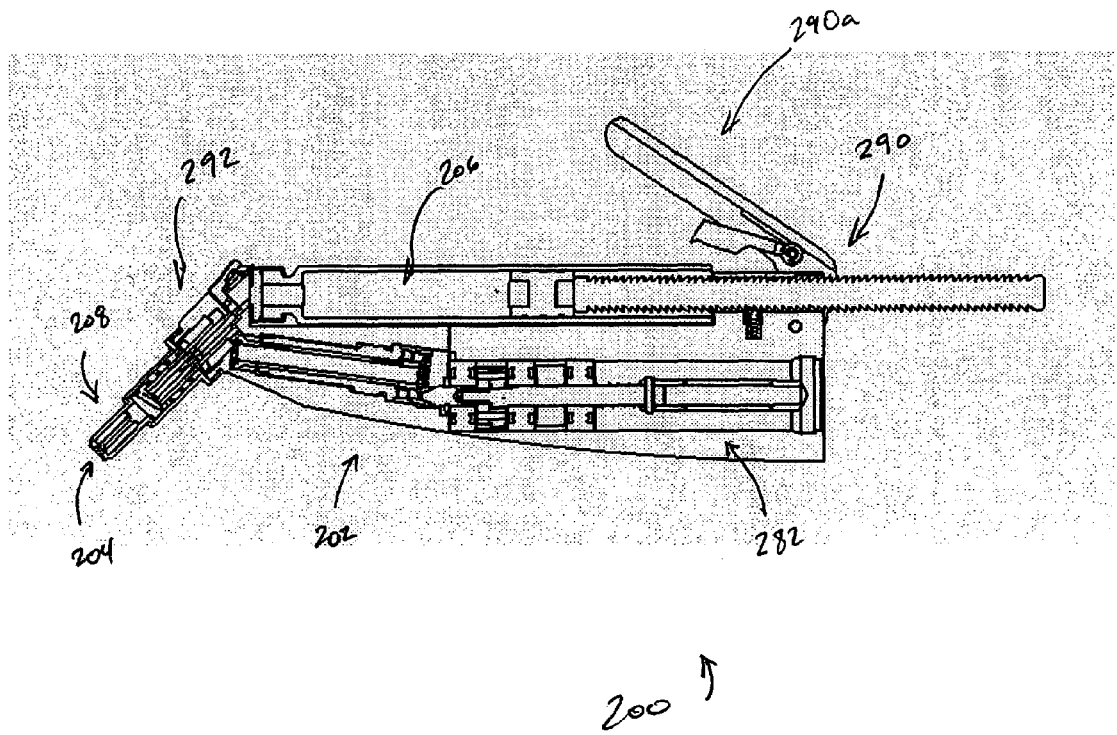
FIG. 18 is a schematic sectional view of another embodiment of an injection system having a handpiece, a tool, a tool actuating mechanism, a protective sleeve, and a dispensing mechanism.

FIG. 18 is a cross-sectional view of another embodiment of an injection system 200. The system 200 comprises a handpiece 202, a tool 204, a cartridge 206, and a sleeve 208. System 200 has a motorized mechanism 282, a dispensing mechanism 290, and a tool gripping mechanism 292. The system 200 is similar to system 100 described above, except that the dispensing mechanism 290 has a gear rack and a spring-loaded lever assembly 290a for advancing the gear rack forward in a ratchet type motion. The mechanism 282 can be a rotating mechanism and can be configured to be connected to an off the-shelf or customized motor. The motor can be, for example, an air motor (e.g. an air supply) or electric motor. It will be understood by those skilled in the art that the present invention extends beyond the specifically disclosed embodiments described above to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various substitutions, combinations or subcombinations of the specific features and aspects of the embodiments described above may be made and still fall within the scope of the invention. In particular, some additional features and functions of intraosseous injection systems will now be described in detail below.

A. Tools

1. Needles

Figure 19:
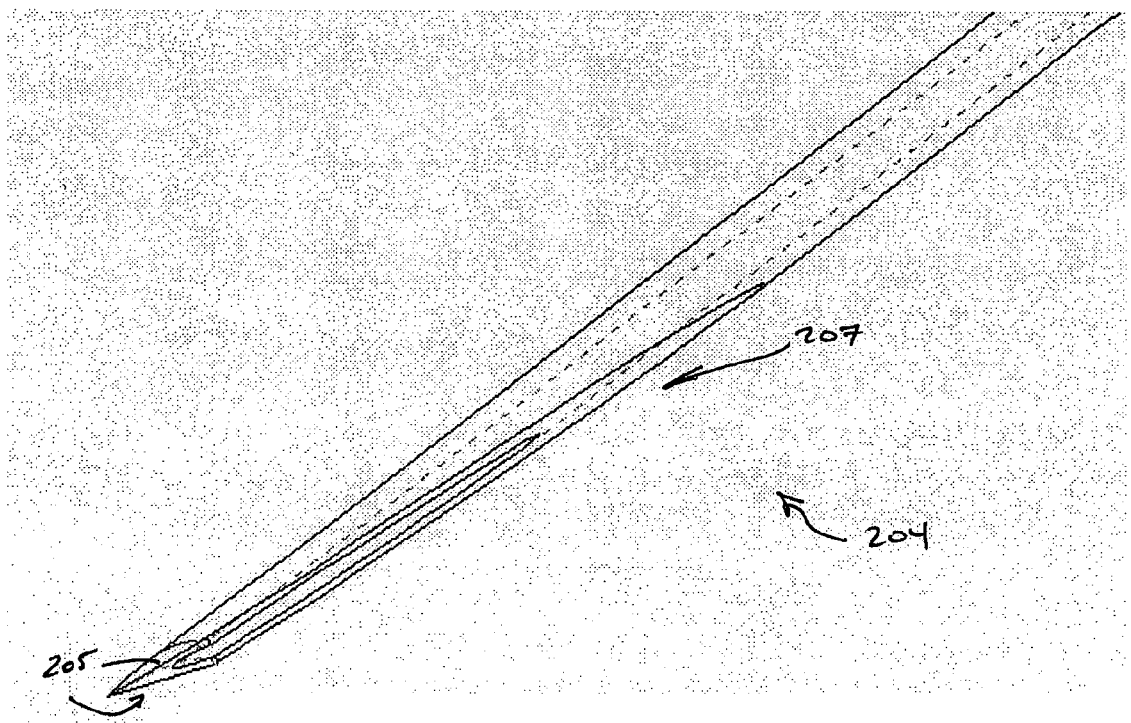
FIG. 19 is a perspective view of one embodiment of the tool of FIG. 18, having dual cutting surfaces, a bore, and an angled shaft.
Figure 20:
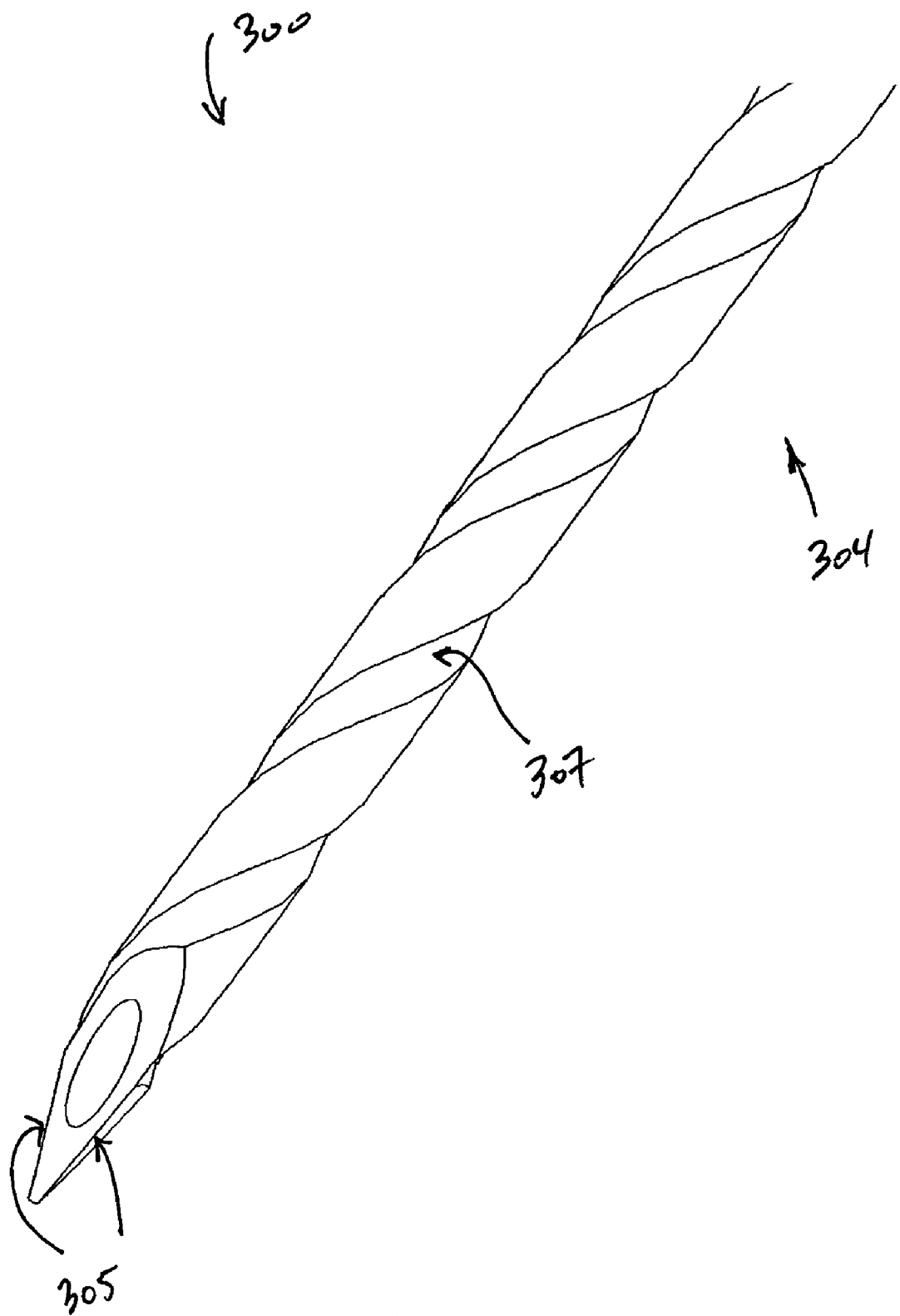
FIG. 20 is a perspective view of another embodiment of a tool for an injection system, having flutes.

As shown in FIG. 19, in another embodiment, the tool 204 is a needle designed with a double cutting edge 205 for left and right handed cutting. The needle 204 can have a steeped secondary angle 207. The steeped secondary angle 207 reduces frictional forces and minimizes pain caused by insertion. As shown in FIG. 20, in another embodiment of an injection system 300, a tool 304 has a needle with a double cutting edge 305 and a fluted outer surface 307.

Figure 21:
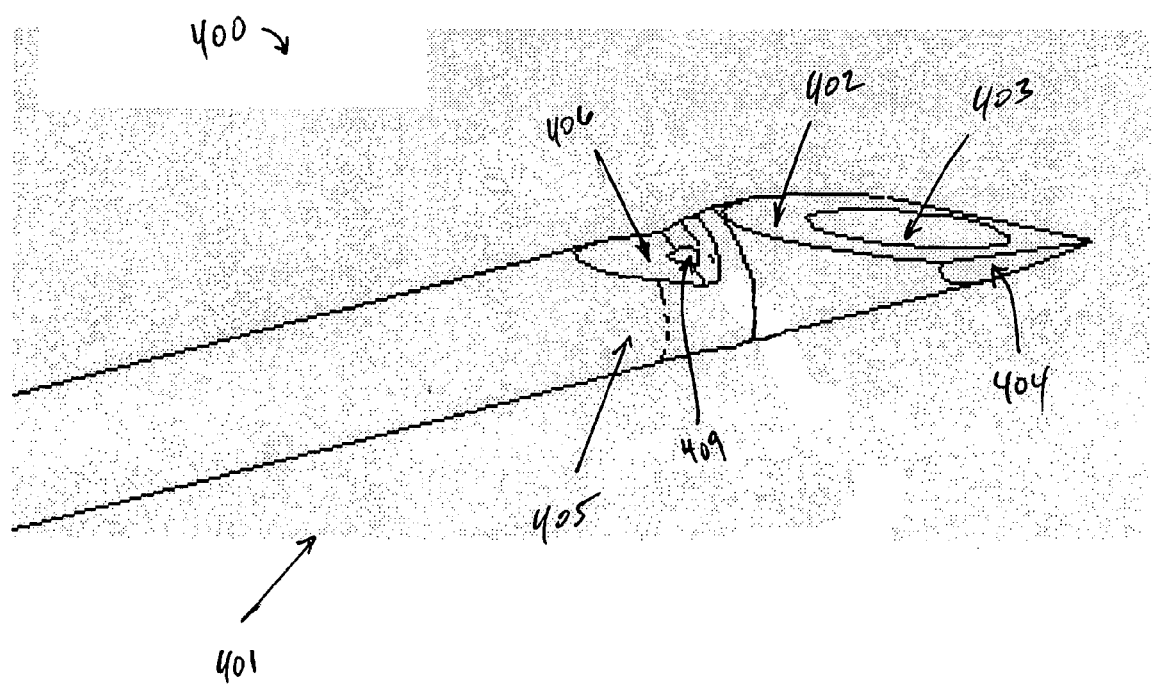
FIG. 21 is a perspective view of another embodiment of a tool for an injection system, having a notch.
Figure 22:
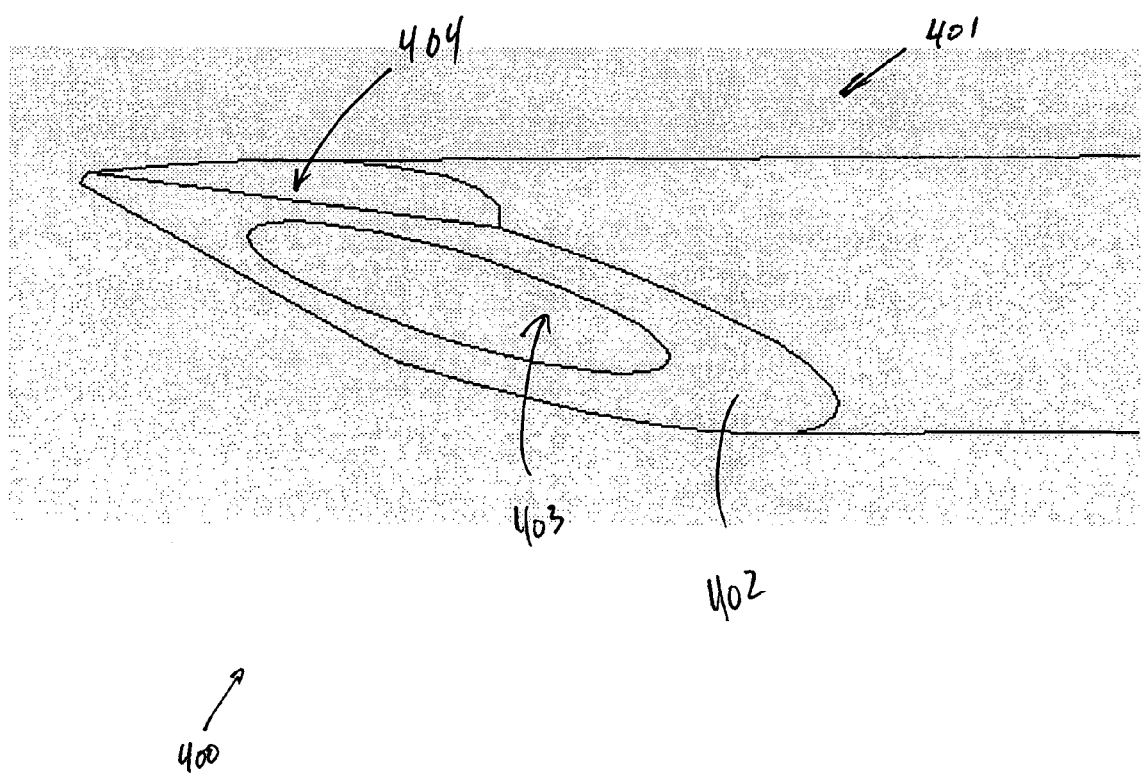
FIG. 22 is a perspective view of a pointed tip of the tool of FIG. 21.
Figure 23:
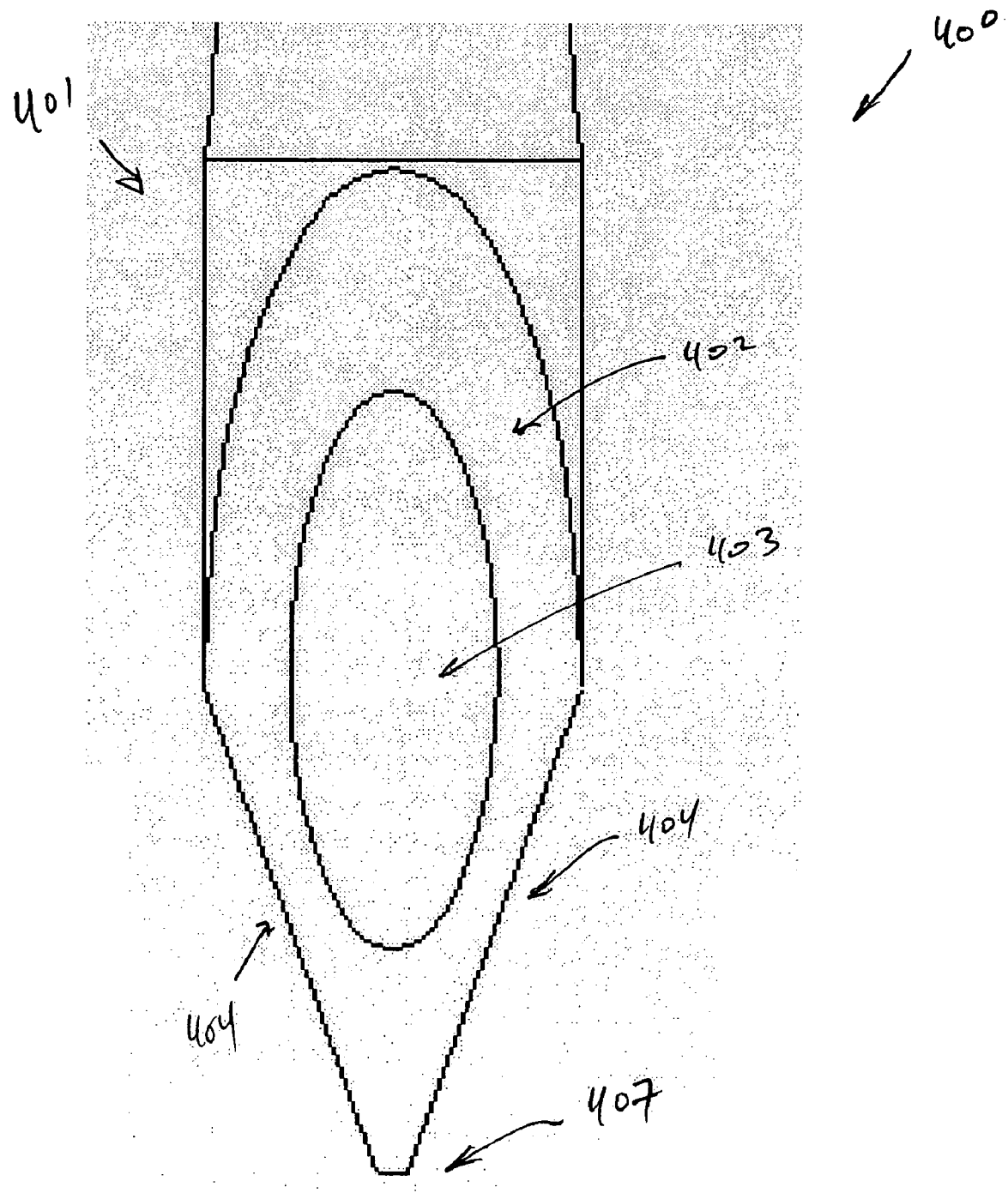
FIG. 23 is a side view of the pointed tip of the tool of FIG. 21.
Figure 24:
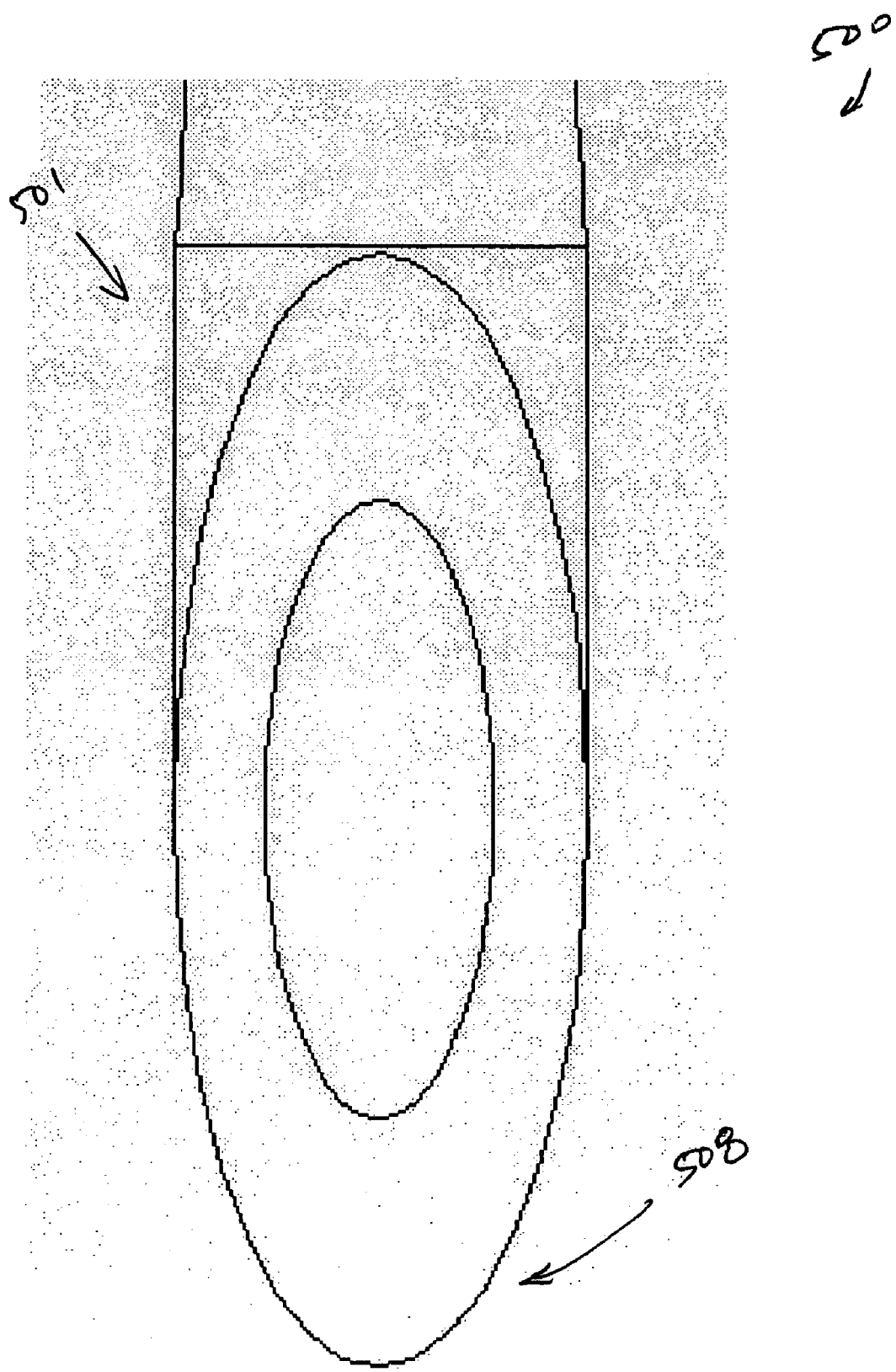
FIG. 24 is a side view of another embodiment of a tool for an injection system, having a rounded tip.
Figure 25:
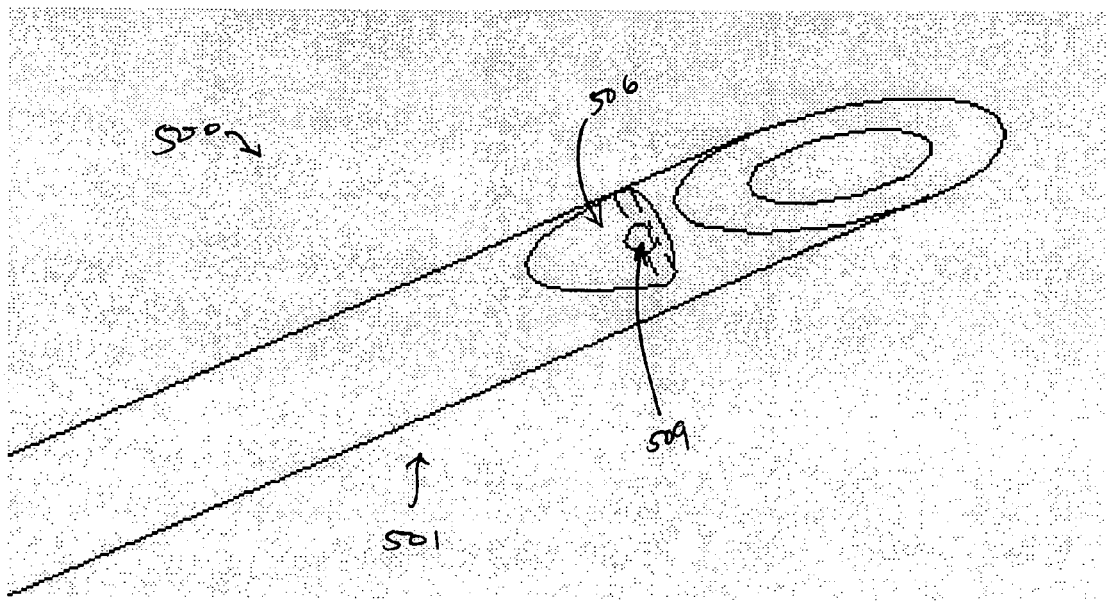
FIG. 25 is a perspective view of the tool of FIG. 24.
Figure 24:
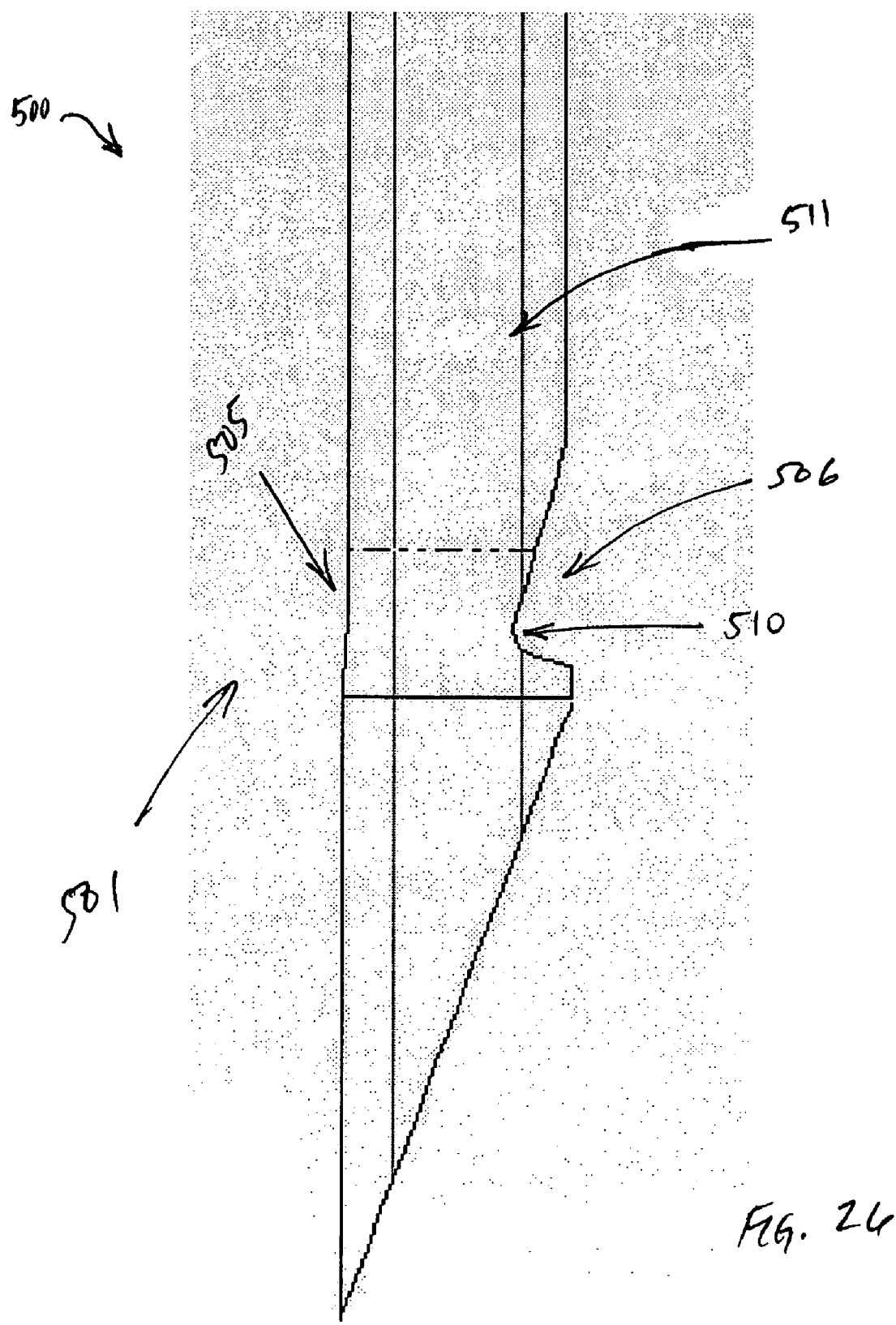
Figure 27:
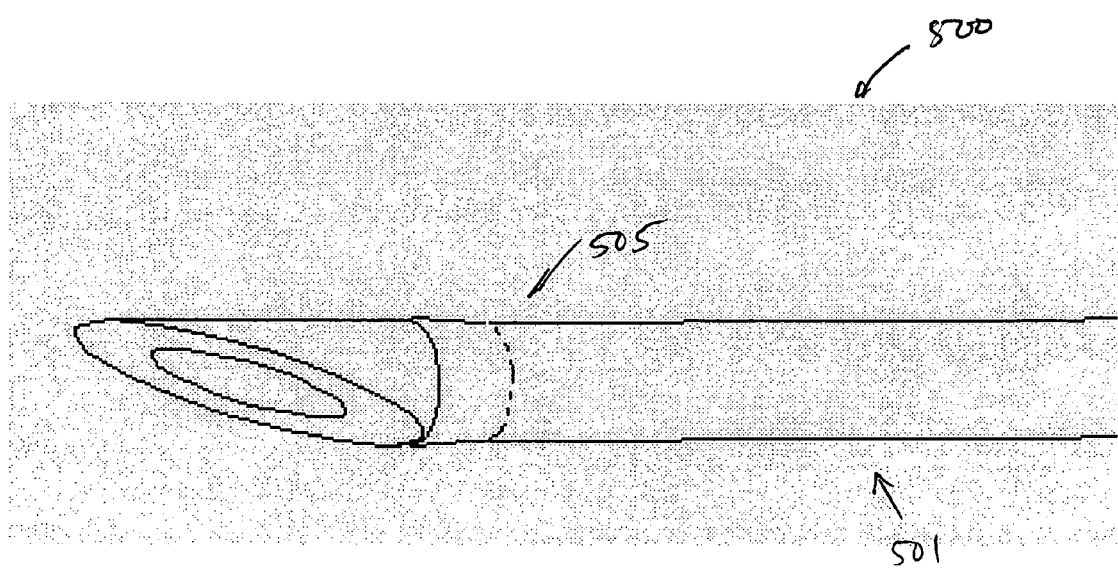
FIG. 27 is another perspective view of the tool of FIG. 24, showing a radial relief portion.

FIG. 21 shows an intraosseous injection system 400 having a needle 401 having a needle tip with a bevel 402, which creates an opening 403. It also has one or more cutting edges 404, a radial relief 405, and one or more notches 406. FIG. 22 is a perspective view of the tip of the needle 401 showing cutting edges 404. The cutting edges 404 allow for an easier penetration of the needle 401 into the bone as the needle 401 is rotated or oscillated. FIG. 23 is a side view of the tip of the needle 401 showing the cutting edges 404. The cutting edges 404 create a narrow tip 407 in comparison with a rounded tip 508, of another embodiment of an injection system 500, having components similar to the components of system 400, as shown in FIG. 24. This narrow tip 407 reduces the downward force required for the needle 401 to penetrate into the site. FIG. 25 is a perspective view of the needle 501 shown in FIG. 24. In systems 400, 500, notches 406, 506 create orifices 409,509, which provide a way to discharge medication away from the cutting action. The needles 401, 501 may have one or more notches 406, 506. The notch shape can be any suitable shape. The depth 510 of the notch 506, as shown in FIG. 26, preferably penetrates the through hole 511 of the needle 501. The notch 406, 506 can have any suitable radial and linear location. The notches 406, 506 preferably are positioned so that the openings are not likely to be clogged by bone chips. As shown in FIG. 27, the needle 501 can have a radial relief 505 to reduce heat buildup and to, for example, reduce the likelihood of the needle 501 getting stuck in the bone. In some embodiments, a standard needle tip can also be used. In some embodiments a standard needle can be used for soft tissue injection. In some embodiments the handpiece can be configured to allow for soft tissue injection as well as hard tissue injection. In one embodiment, an extended cut is not provided so that anesthetic solution is delivered into the soft tissue at the earliest possible stage.

Figure 27A:
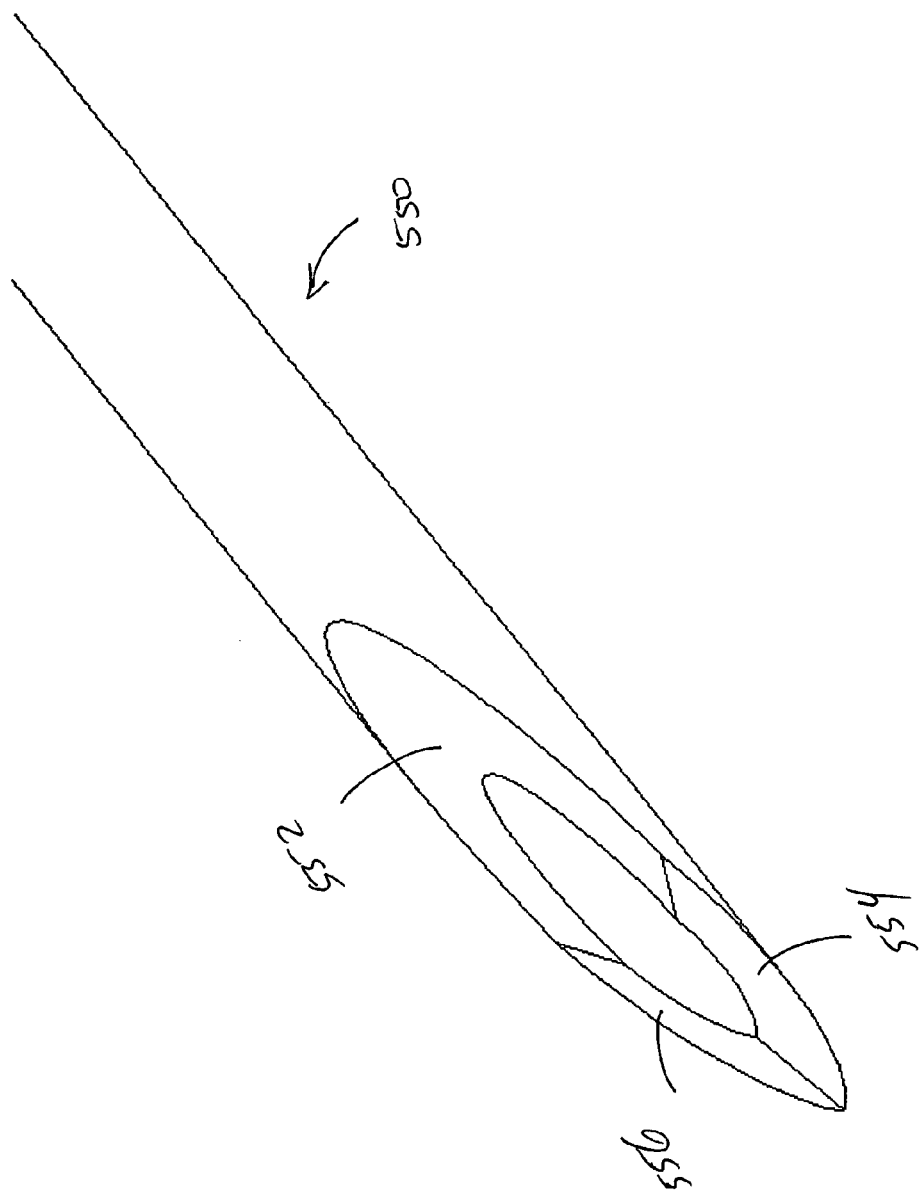
FIG. 27A is a perspective view of another embodiment of a tool.

Accordingly, in one embodiment, a needle tip has one or more anesthetic outlet notches, one or more cutting edges, and a radial relief. The tip has cutting edges to facilitate cortical plate penetration when needle is rotated or oscillated while preventing overheating conditions. The notch creates an opening located away from the cutting tip, which prevents clogging of the needle. In some embodiments, a radial relief portion is provided to reduce frictional forces that cause heating of the needle during bone penetration. In another embodiment, a steeped secondary angle reduces frictional forces and minimizes pain caused by insertion. Accordingly, in one embodiment, the needle tip can be used to penetrate the soft tissue and/or the bone and deliver anesthetic solution all in one device without causing extreme complications. The needle facilitates penetration into cortical plate, prevents clogging of the needle, and reduces frictional forces that cause overheating of bone and needle. In another embodiment, the needle tip 550 has bevels to penetrate the soft tissue and the bone and deliver anesthetic solution all in one device without causing extreme complications as shown in FIG. 27A. The needle tip 550 has a primary bevel 552 and two (right 554 and left 556) secondary bevels).

In operation one uses the needle device in a normal approach for intraosseous injection applications. First, the needle is inserted into the gingival mucosa and anesthetic solution may be applied to numb the area. Secondly, the needle is rotated, oscillated, and/or left static to penetrate the cortical plate to the desired depth. The rotation or oscillation of the needle may also be started before or during the penetration of the gingival mucosa. Then, the anesthetic solution is injected. Finally, the needle is removed from the site and disposed in an appropriate receptacle.

Accordingly, one embodiment of the needle design comprises a tip that has left-handed and/or right-handed cutting edges to facilitate cortical plate penetration. Alternately the needle tip may have one or more bevels to facilitate the soft tissue and cortical plate penetration. The needle tip preferably has an inwardly tapering outer diameter or a steeped secondary angle to reduce the risk that the needle will jam into the bone and to facilitate bone-drilling action by reducing frictional forces. The needle body preferably has one or more notches to ensure delivery of anesthetic solution. The needle body preferably has a radial relief to reduce heat buildup and to prevent clogging of anesthetic outlets during bone drilling. The needle can be coated with a coating, such as an amorphous diamond coating and/or a ME-92 coating, to reduce the coefficient of friction on the surface of the needle.

2. Files, Burrs, Drills

Figure 28:
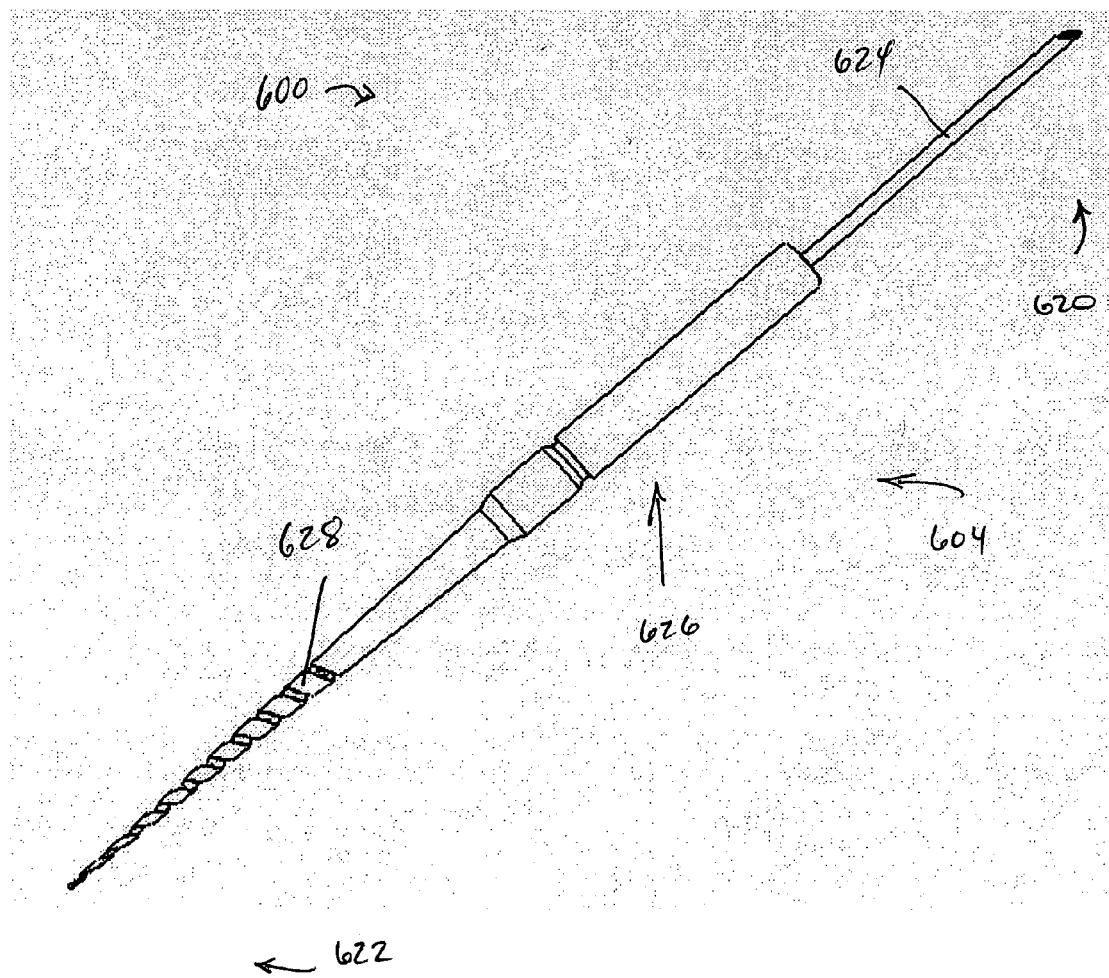
FIG. 28 is a perspective view of another embodiment of a tool for an injection system, having flutes, a hub, and a proximal cartridge-insertion portion.
Figure 29:
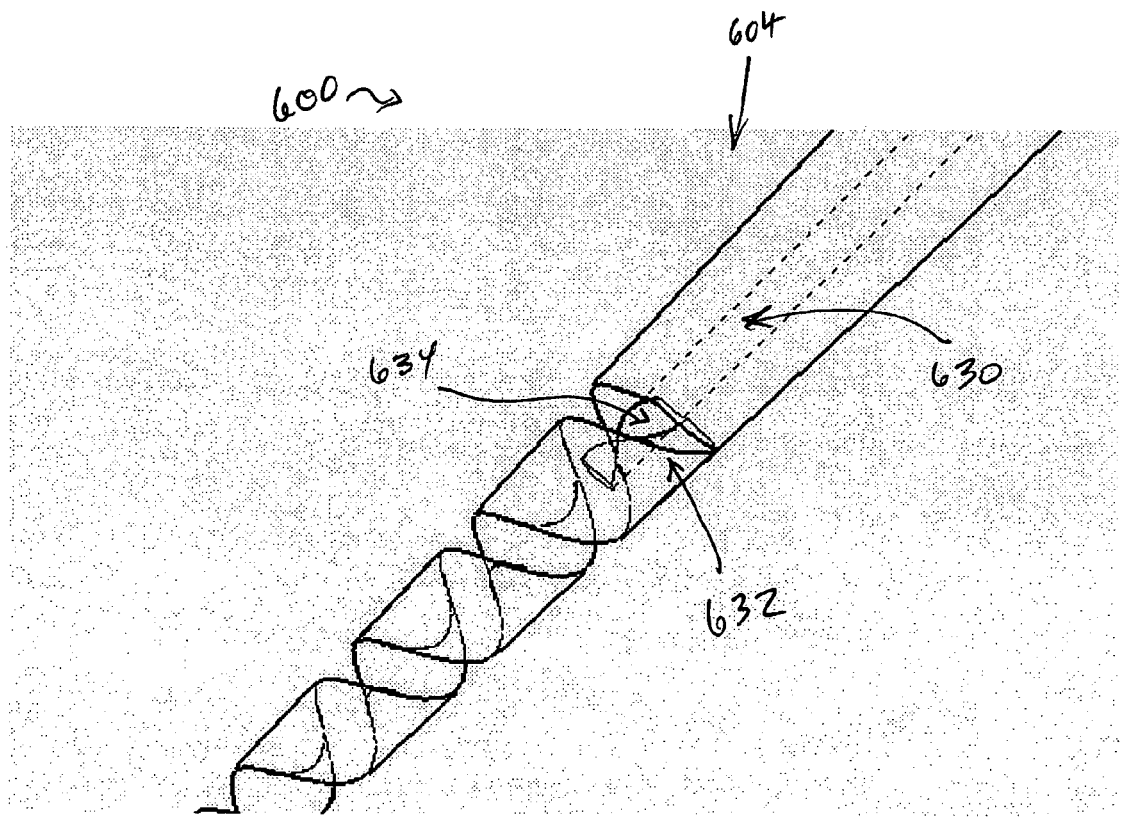
FIG. 29 is an enlarged perspective view of the tool of FIG. 28.

As shown in FIGS. 28-29, in another embodiment of an injection system 600, a tool 604 is a file, burr or drill. The tool 604 has a proximal end 620 and a distal end 622. The proximal end 620 of the tool 604 can be configured to penetrate a cartridge containing a solution, e.g., an anesthetic solution, antibiotics, an irrigation solution, composite, filling materials, gutta-purcha, and/or other dental materials. For example, the proximal portion 620 can have a needle or hollow tube 624 at its proximal end to allow for the dispensing of solutions, pastes, or gels from a cartridge. In one embodiment, the solution, paste, or gel is advantageous for treating the socket of the tooth or a root canal space being created by the tool 604.

In one embodiment, the solution, paste, or gel is advantageous to irrigate the tool and/or tooth structure to avoid overheating of the tool and the site. The tool 604 has an irrigation feature and can be used with any suitable handpiece. For example, the tool 604 can have a chuck and/or a latch connection to fit some handpieces.

The tool 604 can comprise multiple pieces. As shown in FIG. 28, the tool 604 has a fluted distal end 622 and a hub portion 626. In some embodiments, the tool 604 is a unitary structure. In the illustrated embodiment, the tool 604 is a multi-piece structure, with the hub 626 coupled to the fluted body 628. In some embodiments, the hub 626 can be press-fitted or laser welded to the fluted body 628. The proximal portion 620 of the needle 604 can be integral with the needle body 628 or hub 626 in some embodiments. In other embodiments, a proximal portion 620 of the needle 604 can be a tube 624 or other structure that is press fitted, laser welded, or otherwise coupled to the body 628 or hub 626.

As shown in FIG. 29, the tool 604 has an irrigation hole 630. The depth of the irrigation hole 630 can vary depending on the design of the file, burr or drill. In one embodiment, the file, burr or drill has an irrigation hole 630 that protrudes through the flute 632 at the proximal end of the flute. In another embodiment, additional side holes perpendicular to, or at an angle to, the long axis of the irrigation hole 630 are provided. When the proximal end 620 of the file, burr or drill with the irrigation feature is inserted into a cartridge mounted in the handpiece and the dispensing mechanism is activated, the solution will go into the irrigation hole 630, will come out of an opening 634 and will trickle or slide down the flutes 632 to treat and/or cool down the site and/or the file, burr or drill.

Figure 30:
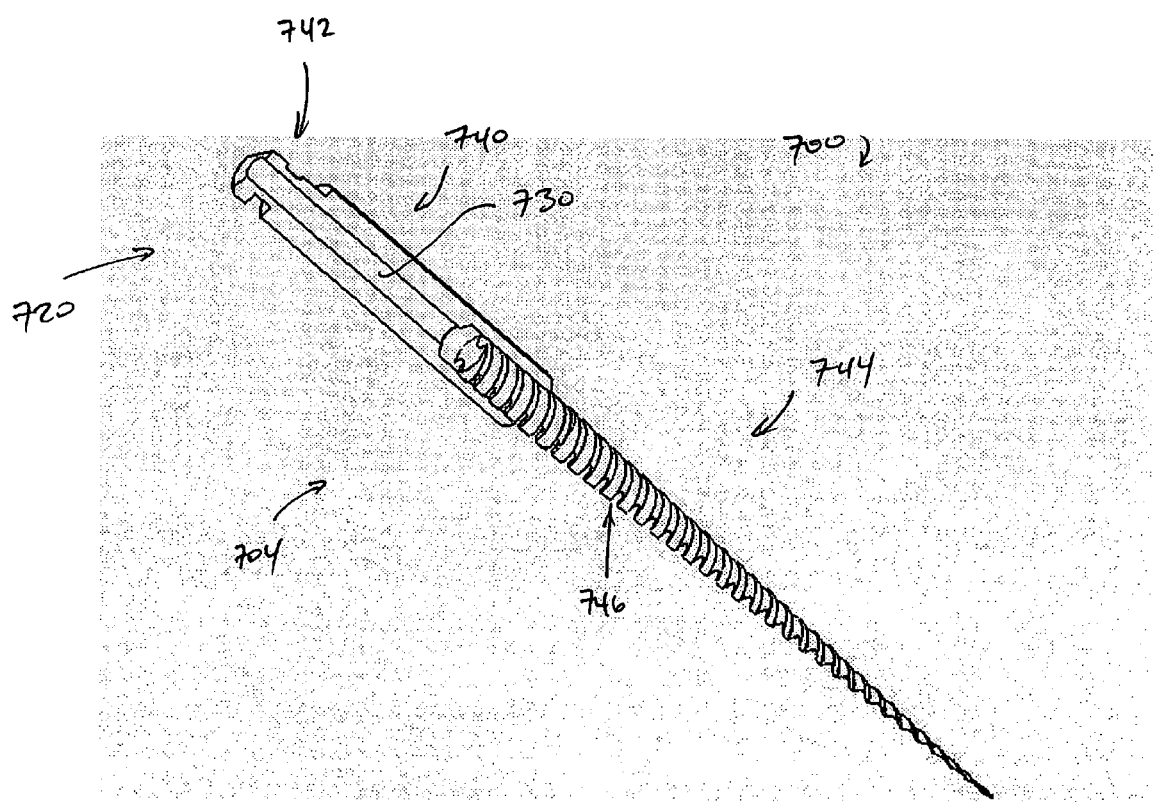
FIG. 30 is a perspective, partial sectional view of another embodiment of a tool for an injection system, having flutes, a hollow shank portion, and a proximal connection portion.
Figure 31:
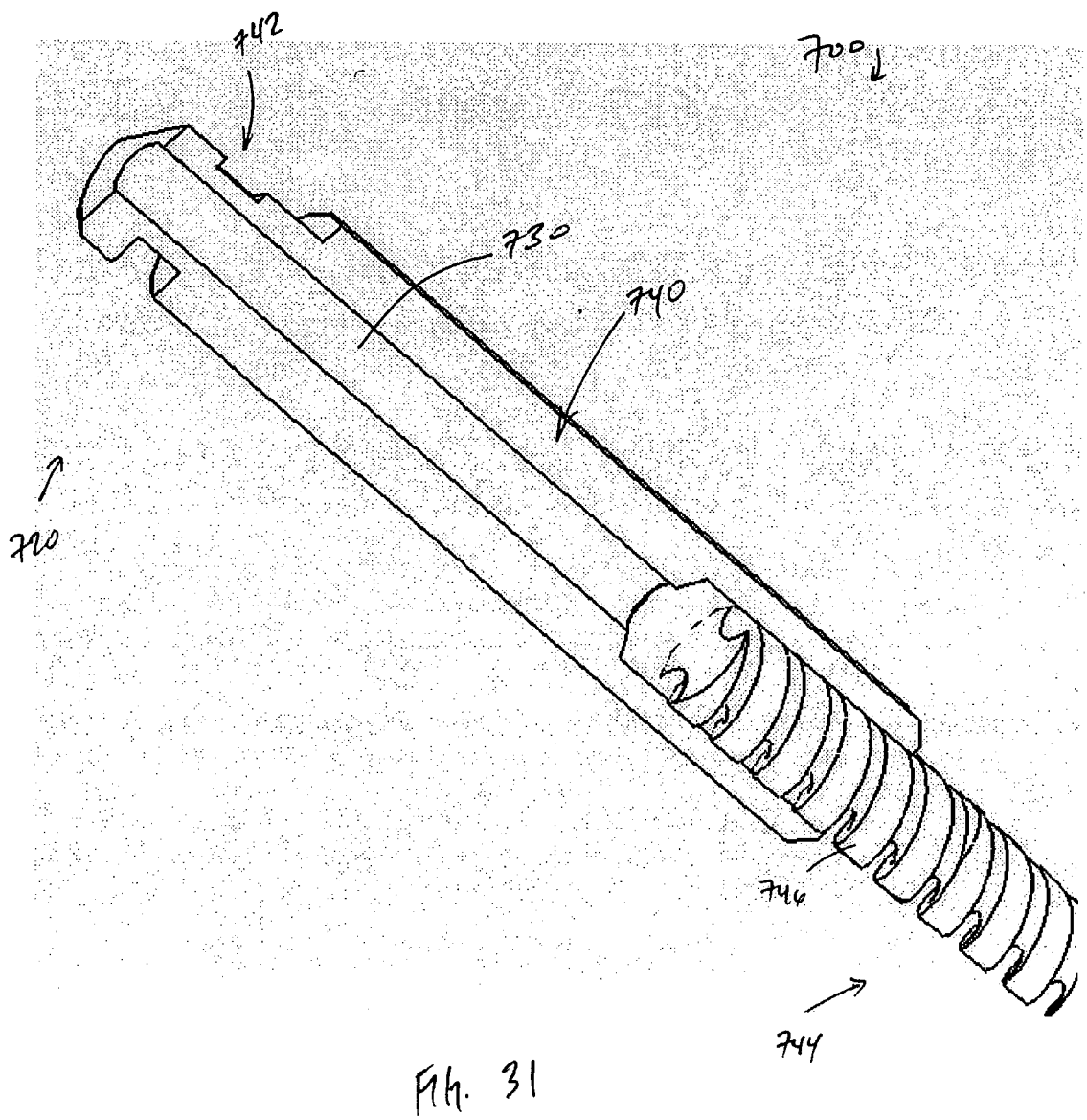
FIG. 31 is an enlarged perspective, partial sectional view of the tool of FIG. 30.
Figure 32:
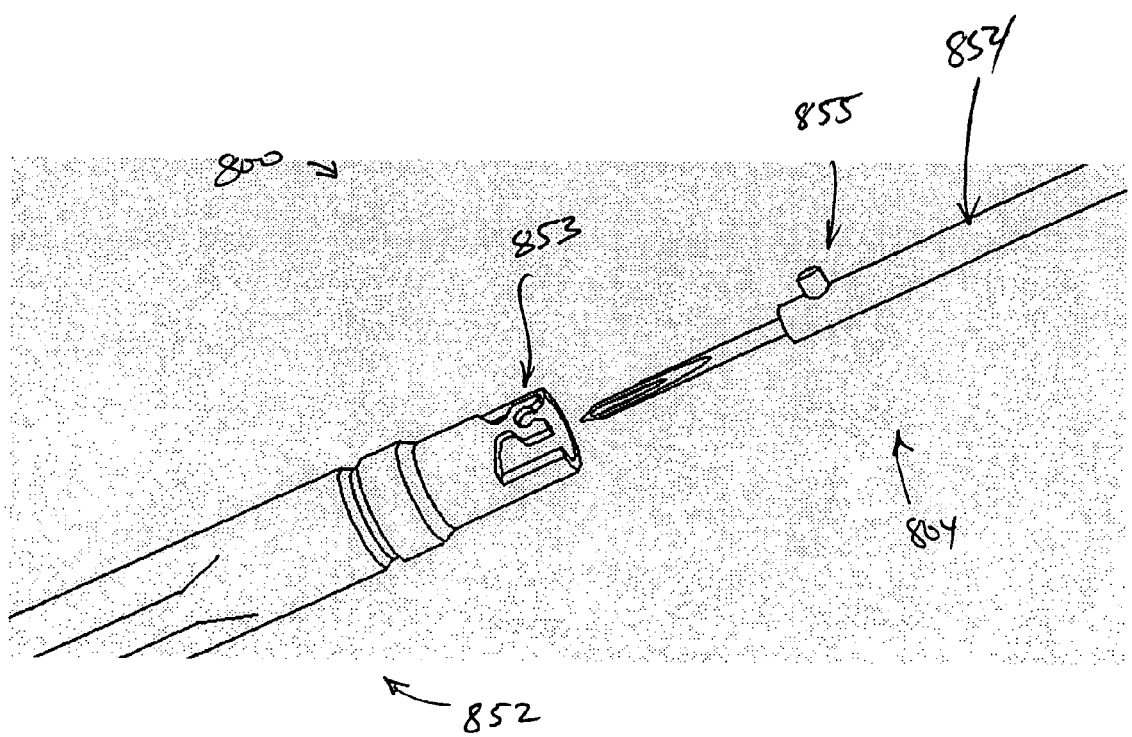
FIG. 32 is a perspective view of one embodiment of a tool and tool carrier combination for an injection system.
Figure 33:
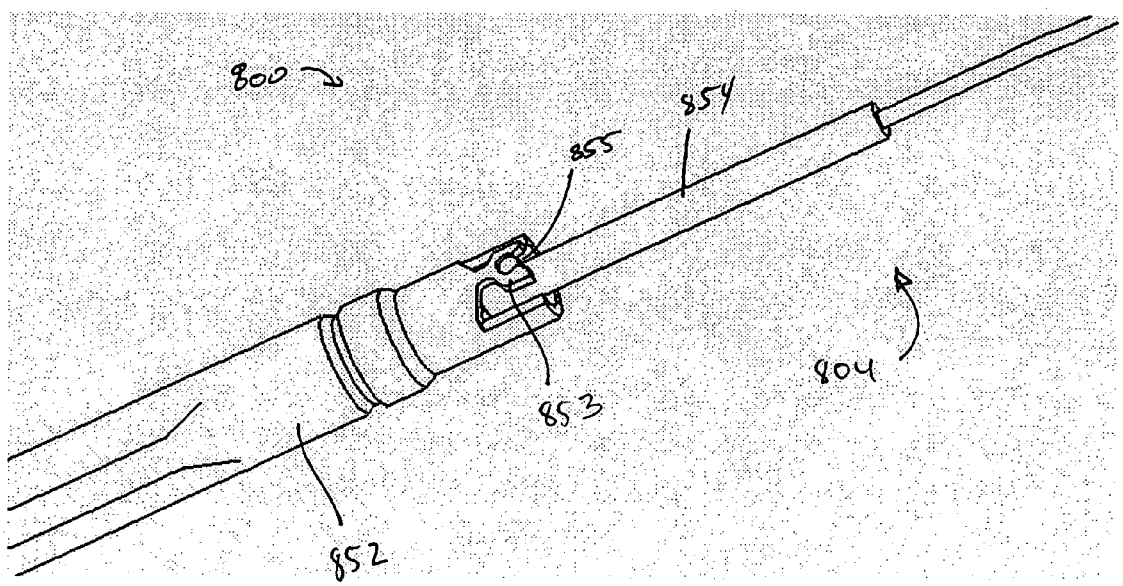
FIG. 33 is a perspective view of the tool and tool carrier combination of FIG. 32, showing a hub of the tool coupled with the tool carrier.

In another embodiment of an injection system 700 is shown in FIGS. 30-31, a tool 704, e.g., a file, has a shank 740 with an irrigation hole 730. The tool 704 has a latch connection 742 to fit one or more types of handpieces. The file body 744 has flutes 746 that cover a length of the file body 744. The file body 744 is press-fitted, laser welded, or otherwise coupled to, or unitarily formed with, the shank 740. There can be one or more flutes 746. The flutes 746 can vary in shape. The flutes 746 can have a pitch that is particularly suitable for a desired application. A tube or needle, not shown, can be coupled to, or integrally formed with, the proximal end 720 of the shank 740. The tube or needle preferably can be coupled with a dispensing device or cartridge. In another embodiment, the tube or needle can be a part of the shank body. In use, solution, antibiotics, gel, and/or paste goes through the hole 730 and into the flutes 746 of the file 704.

B. Handpieces

1. Needle Holding Mechanisms

FIGS. 32-38 show one embodiment of an injection system 800, wherein a tool 804 is carried and loaded into a housing of a handpiece with a carrier 852. The carrier 852 can also be used to unload the tool 804 from the handpiece 802 (only a portion of which is illustrated in FIGS. 32-38). As described above, the tool 804 preferably is held within the housing 820 of the handpiece 802 by a collet 824, a chucking, and/or a quick connection mechanism 825 that provides for the movement of the tool 804, e.g., rotation and/or oscillation of the tool 804.

The tool preferably has a protrusion 855 on the hub portion 854. The carrier 852 has a coupling portion 853, e.g., a clip, for coupling the carrier 852 with the tool 804 at the protrusion 855. The user can hold the carrier 852 to bring the tool 804, e.g., a needle, a hollow drill, and/or a file, into the handpiece 802. The hub 854 of the needle 804 can be gripped by the collet 824 or chucking mechanism of the handpiece 802 in some embodiments. In the illustrated embodiment, the protrusion 855 preferably engages the quick connect/disconnect mechanism 825. The carrier 852 is then uncoupled from, e.g., clipped off of, the hub 854. The tool can be rotated or oscillated as anesthetic solution is dispensed through the tool 804. Once the application is completed, the end user can engage the carrier 852 back onto the protrusion 855. The user opens up the collet 824, the chucking mechanism, and/or the quick connect/disconnect mechanism 825. The needle and hub assembly 804 can then be removed from the handpiece 802.

Figure 34:
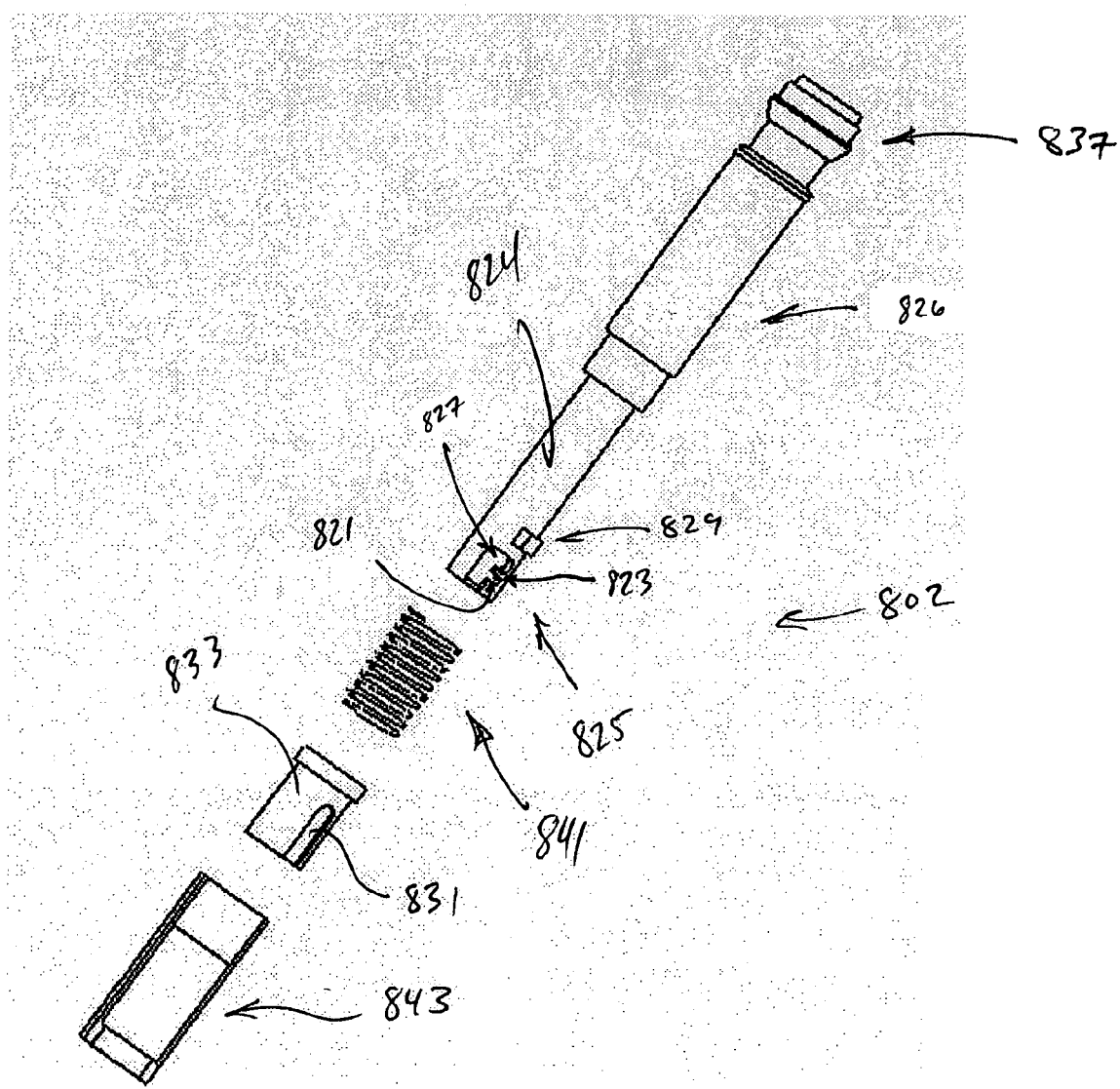
FIG. 34 is an exploded perspective view of one embodiment of a tool connection and actuation system for an injection system handpiece.

As shown in FIG. 34, in one embodiment, the quick connect/disconnect mechanism 825 has a distal end with an "L" shape opening 827 and a guiding feature or tab 829 to align an opening 831 of a retaining ring 833 to the radial portion of the "L" shaped opening 827 (short leg of the "L" shaped opening 827). The collet housing 826 has gear teeth 837 at its proximal end to engage a gear shaft of a motor, or air driven mechanism to rotate or oscillate the collet 824. A spring 841 allows for the retaining ring 833 to be pushed proximally by the carrier 852 and automatically retract when the carrier 852 is withdrawn. The retaining ring 833 prevents the hub 854 from rotating during use. A capping sleeve 843 preferably holds the retaining ring 833 in place.

Figure 35:
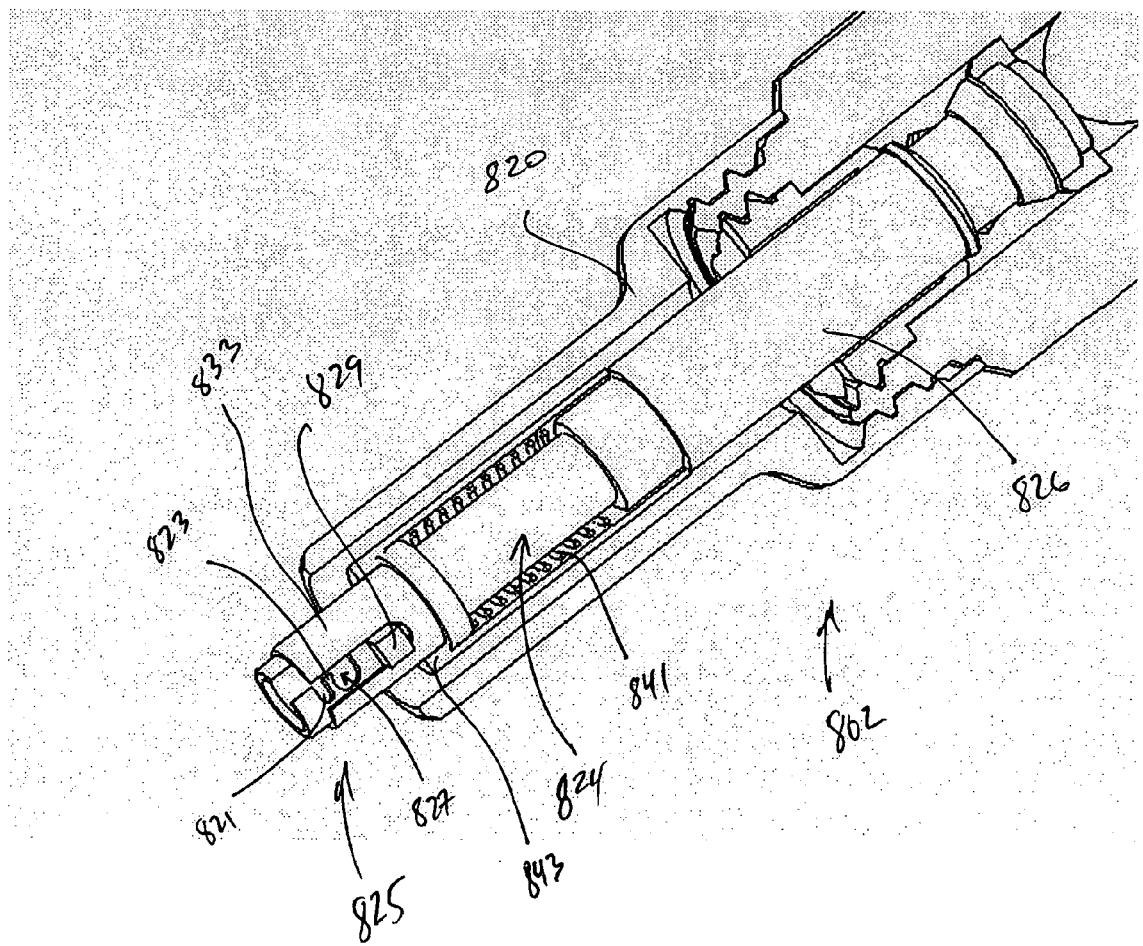
FIG. 35 is an enlarged perspective, partial sectional view of the tool connection and actuation system of FIG. 34.
Figure 36:
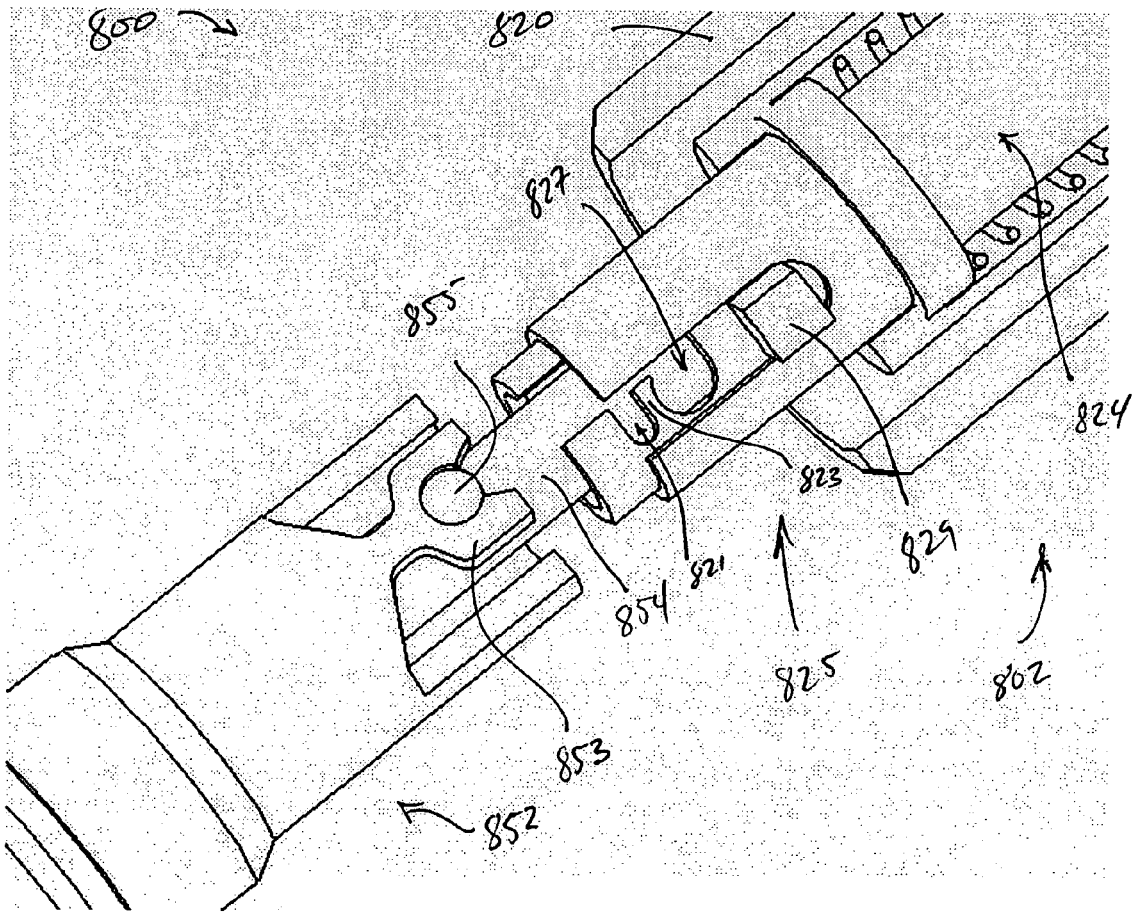
FIG. 36 is an enlarged perspective, partial sectional view of the tool and tool carrier combination of FIG. 32 cooperating with the tool connection and actuation system of FIG. 34 for insertion of the tool into the handpiece.
Figure 37:
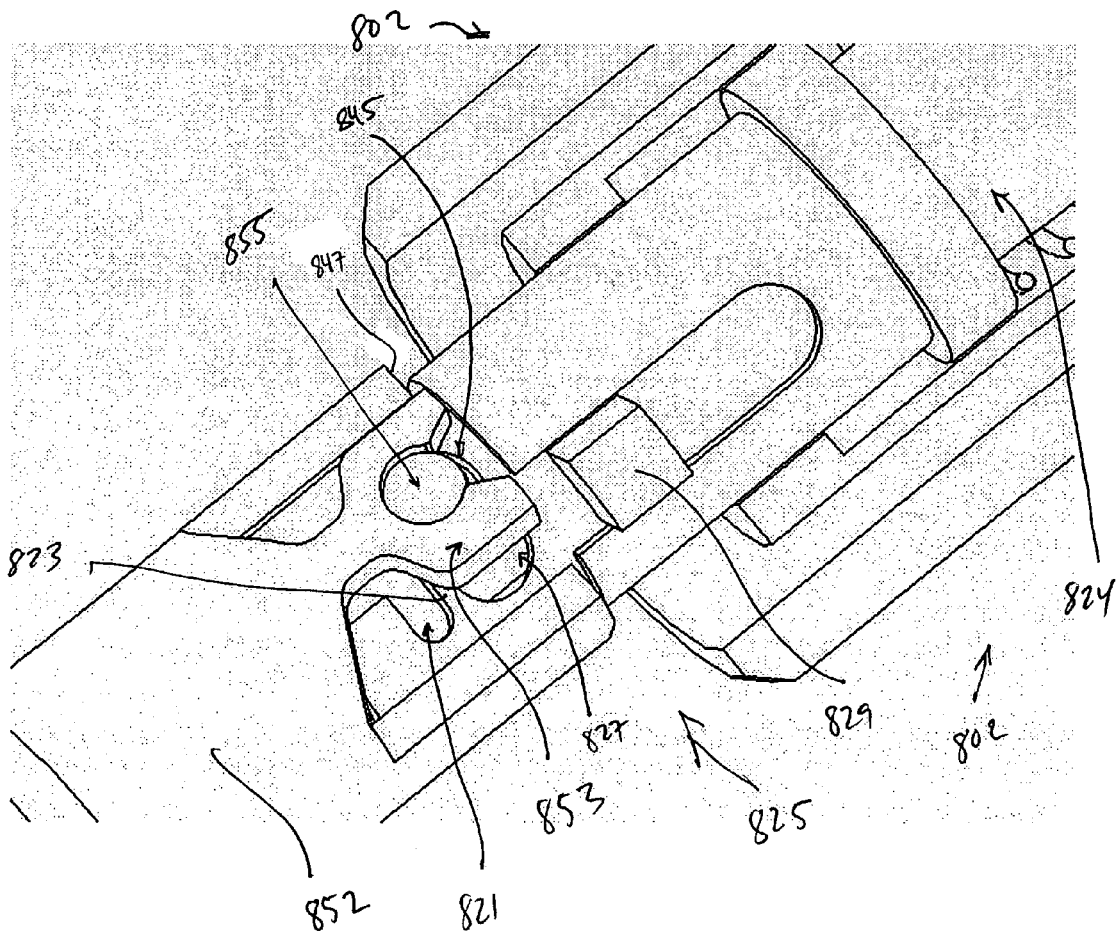
FIG. 37 is an enlarged perspective, partial sectional view of the tool and handpiece of FIG. 36, showing the tool being inserted into a slot of the handpiece.
Figure 38:
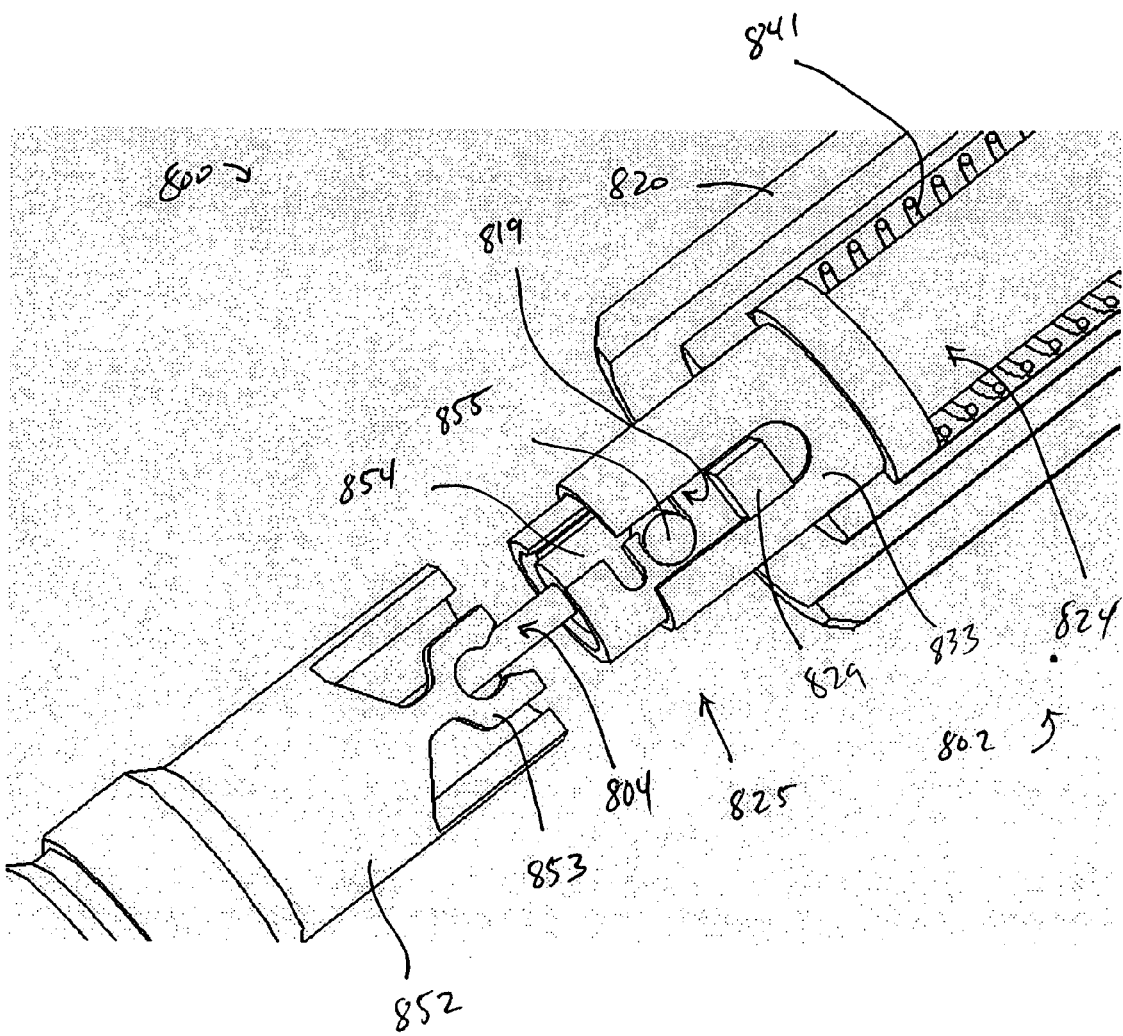
FIG. 38 is a an enlarged perspective, partial sectional view of the tool and handpiece of FIG. 36, showing the tool being retained in the slot of the handpiece as the carrier is withdrawn.

A semi-sectional view of the quick connect/disconnect mechanism is shown assembled within the handpiece 802 body in FIG. 35. In operation, as shown in FIGS. 36-38, the user aligns the hub's protrusion 855 with the opening 827 of the quick connect/disconnect body 825 using the carrier 852. Then, the user inserts the hub 854 until stops up against a surface 845 of the quick connect/disconnect body 825. A carrier surface 847 pushes the retaining ring 833 inwardly causing the spring 841 to collapse. The user rotates the carrier 852 clockwise to lock the hub's protrusion 855 into the radial opening 827. An opening 821 can create a flexible element 823 to retain the protrusion 855 in place when the carrier 852 is released from the protrusion 855. As the carrier 852 moves away from the handpiece 852, the spring 841 is decompressed, moving the retaining ring 833 distally. A surface 819 of the retaining ring 833 prevents the protrusion 855 from rotating.

Figure 39:
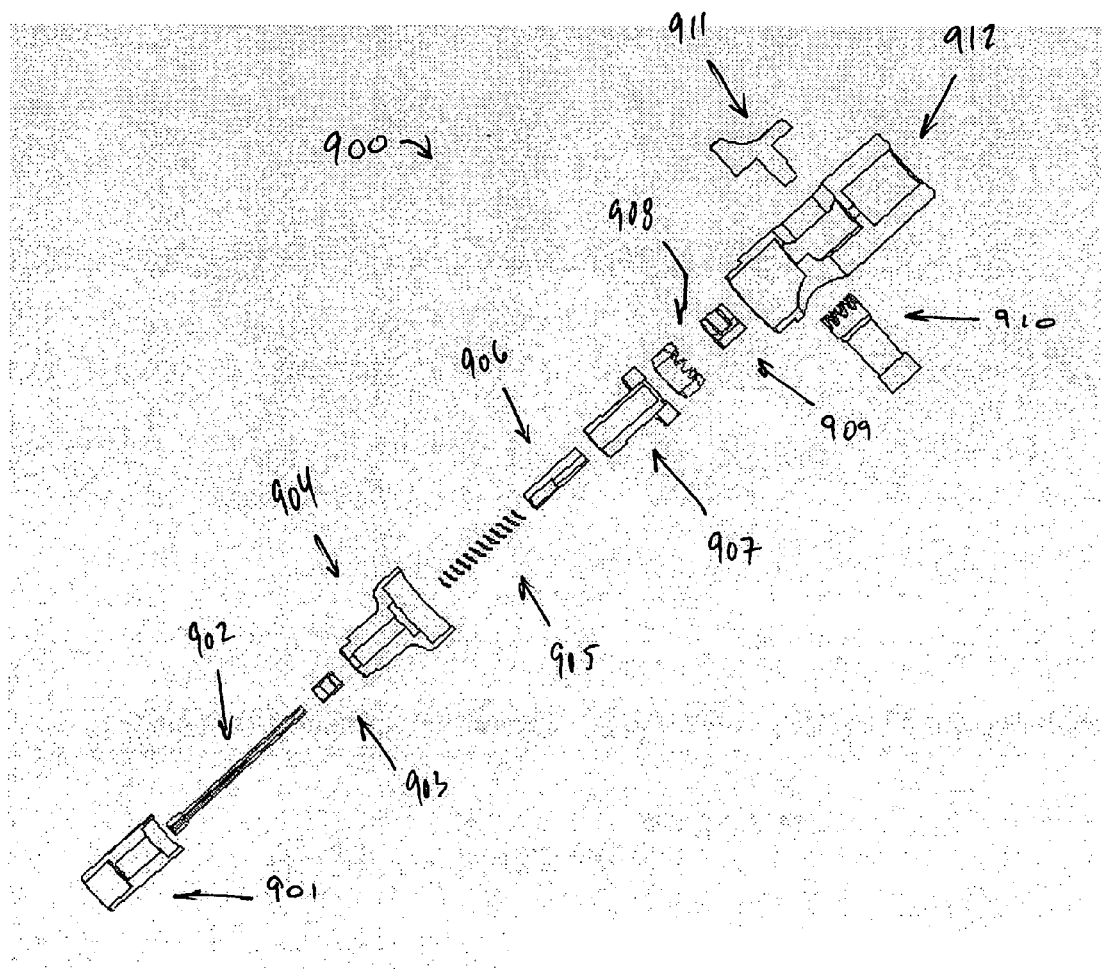
FIG. 39 is an exploded perspective view of another embodiment of a tool connection and actuation system for an injection system handpiece.
Figure 40:
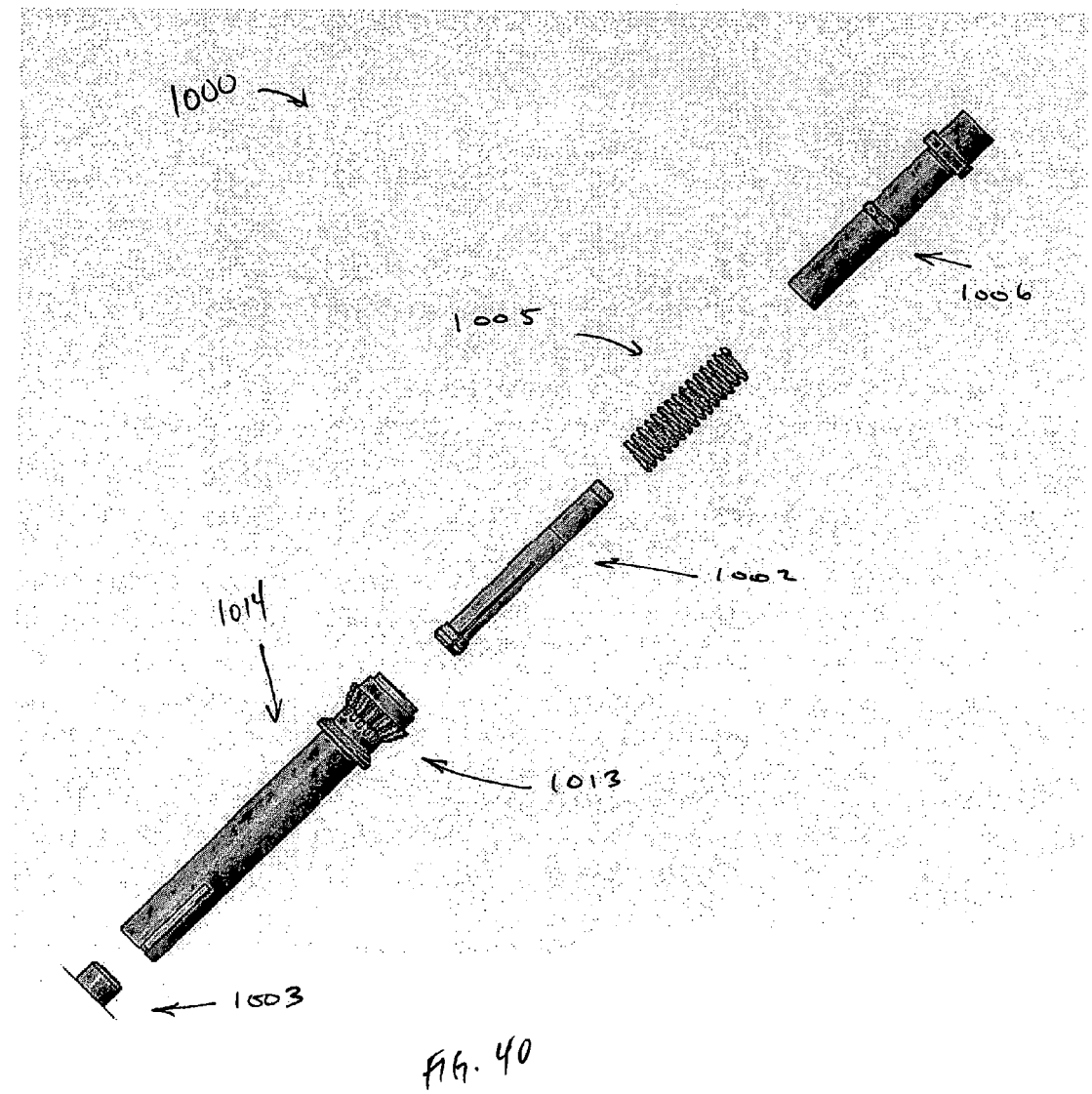
FIG. 40 is an exploded perspective view of another embodiment of a tool connection and actuation system for an injection system handpiece.
Figure 41:
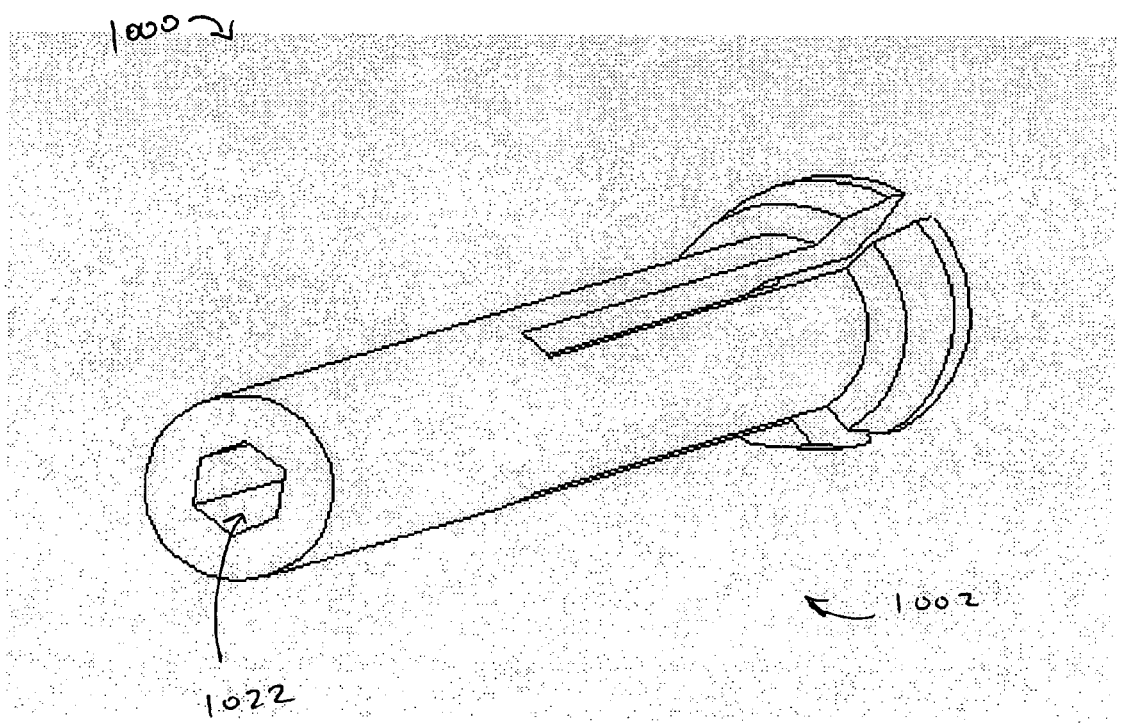
FIG. 41 is a perspective view of a collet mechanism of the tool connection and actuation system of FIG. 40.

FIG. 39 shows an exploded view of one embodiment of an injection system 900, having a rotating gear mechanism. The system 900 comprises a distal collet housing 901, a collet 902, a locking bushing 903, a top collet housing 904, a spring 905, a driver 906, an aligning sleeve 907, a gear 908, a bushing 909, a gear motor 910, a button or lever 911, and a body 912. FIG. 40 is an exploded view of another embodiment of an injection system 1000 having a collet mechanism in which gear feature 1013 is part of a collet housing 1014. The mechanism also includes a collet 1002, a spring 1005, a locking bushing 1003, and a driver 1006. The collet mechanism can be assembled into a housing and body components such as those described with reference to FIG. 39. The collet 1002 can have an internal anti-rotational feature, such as a polygonal internal cavity 1022, as shown in FIG. 41 that engages a corresponding matching outer body of a tool to prevent rotation or premature dislodging of the tool.

Figure 42:
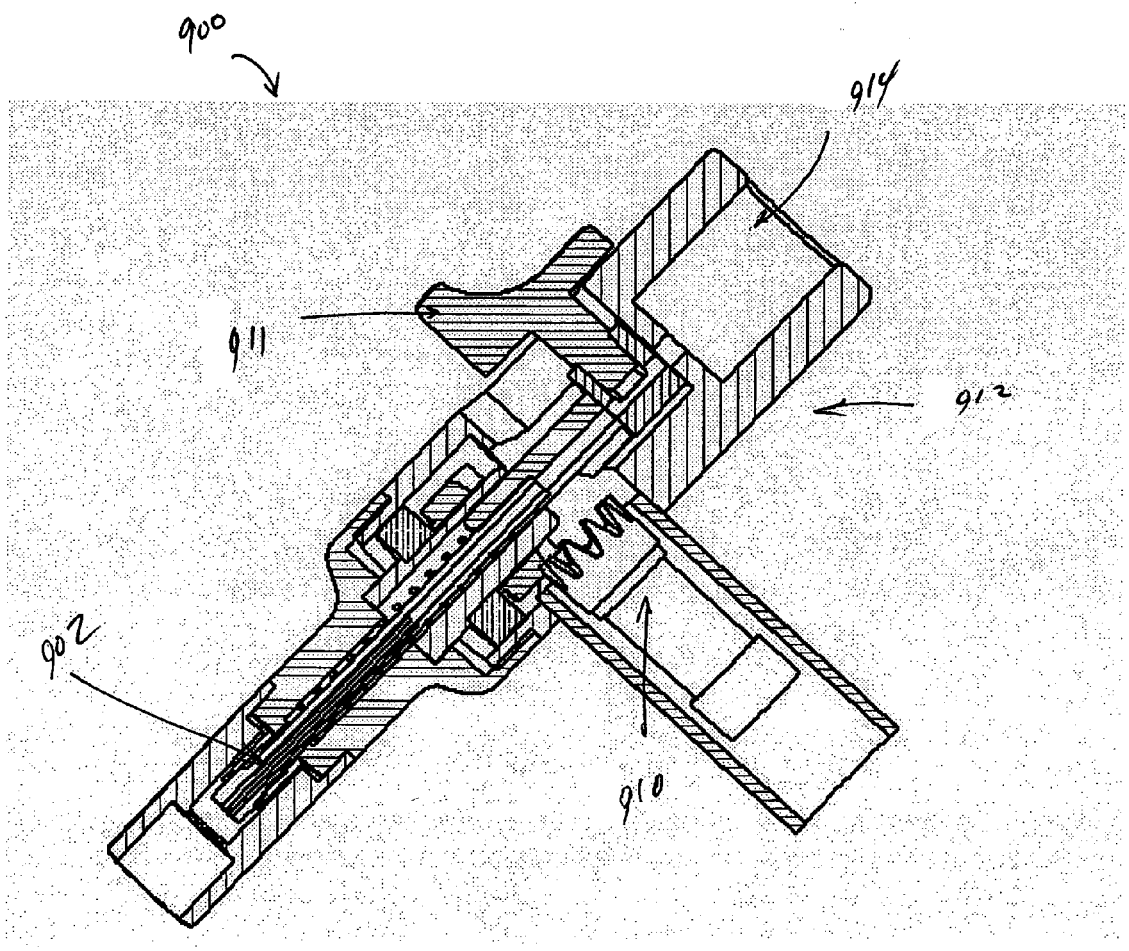
FIG. 42 is sectional view of the assembled tool connection and actuation system of FIG. 39.
Figure 43:
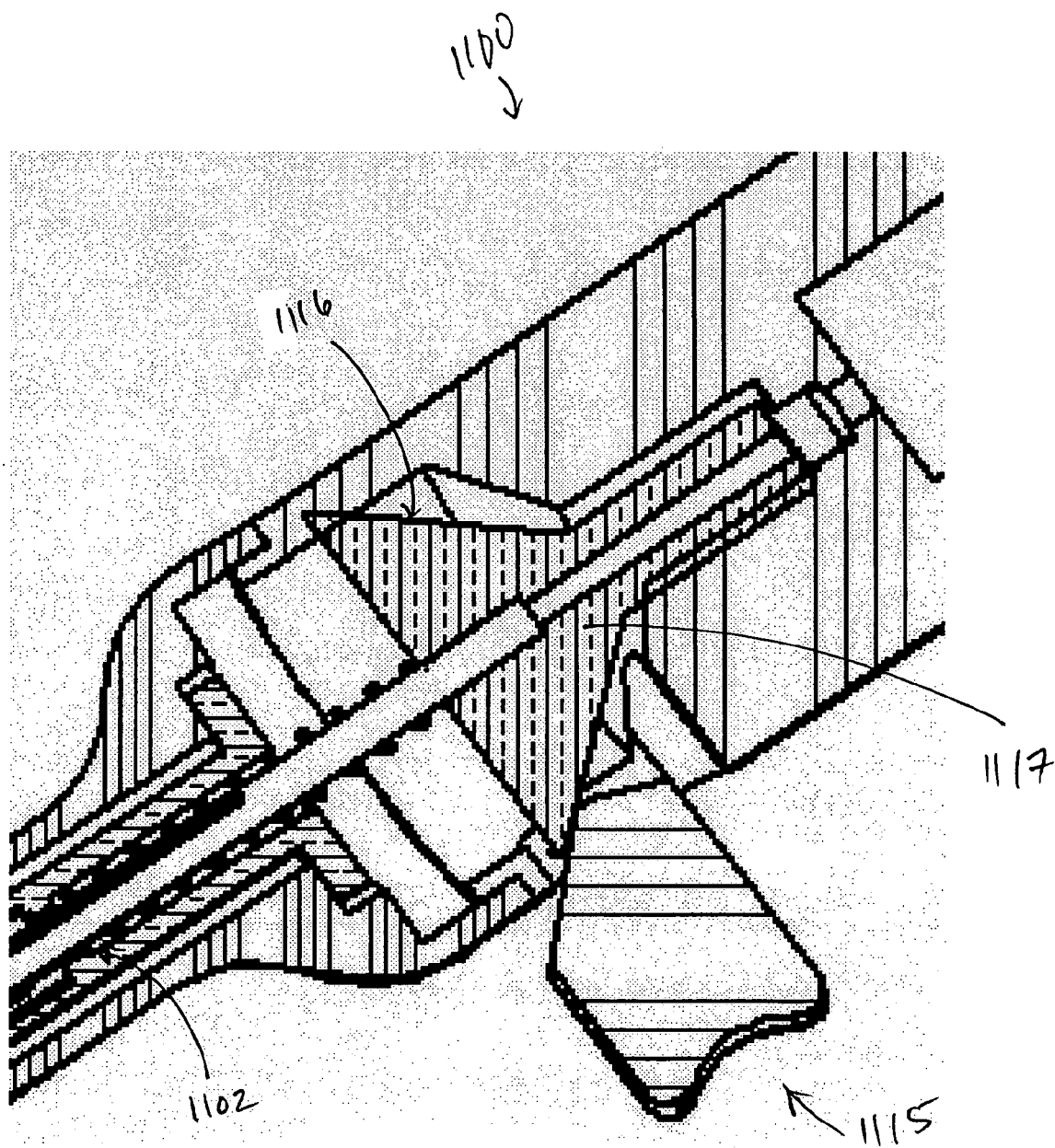
FIG. 43 is a sectional view of a portion of another embodiment of a tool connection and actuation system for an injection system handpiece.

FIG. 42 is a cross-sectional view of the assembly of the system 900 described above. An inner surface 914 of the body 912 can connect to a syringe or another device that delivers anesthetics, or any other fluids or substances, such as antibiotics, composites, and/or coolant, etc. The surface 914 allows for direct tool and/or needle insertion into an ampoule. The motor gear 910 is connected to a motor that has the ability to reverse its direction when a desired torque is achieved. The operator can open the collet 902 by pushing down the button 911. In another embodiment of an injection system 1100, as show in FIG. 43, a button 1115 that is pushed inwardly slides on a tapered surface 1116 of a driver 1117, which moves the driver 1117 distally to open a collet 1102.

Figure 44:
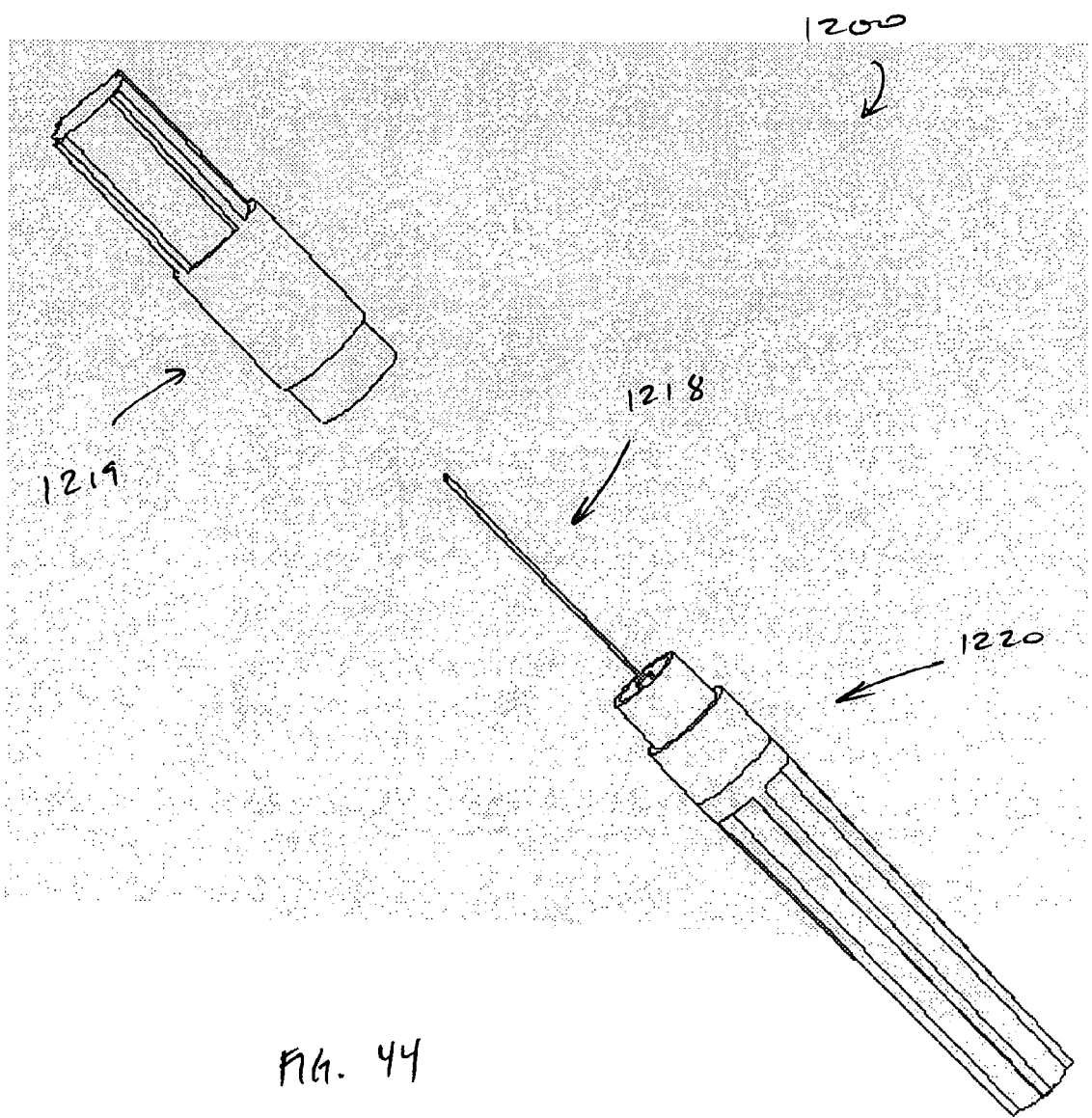
FIG. 44 is a perspective view of one embodiment of a tool and a tool carrier assembly with a cap.
Figure 45:
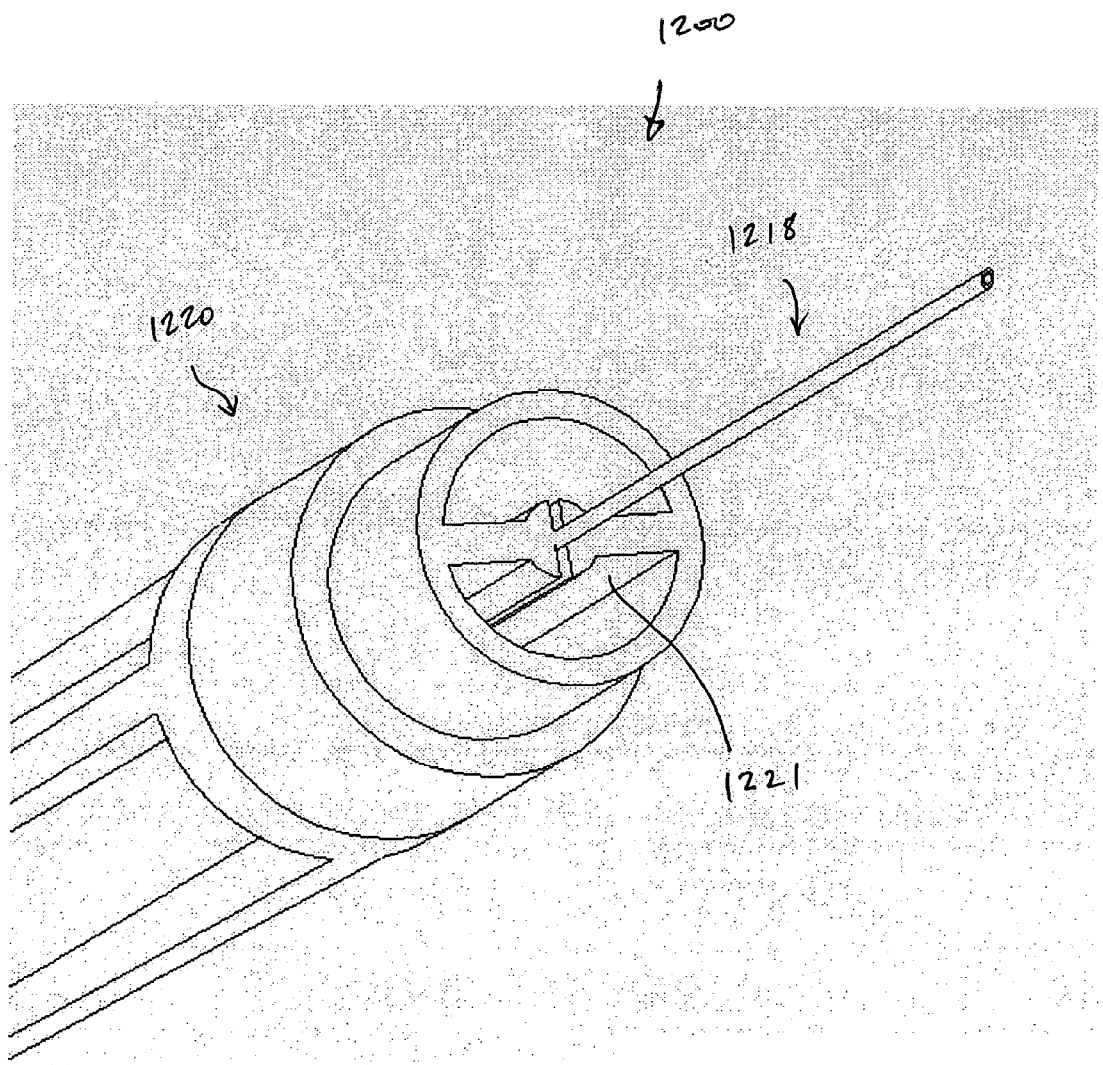
FIG. 45 is a perspective view of the tool and tool carrier assembly of FIG. 44.

FIG. 44 is a perspective exploded view of one embodiment of an injection system 1200 having a tool, e.g., needle 1218, a protective cap 1219, and a carrier 1220. The carrier 1220 preferably holds the bared needle 1218 using gripping elements 1221 as shown in FIG. 45.

Figure 46:
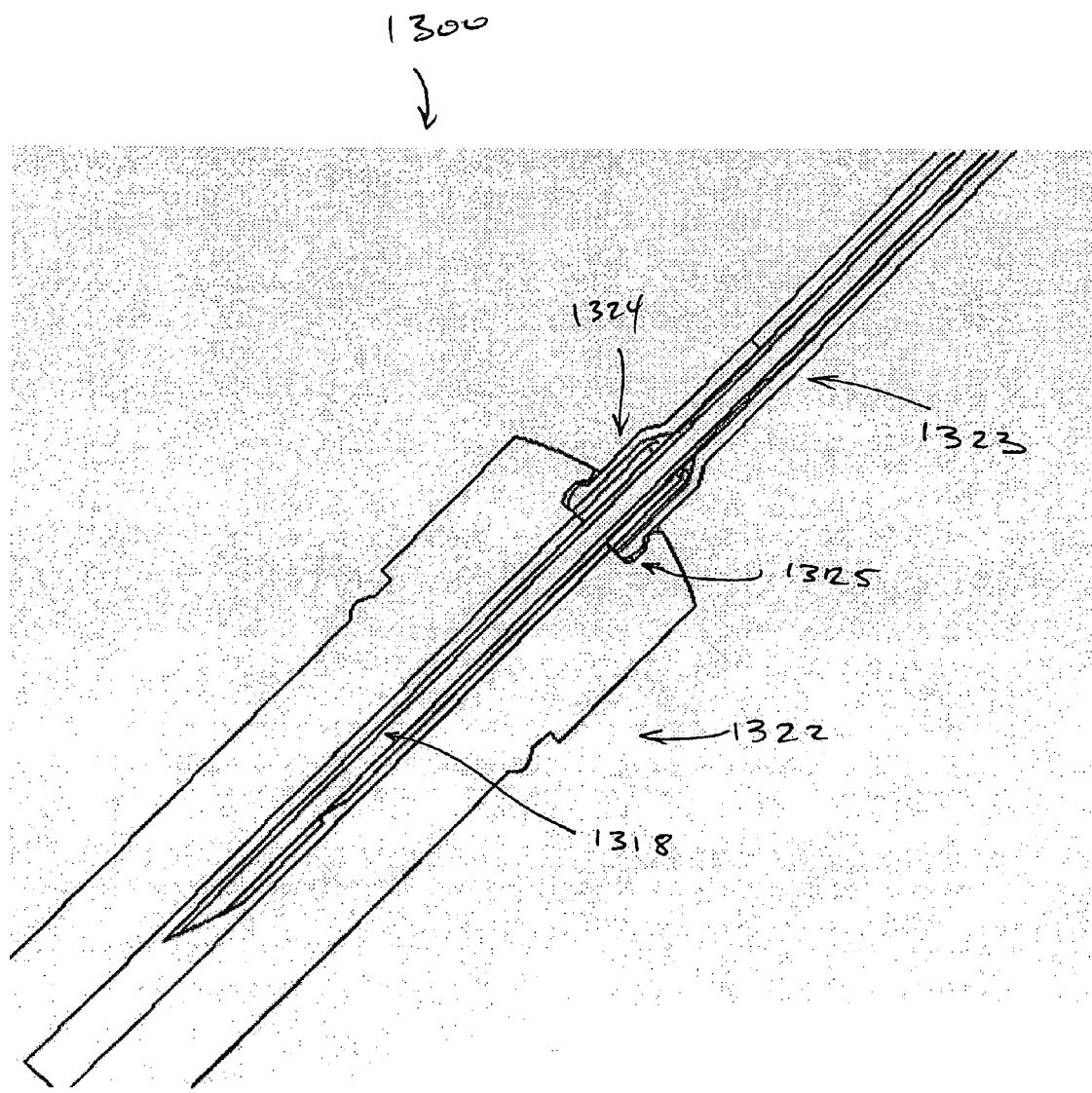
FIG. 46 is a sectional view of another embodiment of a tool and a tool carrier assembly, showing a tool with a hub.
Figure 47:
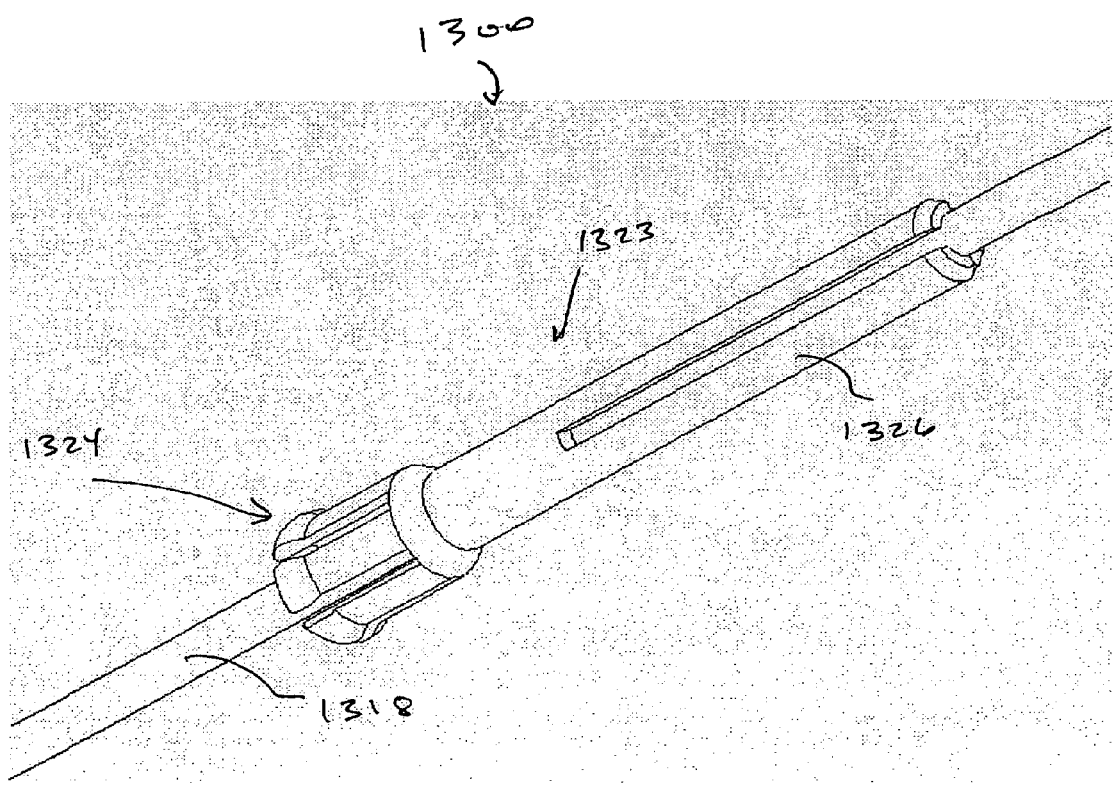
FIG. 47 is an enlarged view of the tool and hub of FIG. 46.

As shown in FIG. 46, another embodiment of an injection system 1300 includes a carrier 1322 that holds a needle 1318 and a hub assembly 1323 by encapsulating flexing elements 1324 of the hub 1323 inside a cavity 1325. FIG. 47 is a perspective view of the hub 1323 assembled with needle 1318. The hub 1323 has flexing elements 1324 at its distal end to allow for the easy removal from the carrier 1322 shown in FIG. 46. These flexing elements 1324 can be reinserted back in the carrier 1322 to facilitate the removal of the needle/hub assembly from the collet mechanism 902 described above with reference to FIG. 39. In another embodiment, the flexing elements can be part of the carrier, as shown in FIGS. 3A and 3B and discussed above. Having the flexing elements on the carrier facilitates manufacturing and provides a strong connection. The needle 1318 can be coupled or connected to the hub 1323 using current manufacturing methods, such as insert molding, welding, interlocking, sealing, or light-cure adhesive technologies. The needle 1318 can have anti-rotational features such as rough finishes, out of round geometries, knurled surfaces, or other features to further improve its engagement with the hub 1323. The hub 1323 preferably has a shaft that can compress. In some embodiments, the hub 1323 can be made of plastic material and/or can include flexing features 1326 that allow for an indirect gripping of the tool by the collet mechanism, thereby preventing the tool from disengaging the hub 1323. In some embodiments the hub can be made of metal or hard plastic to prevent its deformation during gripping and facilitate its removal. In other embodiments, the tool and/or hub 1323 can have a non-circular outer shaft that engages the non-circular inside cavity 1022 of the collet 1002 of FIG. 41. In another embodiment, the hub portion of the tool can have one or more rough surfaces to prevent slipping of the tool from the collet or chucking mechanism.

Figure 48:
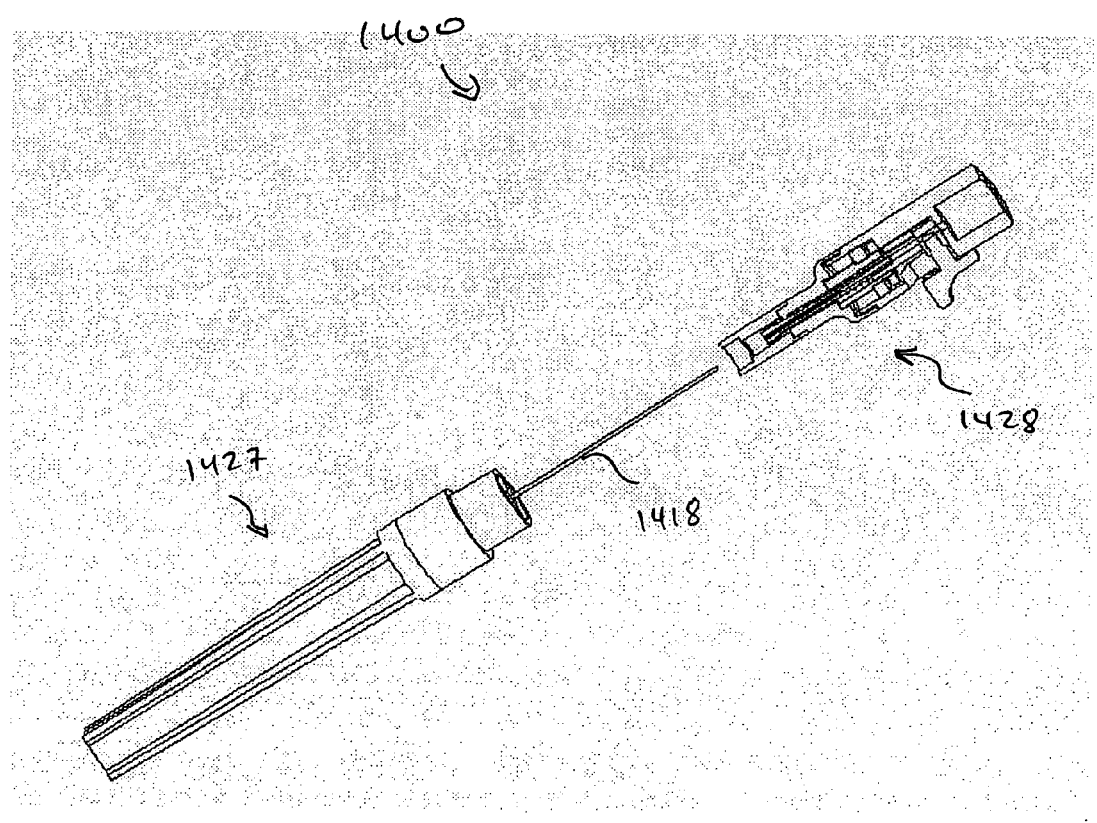
FIG. 48 is a perspective, partial sectional view of another embodiment of a tool and a tool carrier assembly and a tool connection and actuation system for an injection system.
Figure 49:
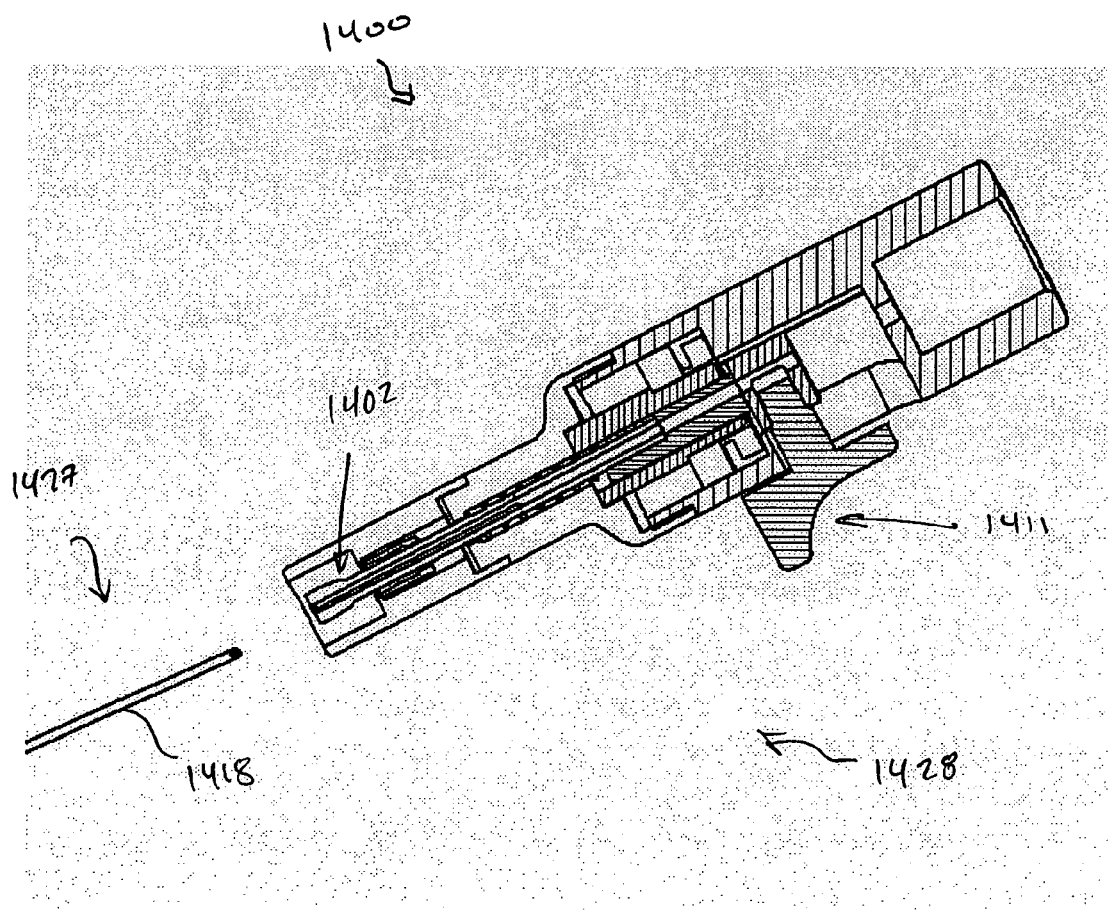
FIG. 49 is an enlarged perspective, partial sectional view of the tool and a portion of a handpiece of the injection system FIG. 48.
Figure 50:
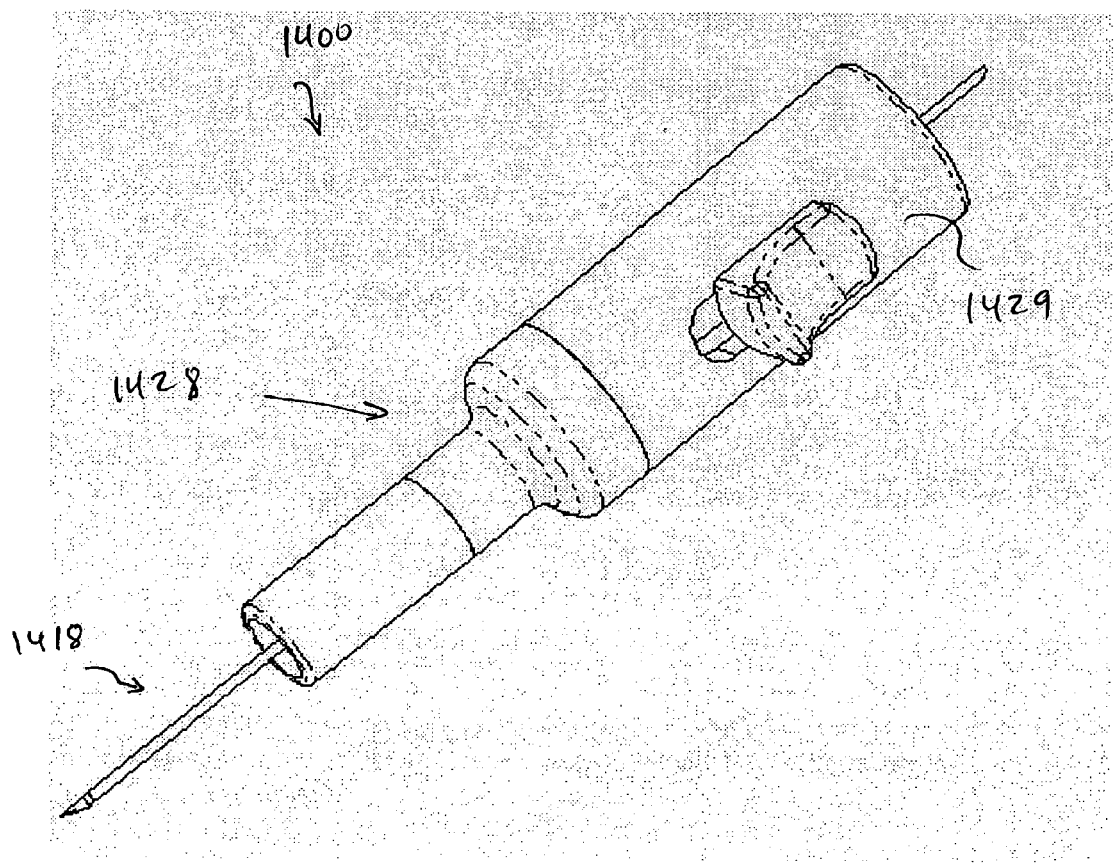
FIG. 50 is a perspective view of the assembled tool and handpiece portion of the injection system of FIG. 49.
Figure 51:
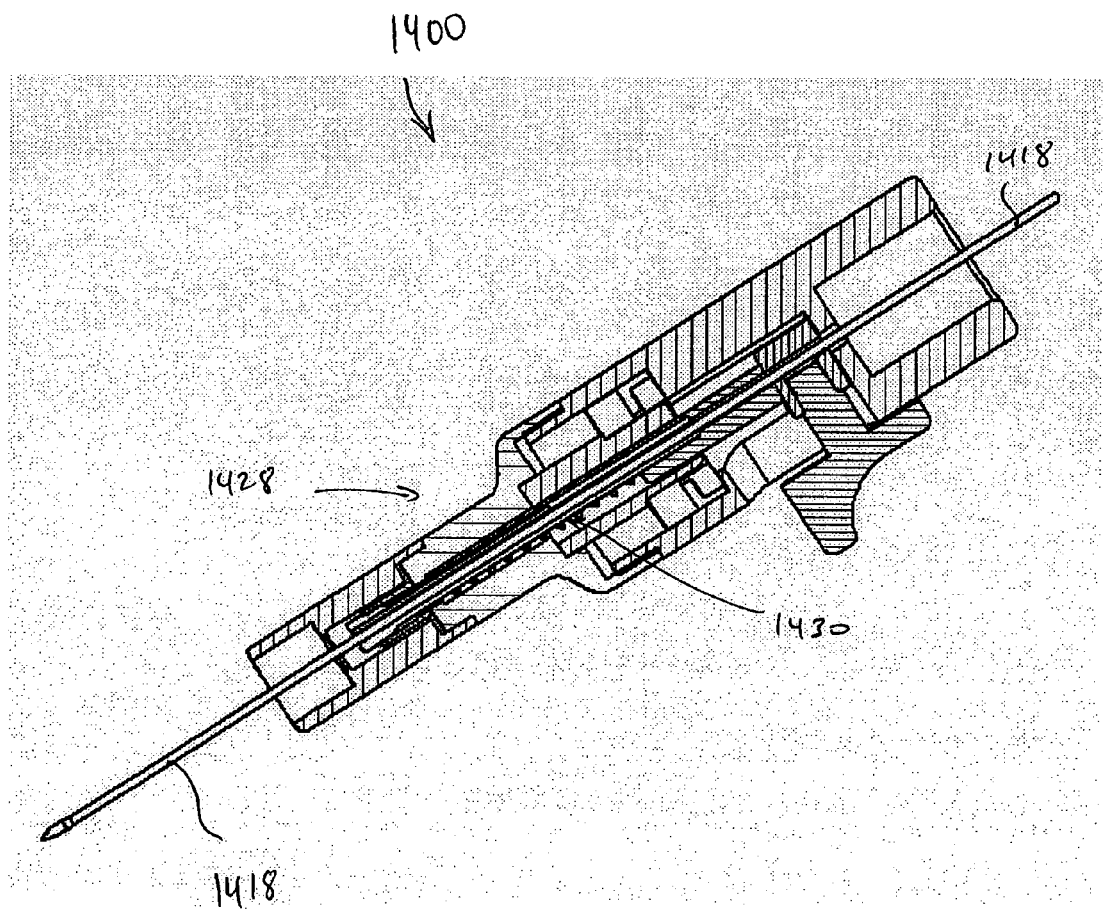
FIG. 51 is a sectional view of the injection system of FIG. 50.

FIG. 48 is a perspective view of another embodiment of an injection system 1400, having a carrier/needle assembly 1427 and a static gripping mechanism 1428. The gripping mechanism 1428 facilitates the loading of a tool and/or needle 1418 because the user can push a button 1411 to open the collet 1402 for insertion of the tool and/or needle 1418 as shown in FIG. 49. Accordingly, in some embodiments, the user is able to avoid having to thread the tool and/or needle hub assembly multiple times in order to ensure adequate engagement. FIG. 50 is a perspective view of the static gripping mechanism 1428 with the needle 1418 loaded in place. The body 1429 can be connected to any suitable syringe device. The needle 1418 goes through the internal features 1430 of the gripping mechanism 1428 as shown in FIG. 51 to directly engage an anesthetic cartridge and/or an ampoule that contains a variety of medications, composites and or coolants.

Figure 51A:
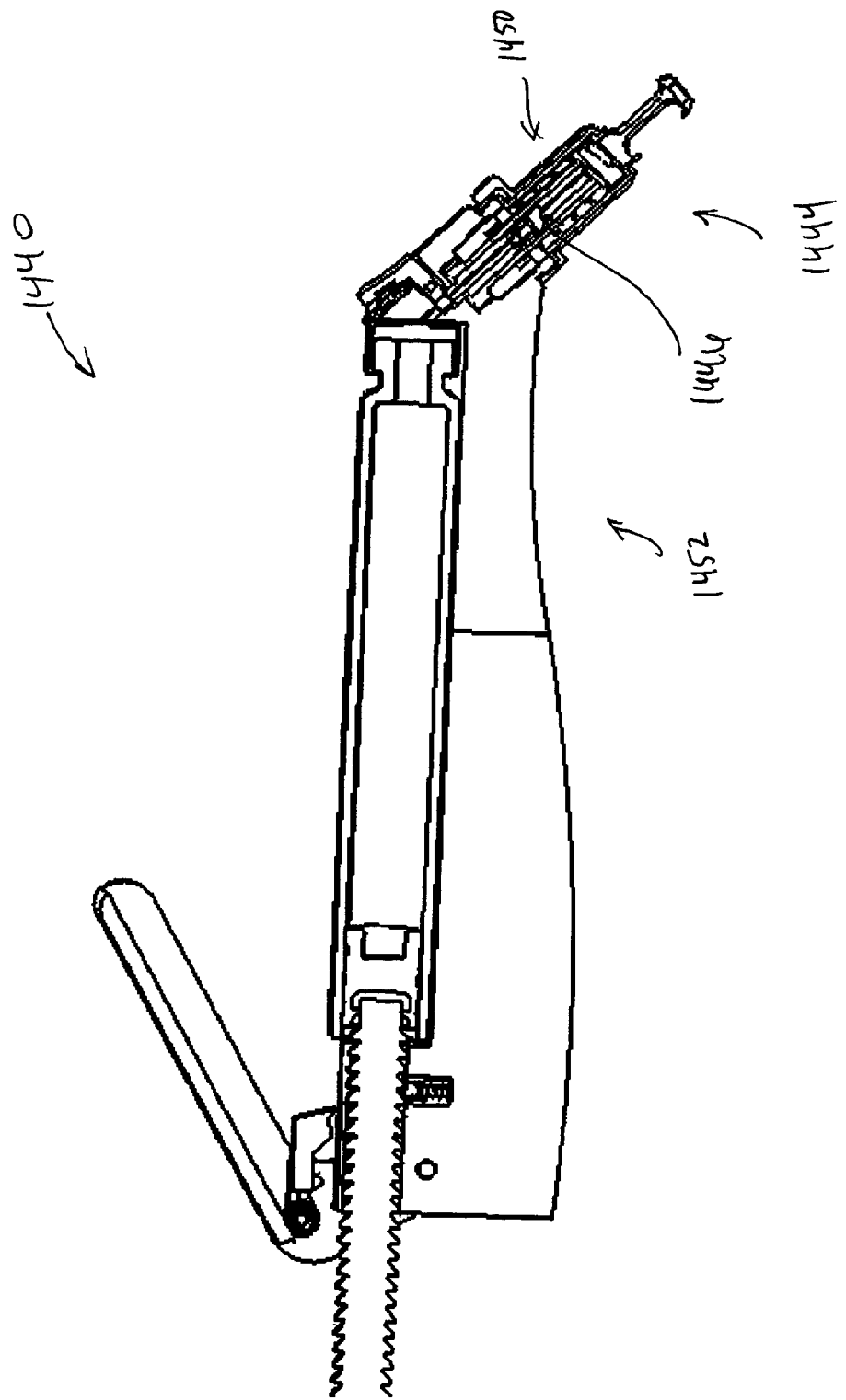
FIG. 51A is a schematic view of another embodiment of an injection system having a static gripping mechanism.

In another embodiment, a body 1450 similar to the body 1429 can be connected to a custom device 1452 shown in FIGS. 51A-51B. The custom device 1452 is similar to other handpieces described herein, except as described below. FIGS. 51A-51B are schematic views of another embodiment of an injection system 1440, having a static gripping mechanism 1444 with the needle loaded in place. The body 1450 can be connected to the custom dispensing handpiece device 1452 by positioning a proximal portion of the body 1450 over a distal portion of the handpiece device 1452. The needle goes through the internal features 1446 of the gripping mechanism 1444 to directly engage an anesthetic cartridge and/or an ampoule that contains a variety of medications, composites and or coolants.

2. Sleeve

Figure 52:
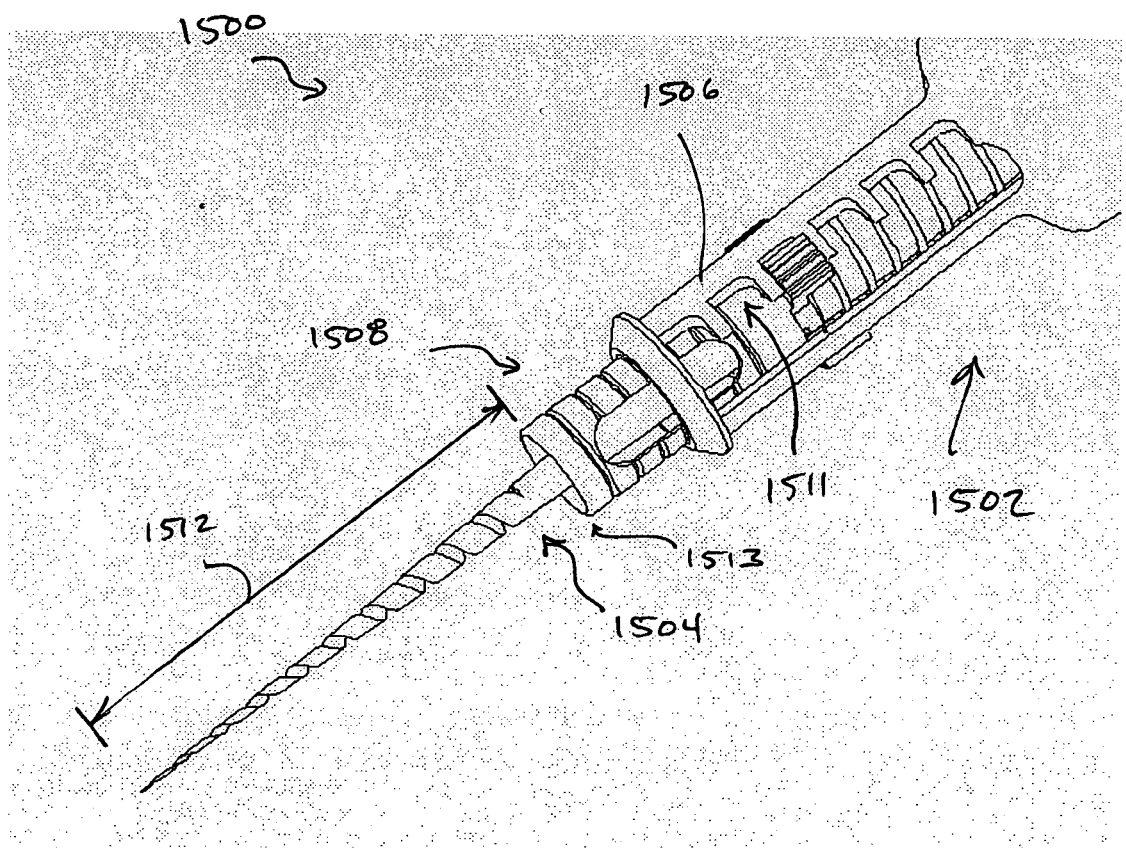
FIG. 52 is a perspective view of another embodiment of a tool, a tool connection and actuation system, and a sleeve for an injection system.

FIG. 52 shows an embodiment of an injection system 1500 having a handpiece 1502, a tool 1504, and a sleeve 1508. The sleeve 1508 of this embodiment is similar to the sleeve described above with reference to FIGS. 1-17, except as noted below. In this embodiment, the sleeve 1508 is adjustable or removable, provides a depth control feature, and is lockable in a plurality of positions. The handpiece 1502 preferably comprises a spring loaded protective sleeve 1508 for at least partially covering the tool 1504. As described above, the sleeve 1508 can be used to apply pressure to the tissue to minimize pain. The sleeve 1508 is also used to control the depth of insertion of the tool 1504. In some embodiments, the sleeve 1508 can move between a fully deployed position and a fully retracted position. The sleeve 1508 preferably can be locked in the fully deployed position, the fully retracted position, and/or in intermediate positions. Accordingly, the operator can determine the position of the sleeve 1508 for a particular application. In one embodiment, the sleeve 1508 can be coupled with the body of the handpiece via an adjustable connection, e.g., a threaded connection. The adjustable connection can allow a user to remove the sleeve 1508 from the body of the handpiece 1502. The adjustable connection can allow the user to vary the protrusion of the sleeve 1508 from the body of the handpiece for controlling the depth that the tool 1504 is inserted into the injection site. The adjustable connection can allow for the interchangeability of sleeves 1508 for different types or sizes of tools 1504, e.g., needles, hollow drills, dispensing tips, or files. The outer surfaces of the sleeve 1508 can have a coating, such as amorphous diamond coating. A coating can reduce tissue adhesion, making the sleeve easier to clean, and can reduce problems associated with a patient's nickel sensitivity.

As shown in FIG. 52, the sleeve 1508 provides a depth control feature. One or more openings 1511 along the axis of housing 1506 can lock the topical sleeve 1508 at any axial position to at least partially cover the tool 1504 to provide a specific depth of insertion 1512 when the surface 1513 of the topical sleeve 1508 contacts the topical site, e.g., tissue, bone, or tooth. The topical sleeve 1508 can engage the handpiece 1502 housing 1506 in a way that allows for its removal and/or for interchangeability purposes. If an operator decides not to use the topical sleeve 1508, the sleeve 1508 can be locked at the most proximal opening so the topical sleeve 1508 is fully retracted inside the housing 1506. The sleeve 1508 can also be threaded inside the body to allow for a custom depth of insertion, if desired, by simply unthreading or threading the sleeve from the housing.

Figure 53:
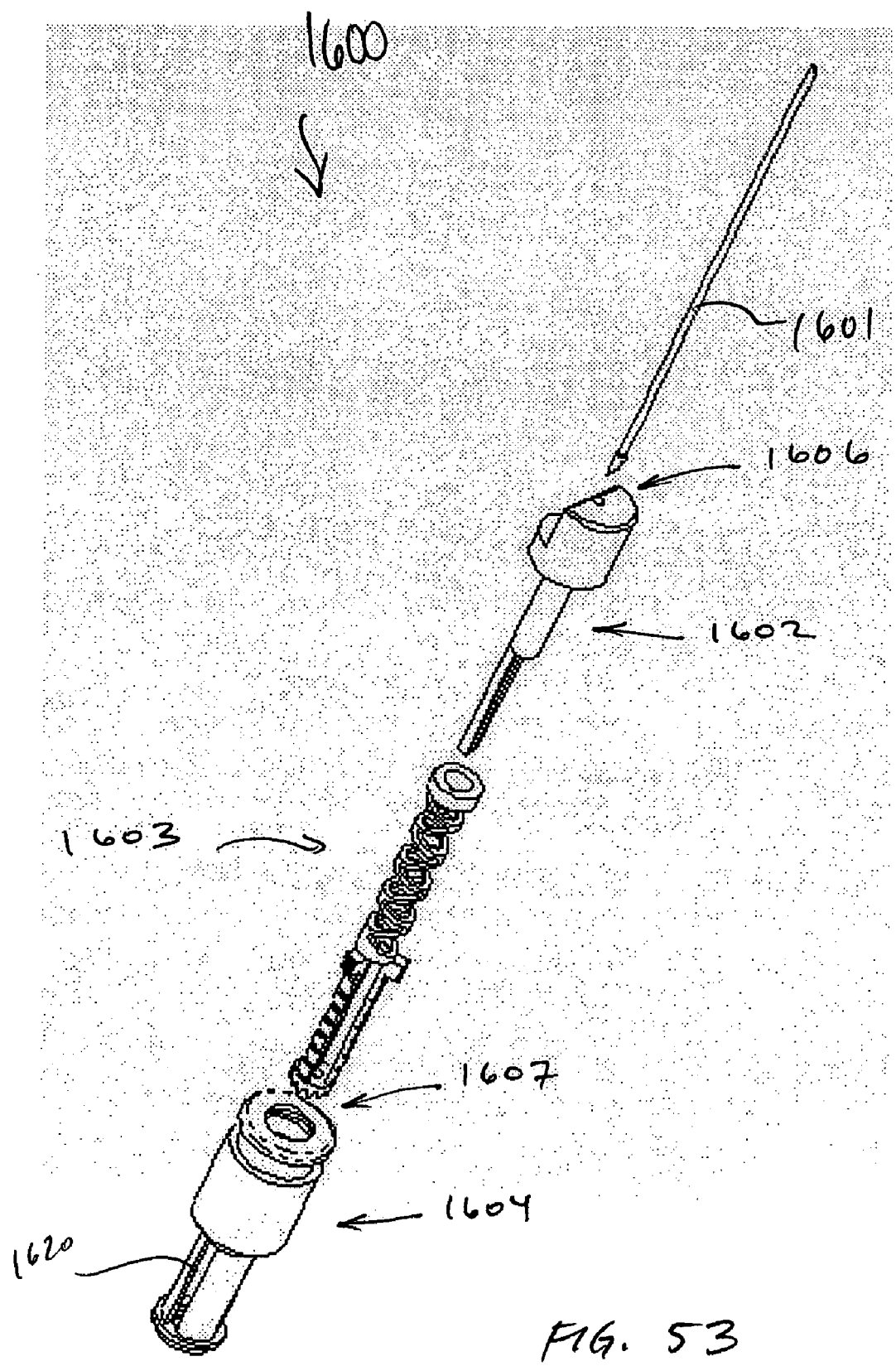
FIG. 53 is an exploded perspective view of another embodiment of a tool, and a sleeve mechanism for an injection system.
Figure 54:
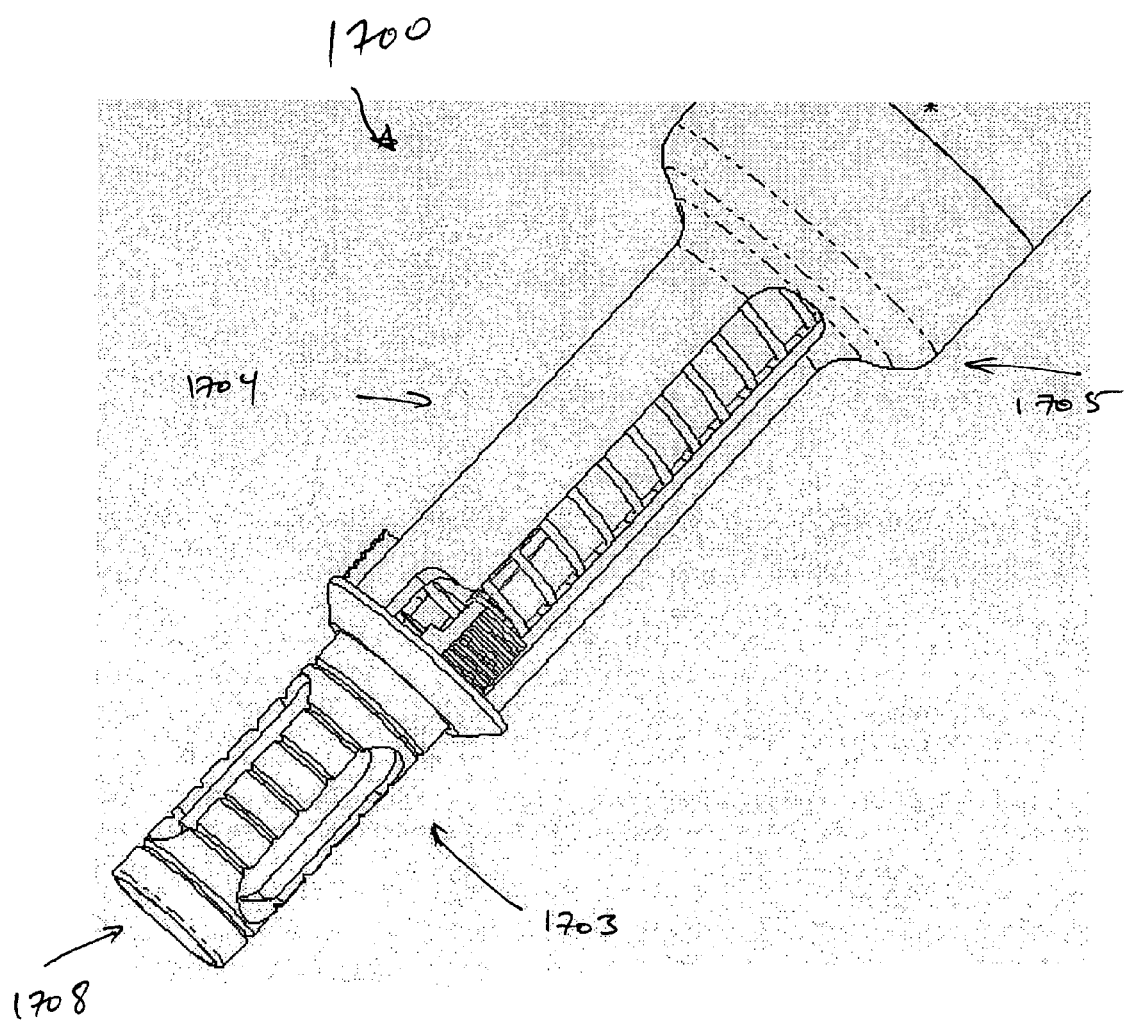
FIG. 54 is a perspective view of another embodiment of a sleeve mechanism on a handpiece for an injection system.
Figure 55:
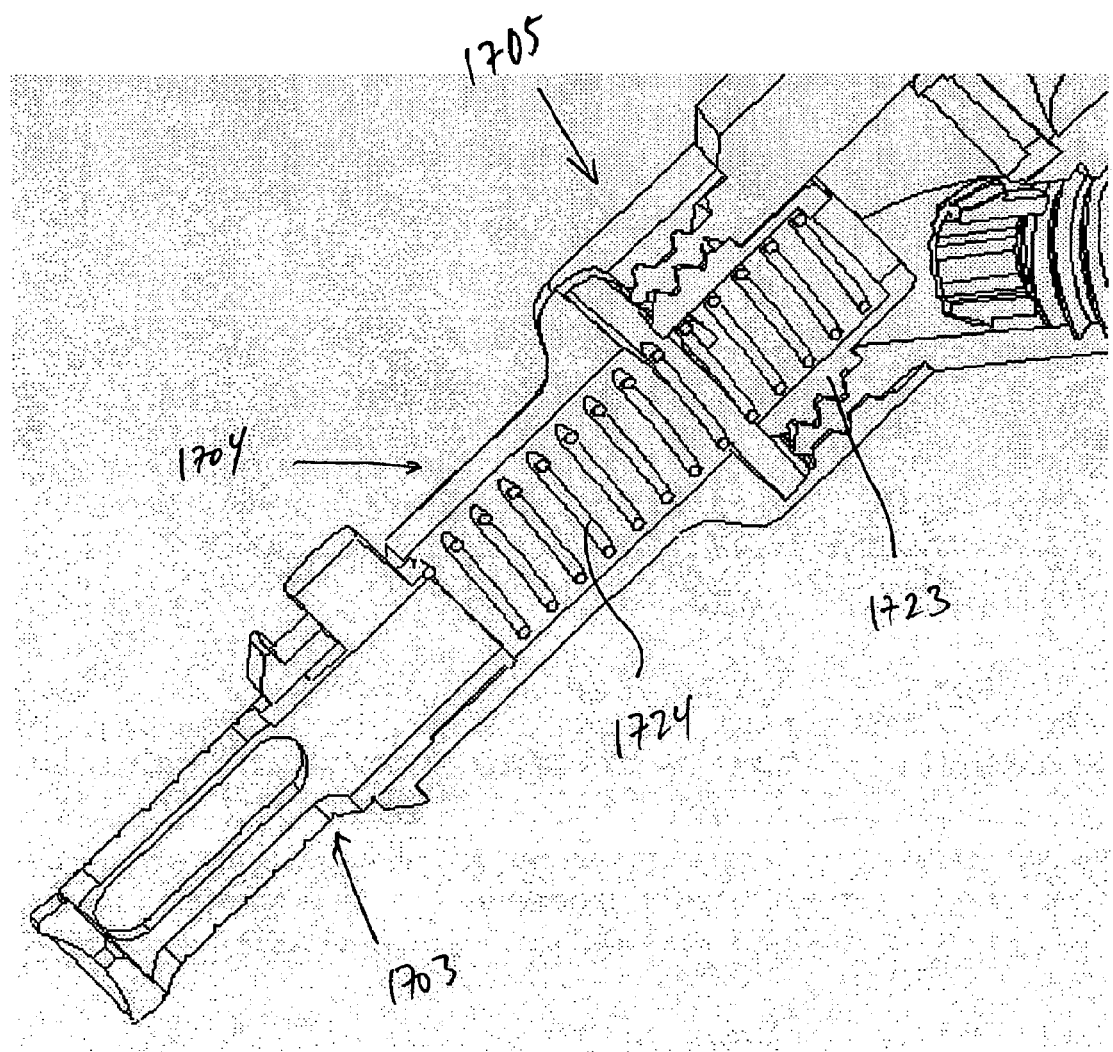
FIG. 55 is a sectional view of the sleeve mechanism of FIG. 54.

FIG. 53 shows an exploded view of one embodiment of an injection system 1600 having a needle that rotates or is pushed into the site. The device comprises a needle 1601, a needle hub driver 1602, a flexible protective sleeve 1603, and a protective sleeve housing 1604. The flexible protective sleeve 1603 is inserted through an access hole 1607 of the protective sleeve housing 1604. The needle 1601 can be a standard needle, an osseous needle, a file, a drill, or an osseous piercing component. The needle 1601 is inserted in the needle hub driver 1602 through a hole 1606. The needle hub driver assembly is inserted through the access hole 1607 of the protective sleeve housing 1604. In another embodiment of an injection system 1700, a flexible protective sleeve 1703, and a protective sleeve housing 1704 can be part of a handpiece device 1705 as shown in FIG. 54, in which the needle is inserted from the access hole 1708. The handpiece device 1705 preferably incorporates the topical protective sleeve 1703, the protective sleeve housing 1704, a spring 1724, and a spring retainer or stop 1723 as shown in FIG. 55.

Figure 56:
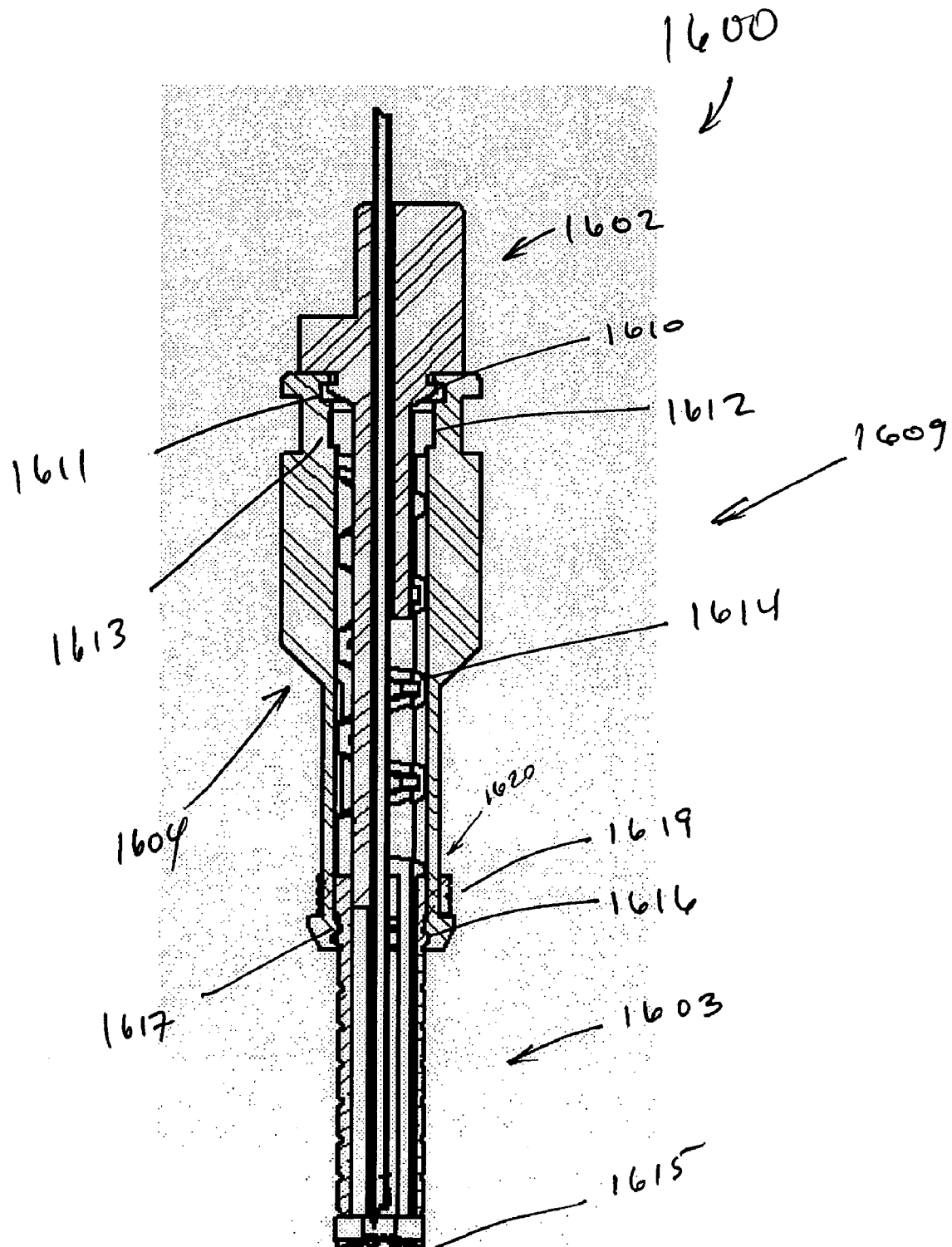
FIG. 56 is a sectional view of the sleeve mechanism of FIG. 53.
Figure 57:
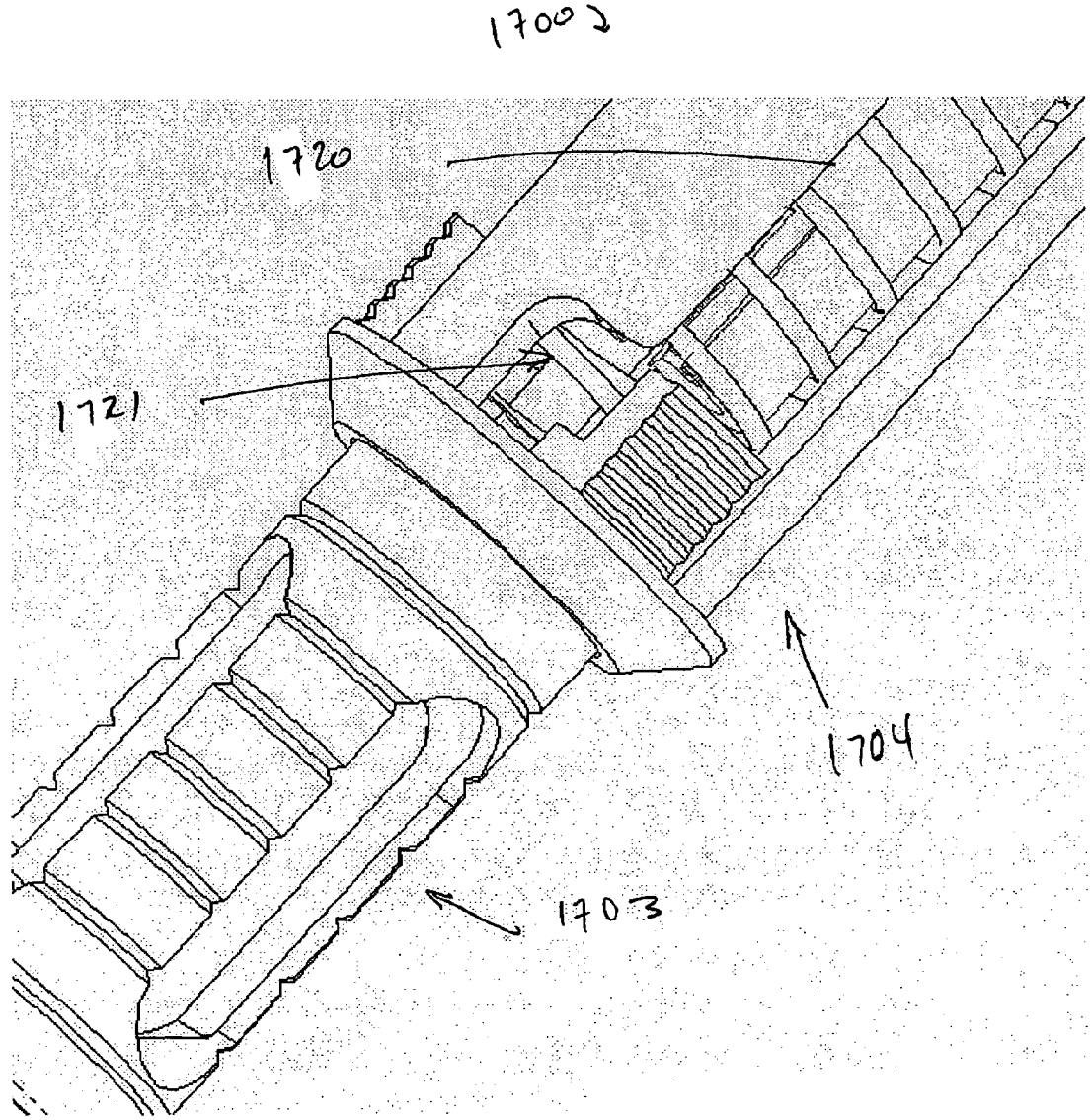
FIG. 57 is an enlarged perspective view of a portion of the sleeve mechanism of FIG. 54, shown in an unlocked position.
Figure 58:
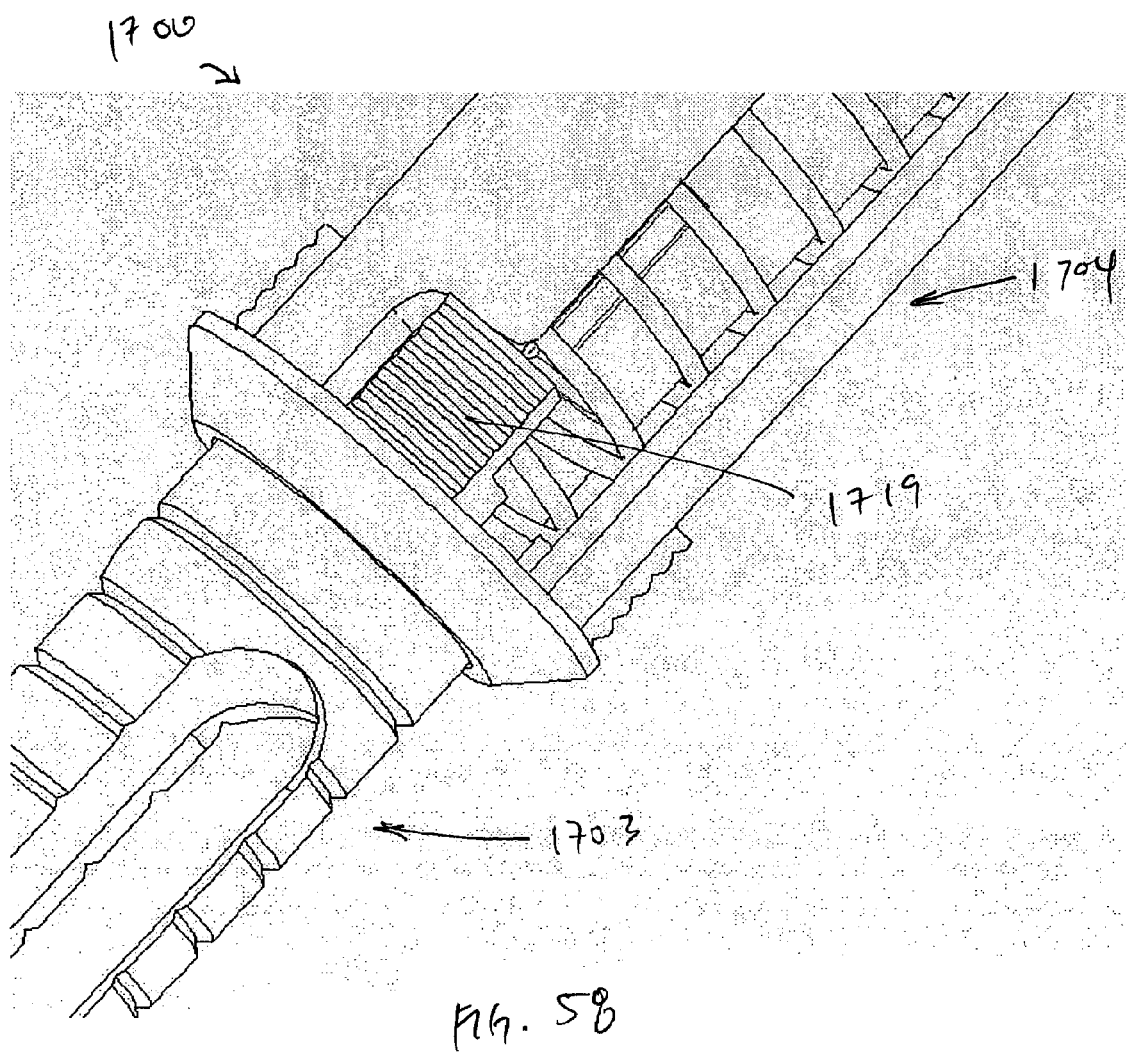
FIG. 58 is an enlarged perspective view of a portion of the sleeve mechanism of FIG. 54, shown in a locked position.

FIG. 56 is a cross-sectional view of the multi-piece sleeve embodiment 1600 that fits inside a handpiece. A needle hub driver protrusion, e.g., flange 1610, is inserted in an inner feature, e.g., groove 1611, of the protective sleeve housing. The needle hub driver 1602 is allowed to rotate without disengaging the assembly 1609. The outside surface, e.g., diameter 1612, at the proximal end of the flexible protective sleeve 1603 preferably is press fitted in the inside element 1613 of the housing 1604 to prevent it from coming off. The flexible features 1614 of the protective sleeve allow for compression or expansion as the distal end 1615 contacts the site. The protective sleeve 1603 has an outer ridge 1616 that engages an inner feature 1617, e.g., a groove, of the protective sleeve housing 1604, which provides a locking feature to prevent the sleeve from retracting and ensures that the needle is covered before transport to a point of use. The protective sleeve 1603 disengages the inner feature 1617 as pressure is applied to the distal end 1615 of the flexible protective sleeve. The protective sleeve 1603 also has one or more flanges 1619 that move axially through the openings 1620 of the protective sleeve housing 1604, as shown in FIG. 56. The flanges 1619 provide a gripping function to lock the protective sleeve 1603 in the inner feature 1617 of the housing 1604 to prevent it from moving during needle disposal. An alternative locking feature is shown in FIG. 57-58 in which the flange 1719 in a groove 1720 is rotated into a slot 1721 to prevent the protective sleeve 1703 from moving. In other embodiments a plurality of openings or slots 1721 can be provided along the axis of the housing 1704 to act as a stop to control the needle's insertion depth.

Figure 59:
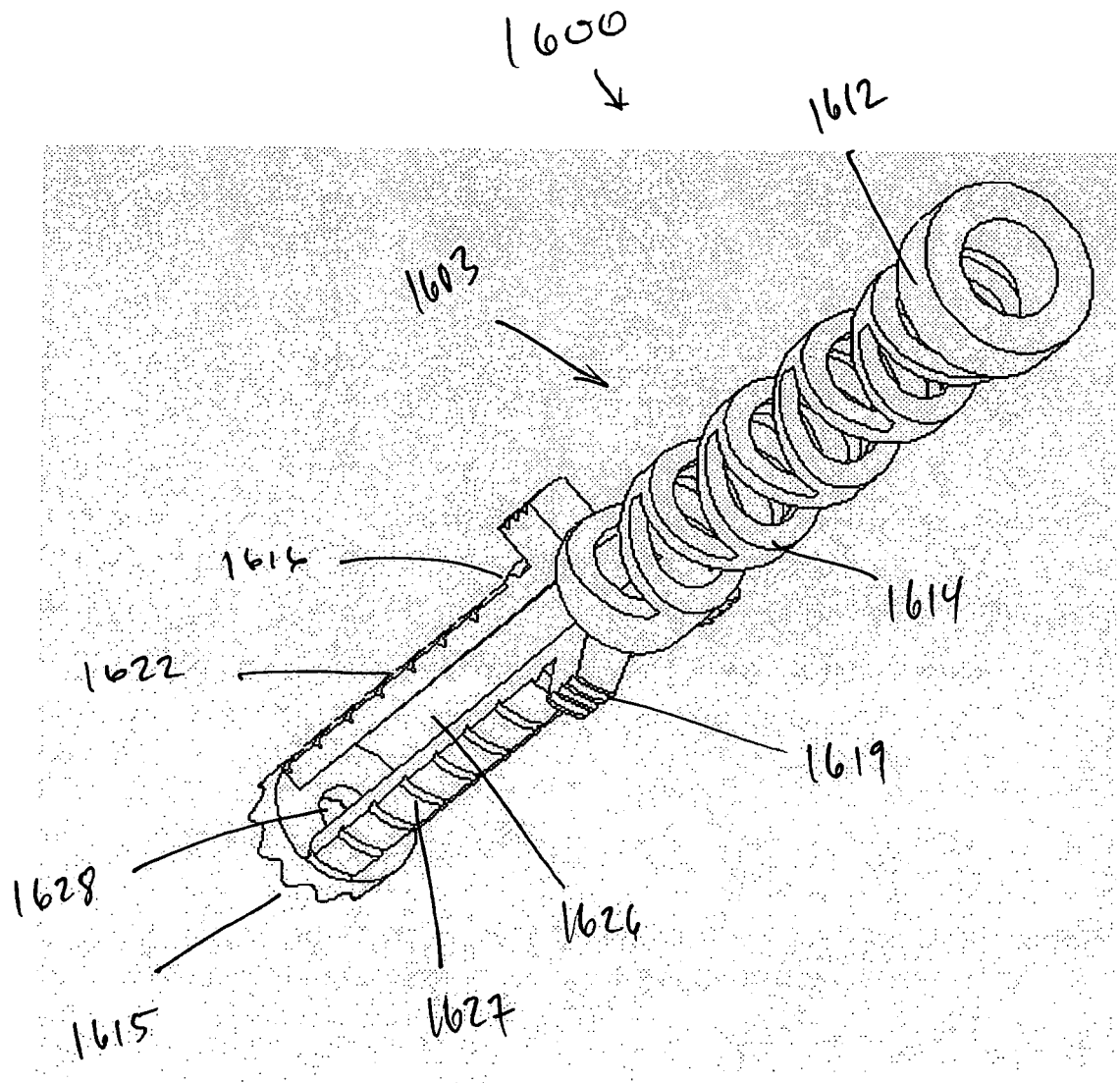
FIG. 59 is a perspective view of a portion of the sleeve mechanism of FIG. 53.
Figure 60:
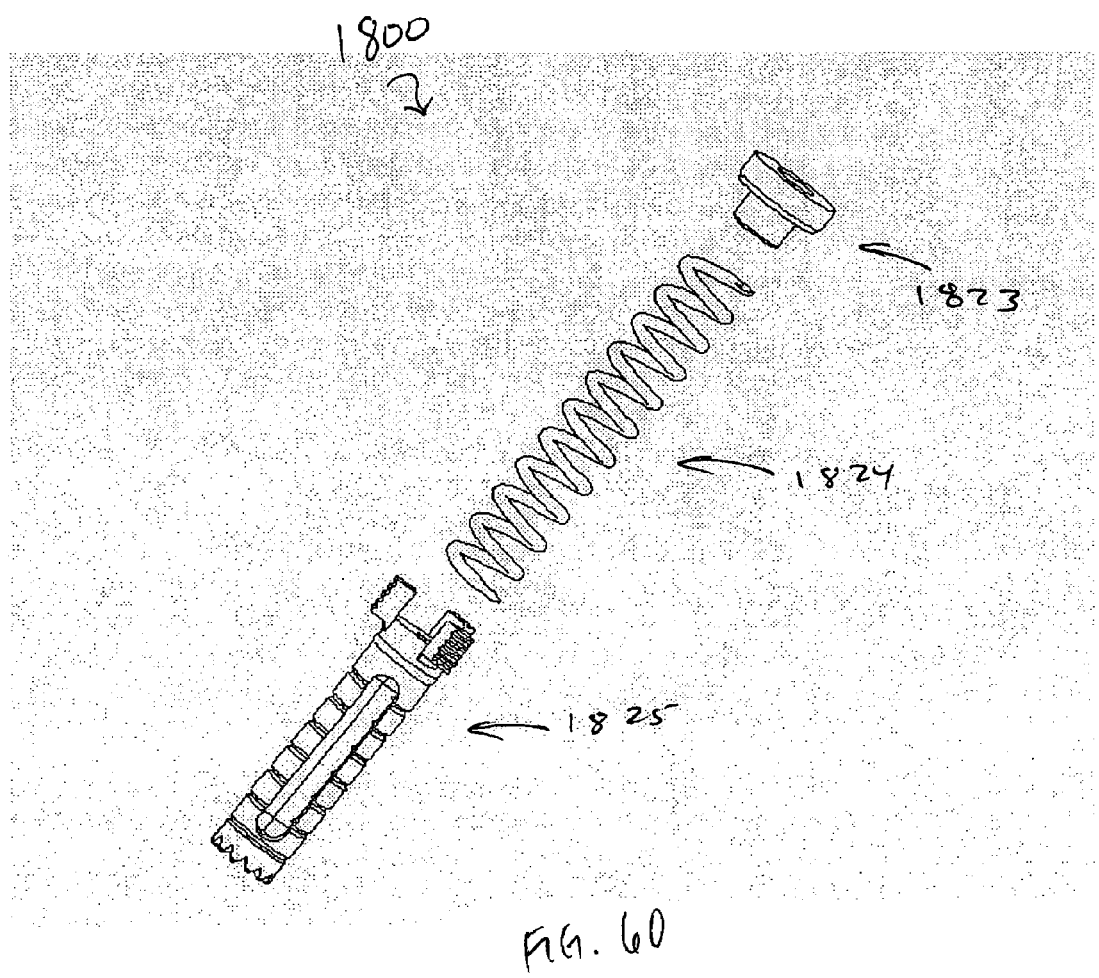
FIG. 60 is an exploded perspective view of another embodiment of a portion of a sleeve mechanism for an injection system.

FIG. 59 is an exploded view of the flexible protective sleeve 1603. The sleeve comprising of a distal hollow formation, such as a cylinder 1612, a flexible feature 1614, one or more flanges 1619, and a hollow structure, such as a cylinder 1622. In another embodiment of an injection system 1800 shown in FIG. 60, an assembly comprises first, second, and third separate pieces, a stop 1823, a spring 1824, and a hollow structure 1825. As shown in FIG. 59, system 1600 has a flexible feature comprising two arms that bend as the cylinder 1622 is pushed and that straighten as the pressure is released. The cylinder 1622 can have openings 1626 to allow for viewing of the needle. In another embodiment, the cylinder 1622 can be made out of a see-through material. The cylinder 1622 can have guidelines, e.g., grooves 1627, or marks, that can provide a visual guide to determine the depth of the needle as the cylinder 1622 is inserted into the protective sleeve housing 1604. The inner hole 1628 prevents the needle from bending while in use. The cylinder 1622 has a ridge 1616, or an outer protrusion, at its distal end that locks inside the inner feature of the housing 1604. The flexible feature 1614, such as a spring or a plastic or metal coil, allows for the axial movement of the cylinder 1622 as the needle is inserted or removed from the site. The proximal end 1612 is connected to the inner feature of the housing 1603 to prevent the sleeve 1603 from coming out. The distal end 1615 can offer a serrated and/or concave geometry to allow for indentation of soft tissue.

Figure 61:
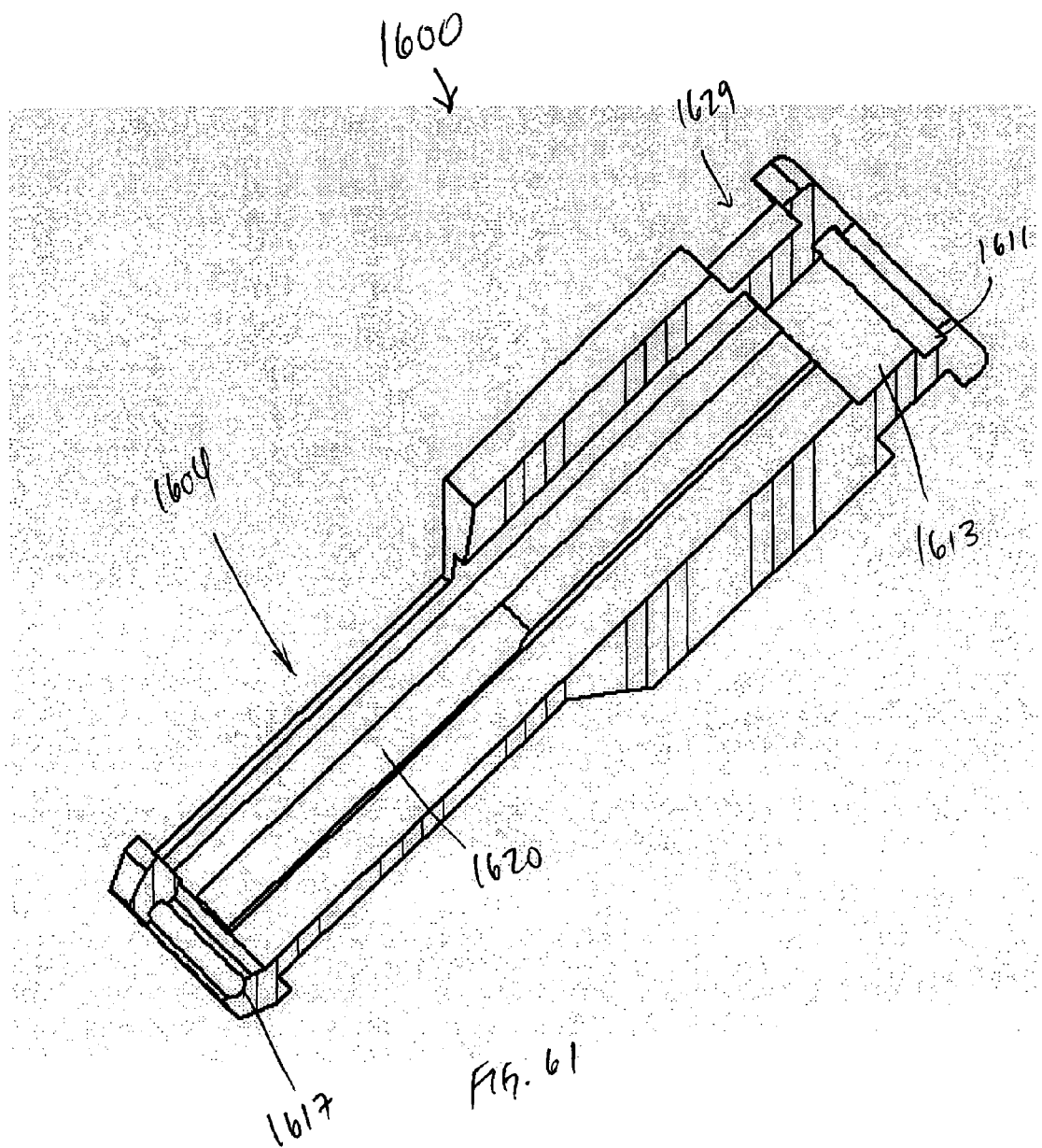
FIG. 61 is a sectional view of a protective sleeve housing of the sleeve mechanism of FIG. 53.

FIG. 61 is an isometric cross-sectional view of the protective sleeve housing 1604. The inner feature, e.g., groove 1611, at its distal end allows for the rotation of the needle driver 1602. The inside element, e.g., a diameter 1613, preferably fits tight with the distal cylinder 1611 of the protective sleeve 1603 as shown in FIG. 59. The one or more axial openings 1620 provide access for the flange 1619 of the protective sleeve 1603 to slide back and forth along its axis and to provide access for the user to lock the sleeve 1603 inside the inner groove 1617. The housing may be secured in a driving device using a locking feature, such as an outer groove 1629.

Figure 62:
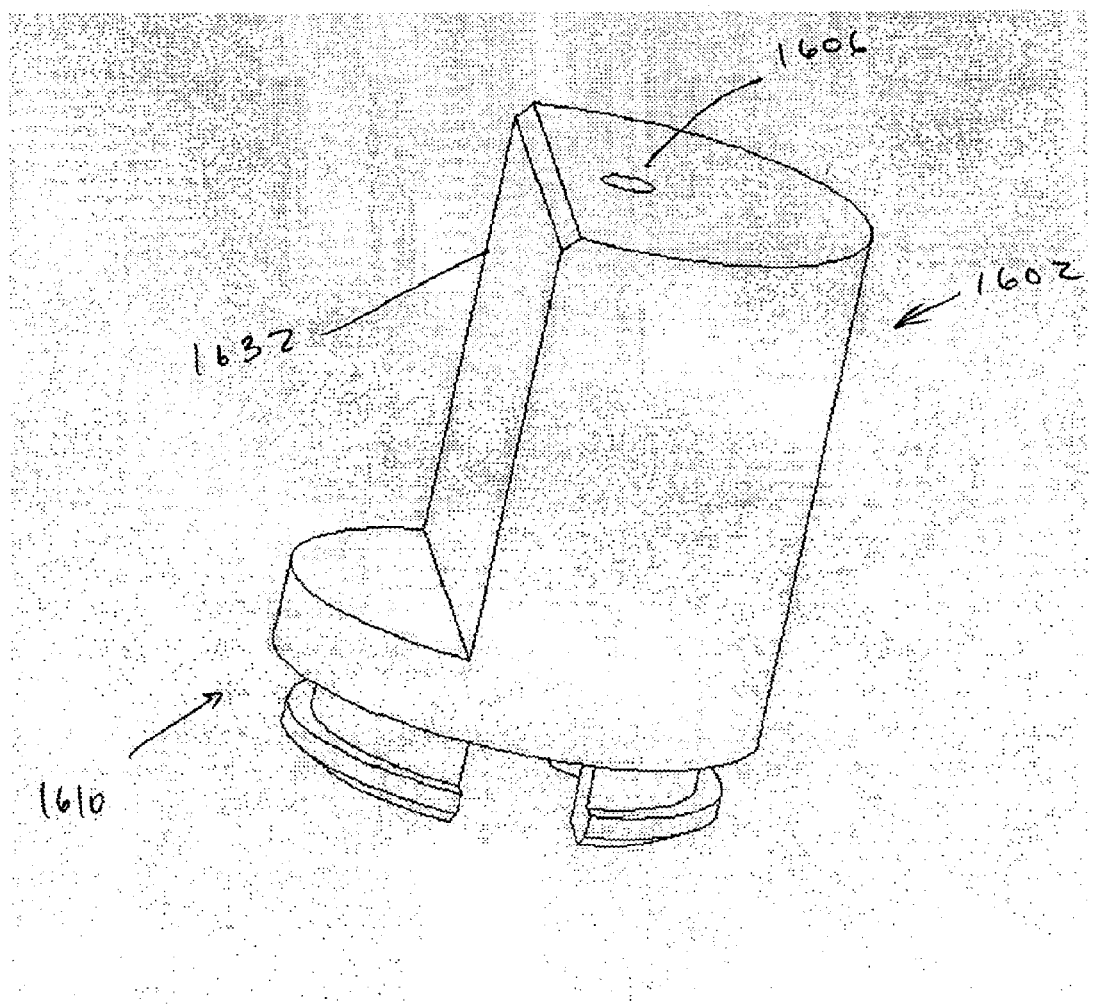
FIG. 62 is a perspective view of a needle hub driver of the injection system of FIG. 53.
Figure 63:
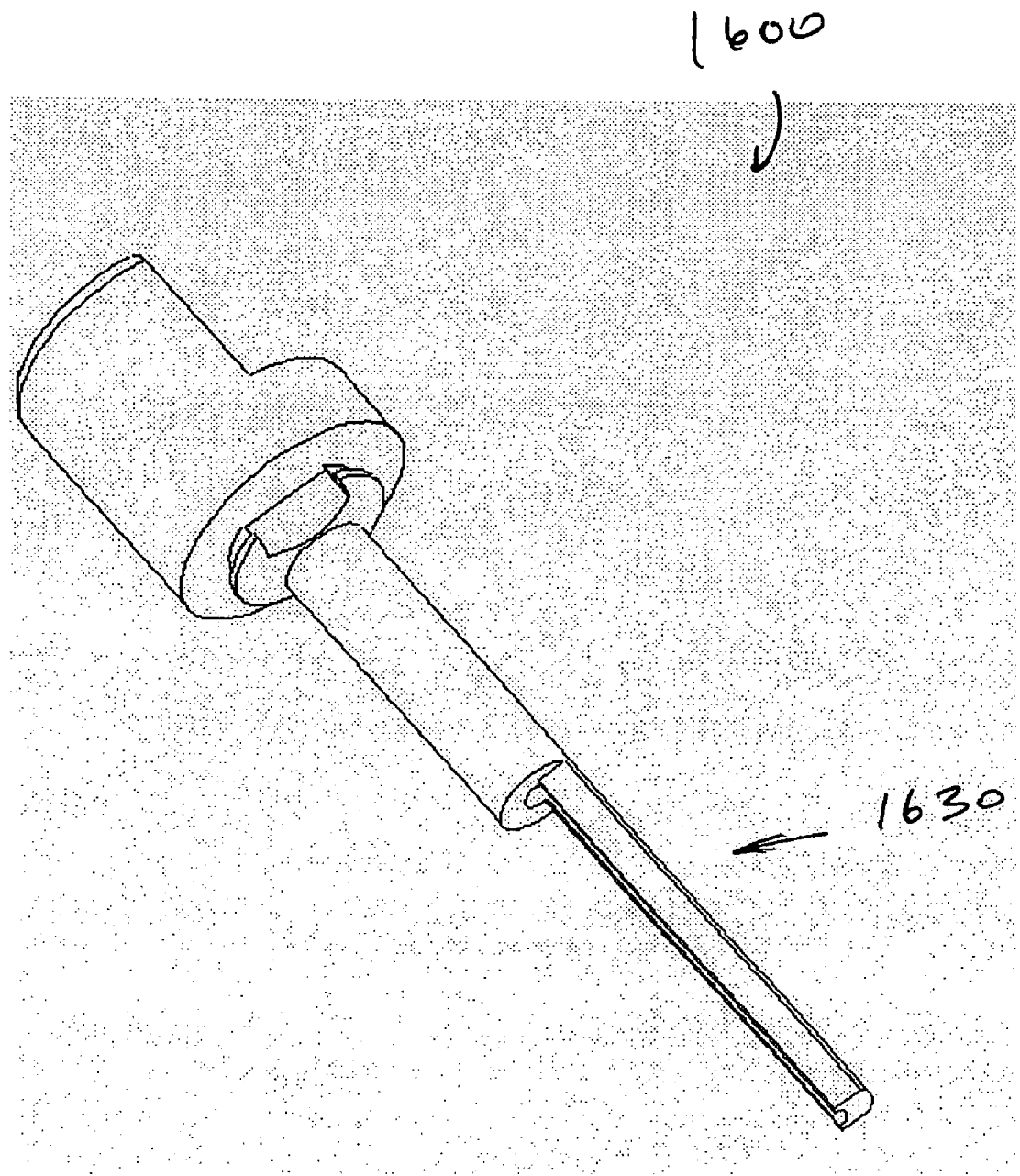
FIG. 63 is a perspective view of an extension member of the injection system of FIG. 53.

FIG. 62 is a perspective view of the needle hub driver 1602. The through hole 1606 provides retention or access for the needle 1601, as shown in FIG. 53. The needle 1601 is inserted through the hole 1606 and may rest against the side of an extension member 1630 shown in FIG. 63, which provides lateral support to the needle 1601. The needle 1601 can be coupled, or connected, to the needle hub driver 1602 using current manufacturing methods, such as molding, insert molding, welding, interlocking, sealing, or light-cure adhesive technologies. The needle hub driver 1602 is connected to the housing 1604 shown in FIG. 53 in a way that allows for the needle hub driver to rotate while the housing remains static by having a projection, e.g., flange 1610, that engages an inner feature, e.g., groove 1611, in the housing 1604 as shown in FIG. 56. The extension 1630 can be visually seen through the assembly by making the housing 1604 out of a clear material or by having a skeleton-like structure. The extension 1630 can be aligned with the outlet of the needle to provide a visual guide to the user while the needle 1601 is inserted in the site. The anti-rotational feature 1632 engages the driving device to rotate the needle 1601.

Accordingly, in the embodiments described above, a flexible protective sleeve for needle applications has an elastic feature that allows for the retraction and expansion of the sleeve to cover the needle at all times if desired. In some cases the needle preferably is never uncovered, even right after it is removed from the site. Covering the needle protects the patient and user, while also protecting the needle from bending. The flexible sleeve can be use for needles that require rotation such as intraosseous injections, or needles that are pushed into the site. The flexible protective sleeve in one embodiment can be part of the needle hub assembly, and in another embodiment can be part of the handpiece. The flexible protective sleeve can prevent injuries without changing injection techniques. Accordingly, in one embodiment, the sleeve provides relatively instant coverage of the needle as it is inserted or removed from the site, prevents the needle from bending during use, and protects the patient and user while using or disposing needles. The sleeve can also be used to control the depth of insertion of a drill or a file and/or to induce pressure at the topical site. The sleeve can also be used to cool down the tissue to reduce pain, by applying a cooling agent to the sleeve directly by way of ethyl chloride or a freon.

In one method of operation, one uses the needle with flexible protective sleeve for injection applications. The embodiment with rotating needle capabilities is attached to a driving device, such as a dental handpiece, or any other suitable type of apparatus that rotates or oscillates the needle. To initiate operation, the distal surface of the protective sleeve may be immerged in topical solution and/or cooling agent to numb the soft tissue prior to inserting the needle. The device is compressed against the tissue, causing the proprio-receptors to fire and thereby reduce pain during needle insertion. As the compression force is increased, the sleeve begins to slide upwardly while the needle penetrates the site. Once the needle has been adequately penetrated, the medication is introduced. Then, the needle is removed from the site, and the sleeve begins to move automatically downwardly covering the length of the needle the instant the needle disengages the tissue. To prevent the sleeve from retracting, the operator locks the sleeve back in the housing and disposes of the needle in an appropriate receptacle. In another method, the protective sleeve is connected or is used with an embodiment that doesn't have rotating capabilities, such as a syringe or a custom device as shown in FIGS. 51A-51B using the same or similar method.

Accordingly, in one embodiment, a needle hub assembly or handpiece comprises a flexible protective sleeve at its distal end to cover the needle. A middle structure houses the flexible feature or component. At the proximal end, an engaging feature connects to a driving component and/or to an ampoule connection. In some cases, from time of packaging removal all the way through disposal of the needle, the whole length of the needle is covered. The needle preferably is prevented from bending. The patient and user are preferably protected by the sleeve. The protective sleeve preferably provides a depth control feature to guide the user during tool insertion. The needle holder can provide an alignment feature to the needle outlet to guide the user once the needle is inserted. The flexible sleeve provides enough pressure against the tissue or means to carry topical gel or cooling agent to allow for topical anesthetic techniques.

3. Removable Front End

Figure 63A:
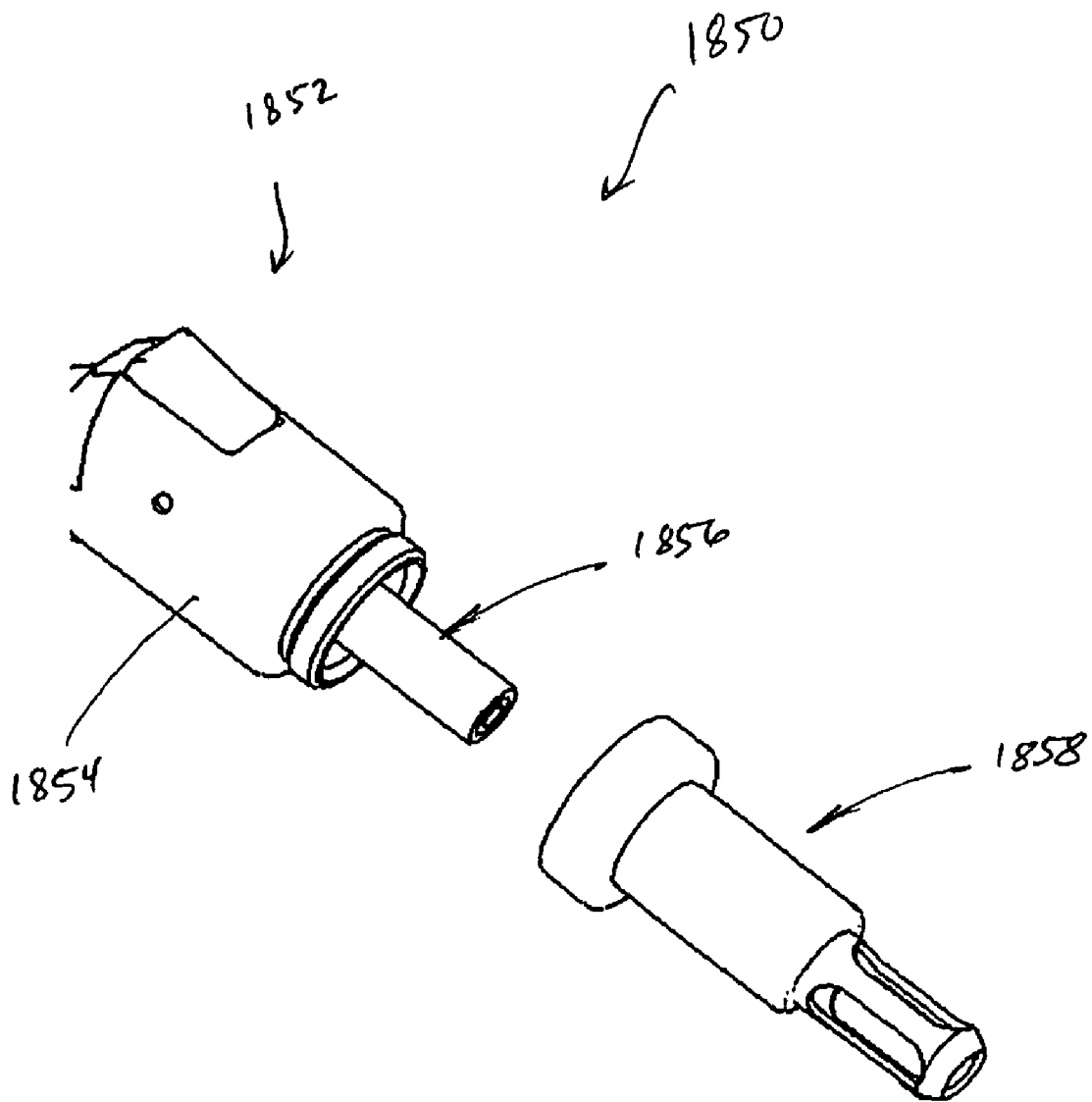
FIG. 63A is a perspective view of an injection system handpiece having a main body portion and a detatchable front end portion.

As shown in FIG. 63A, in one embodiment, an injection system 1850 comprises a handpiece 1852 having a main body portion 1854, a collet mechanism 1856, and a detachable front-end portion 1858. The front-end portion 1858 of the injection system 1850 can be removable, e.g., for autoclaving purposes. If the main body portion 1854 does not come in direct contact with a patient during a procedure, then only the front-end portion 1858 needs to be sterilized after each injection. A quick connect-disconnect front-end portion 1858 can be manufactured relatively inexpensively compared with the costs for manufacturing the entire system 1850. Accordingly, users may wish to purchase one or more front-end portions 1858 at a relatively low cost to be able to satisfy the quantity of injections needed during a given day. In one embodiment, the front-end portion 1858 can be part of a disposable packaging. In some embodiments, front-end pieces 1858 can be disposable, which may eliminate the need for autoclaving.

C. Delivery Mechanisms

1. Cartridges

Figure 64:
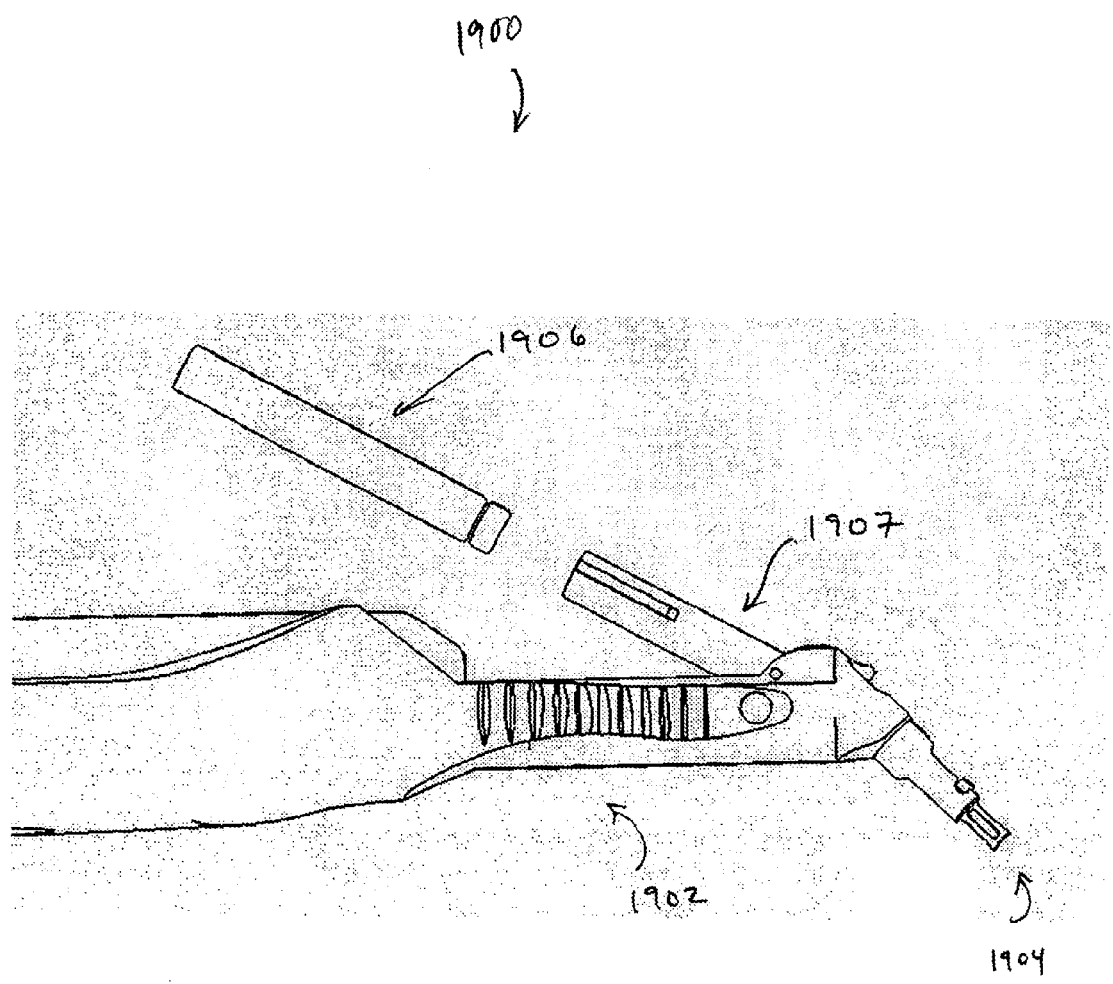
FIG. 64 is an exploded perspective view of another embodiment of an injection system, having a handpiece, a tool, a tool actuating mechanism, a protective sleeve, and a dispensing mechanism with a cartridge and a manipulatable cartridge receiving portion of the handpiece.
Figure 64A:
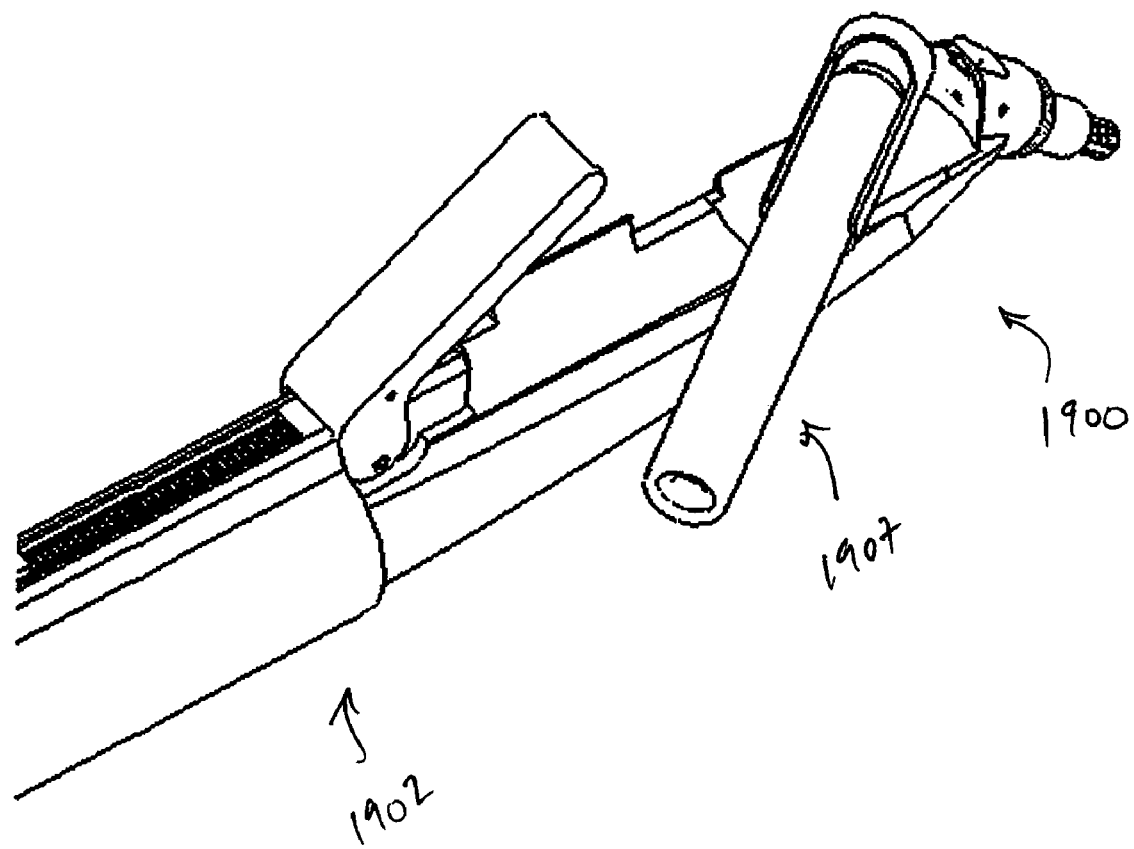
FIG. 64A is an exploded perspective view of another embodiment of an injection system, having a handpiece, a tool, a tool actuating mechanism, a protective sleeve, and a dispensing mechanism with a cartridge and a manipulatable cartridge receiving portion of the handpiece.
Figure 65:
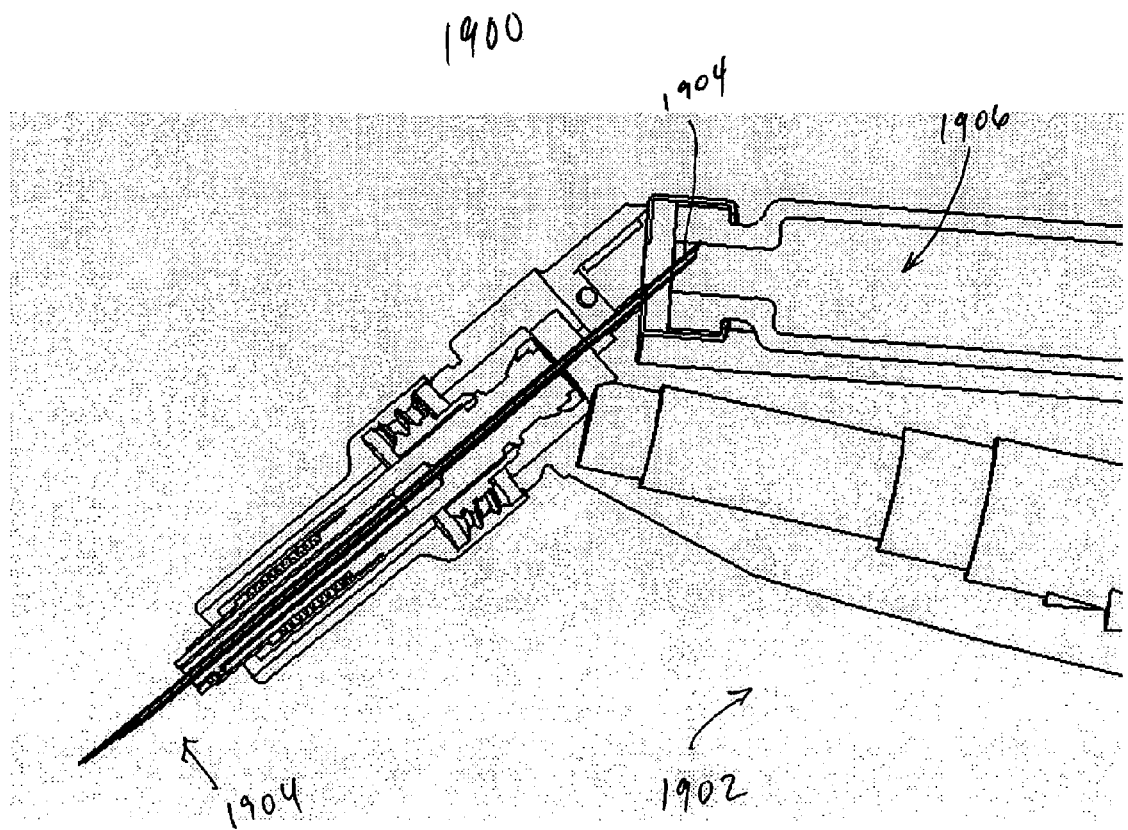
FIG. 65 is a sectional view of part of the injection system of FIG. 65, showing the dispensing mechanism with the tool coupled directly to the cartridge.
Figure 66:
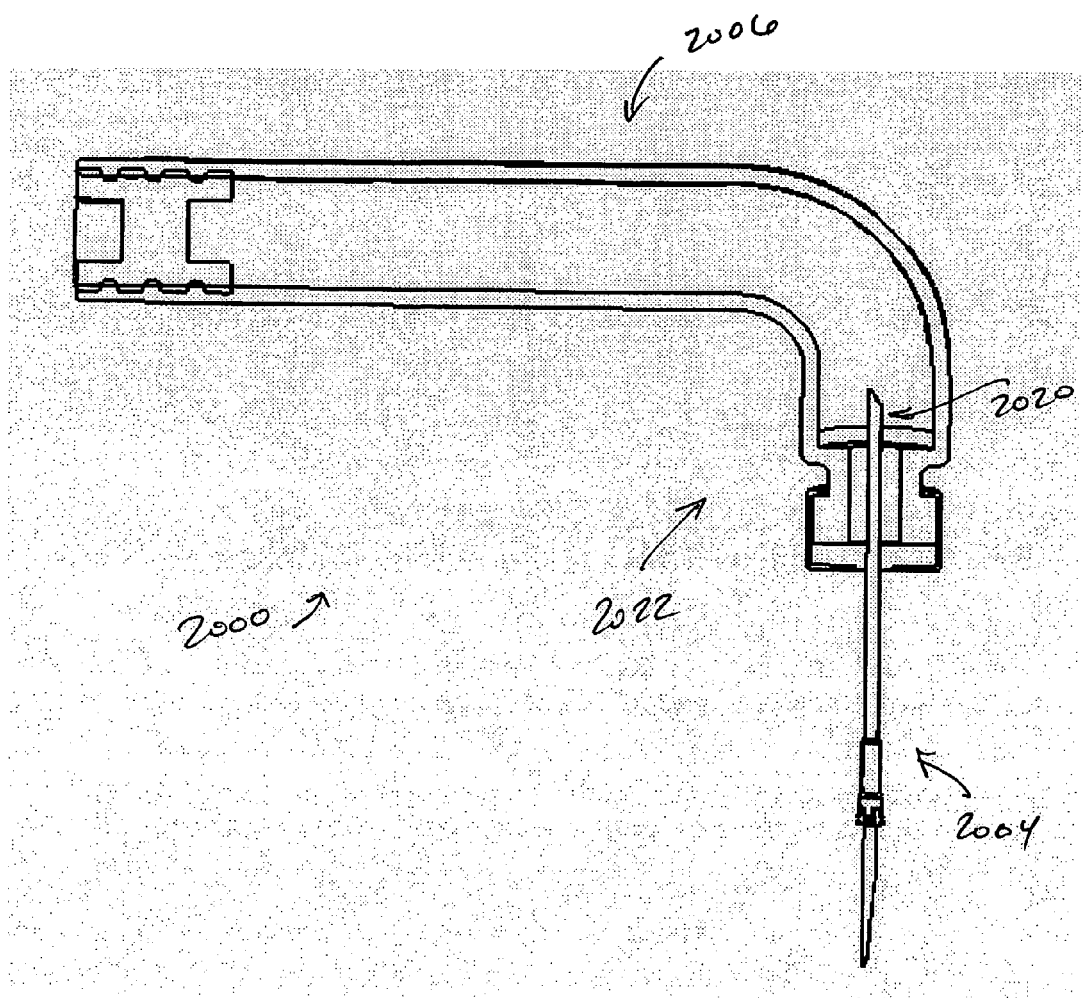
FIG. 66 is a schematic partial sectional view of another embodiment of a cartridge for and injection system, having an angled portion.

As shown in FIGS. 64-65, in one embodiment of an injection system 1900, a cartridge 1906 is loaded into a cartridge receiving mechanism 1907 that is tilted to receive the cartridge 1906 and then snapped into position in a handpiece 1902. The tilting mechanism can move towards the top of the handpiece, as shown in FIG. 64, or it can swivel towards the side of the hand piece, as shown in FIG. 64A, to reduce the distance between the lever and the body of the handpiece and allow for a lower profile. The sleeve that holds the ampoule in the tilting mechanism can be coated with reduced friction coating to prevent galling between parts. The cartridge 1906 can contain medication, solution, fluid, gel, composites, paste, or any other substance suitable for irrigation or delivery to the injection site. In some embodiments, the proximal end of a tool 1904 penetrates directly into the cartridge 1906 at an angle. In another embodiment of an injection system 2000, shown in FIG. 66, a cartridge 2006 has an angled distal end 2022 that allows a proximal end 2020 of the tool 2004 to penetrate into the distal end 2022 of the cartridge 2006 at an angle of approximately 90 degrees. The angled or bent cartridge 2006 can allow for a wide range of handpiece axis angles.

2. Delivery

Figure 67:
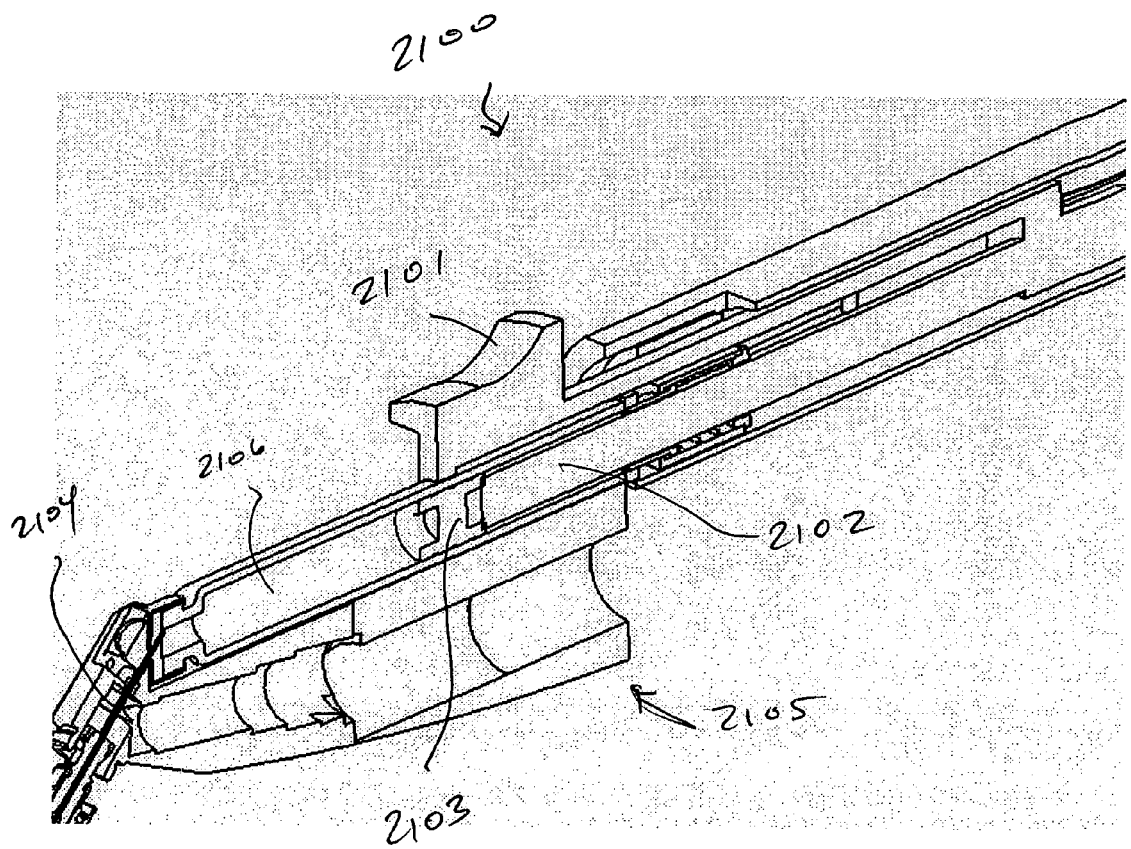
FIG. 67 is a perspective sectional view of one embodiment of an injection system, having a handpiece, a tool, a housing for a tool actuating mechanism, and a dispensing mechanism with a cartridge, a plunger and a push rod.
Figure 68:
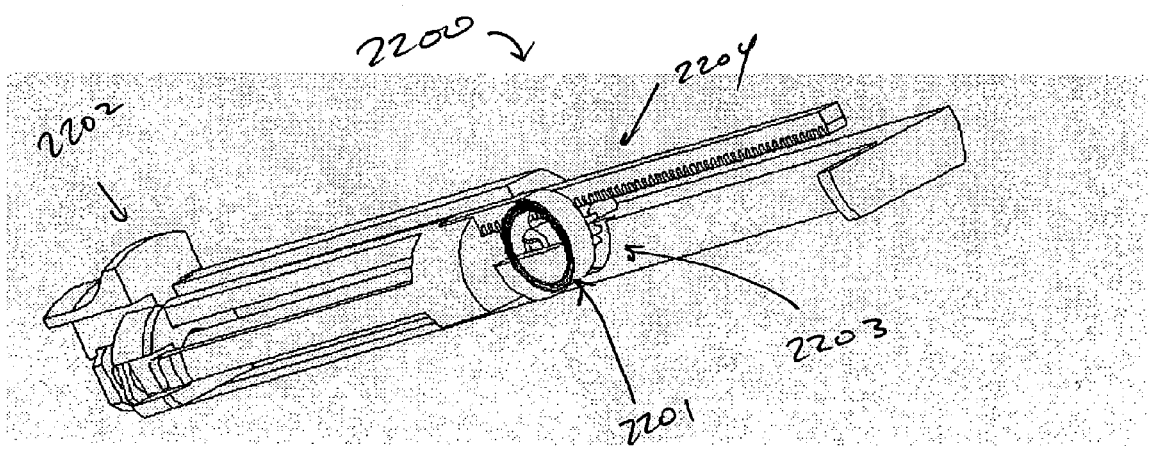
FIG. 68 is a perspective view of another embodiment of a portion of a dispensing mechanism for an injection system, having a spring, a gear, and a rack.
Figure 69:
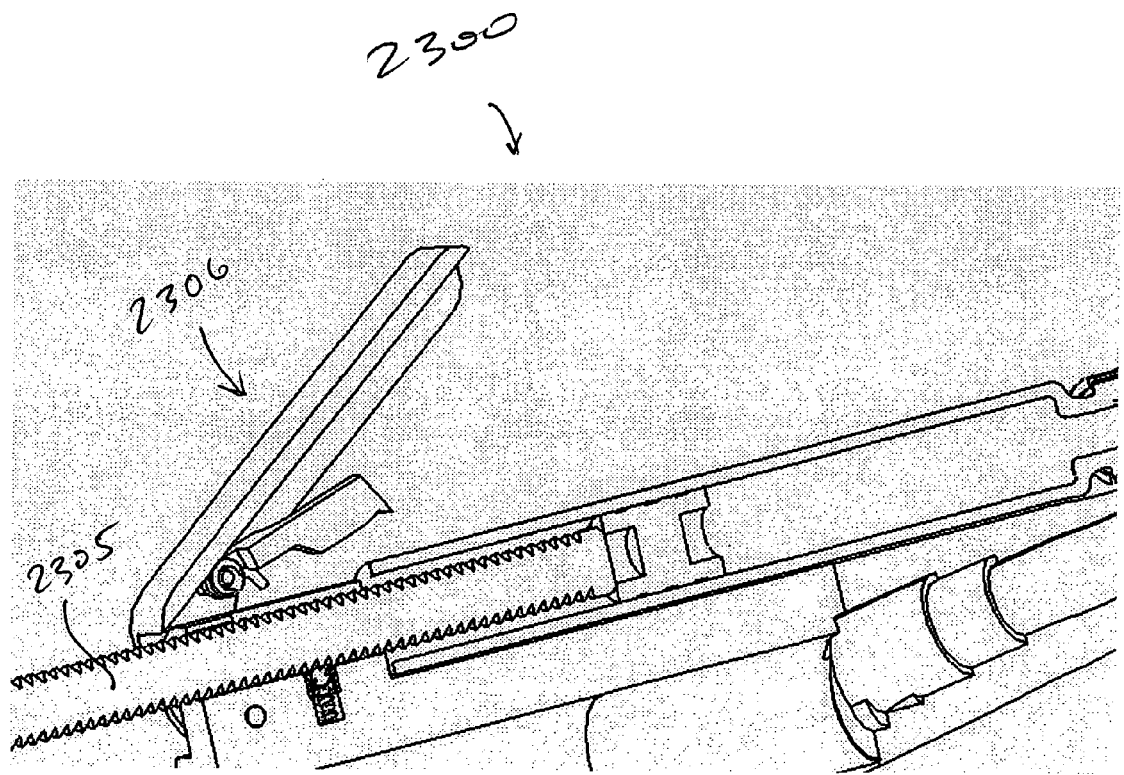
FIG. 69 is a perspective partial sectional view of another embodiment of a dispensing mechanism for an injection system, having a gear rack and lever assembly.

The contents of a cartridge can be delivered in any suitable manner. For example, as shown in FIG. 67, in one embodiment of the injection system 2100, the contents can be delivered manually with a lever 2101 and a push rod 2102. In another embodiment of an injection system 2200, as shown in FIG. 68, the contents can be delivered mechanically with a power spring 2201 and gear system as described above with reference to FIGS. 1-17. In another embodiment of an injection system 2300, as shown in FIG. 69, the contents can be delivered with a manual delivery as described further below. In other embodiments, the contents can be delivered with an electrically driven lead screw and/or gear. In still other embodiments, an air driven lead screw and/or gear can be used. One preferred embodiment is a completely mechanical system, such as, for example, injection systems 2100 and/or 2300, that allow for manual delivery. A manual delivery system can advantageously reduce the risk of accidental overdosing that may be associated with some automatic systems. Additionally, mechanical systems can allow the dentist to be completely in control of the amount of anesthetic to be delivered. Mechanical systems can also have a different regulatory approval process than automatic systems. Additionally, a manual system can provide increased tactile feel compared with some automatic systems.

In one embodiment of an injection system 2100, as shown in FIG. 67, a lever 2101 and a push rod 2102 are coupled for dispensing a cartridge 2106 of solution. The lever 2101 can be located on the top, or on the side 2102 of a handpiece 2105 body. The user moves the lever towards the front or distal portion of the handpiece 2105 making the rod 2102 contact the cartridge plunger 2103, which delivers the medication through a tool 2104.

As shown in FIG. 68, another medication delivery option 2200 is a push rod and lever combined with a gear and rack assembled with a power spring. The power spring 2201 is wound up when lever and rod combination 2202 is locked in the handpiece body. The user unlocks the lever, which makes the power spring unwind. The spring preferably rotates the gear 2203, making the rack 2204 move towards the front end of a handpiece. The end user can also overcome the power spring force by manually moving the lever forward. The rack 2204 is connected to the rod, which contacts a cartridge plunger that delivers the medication.

Figure 69A:
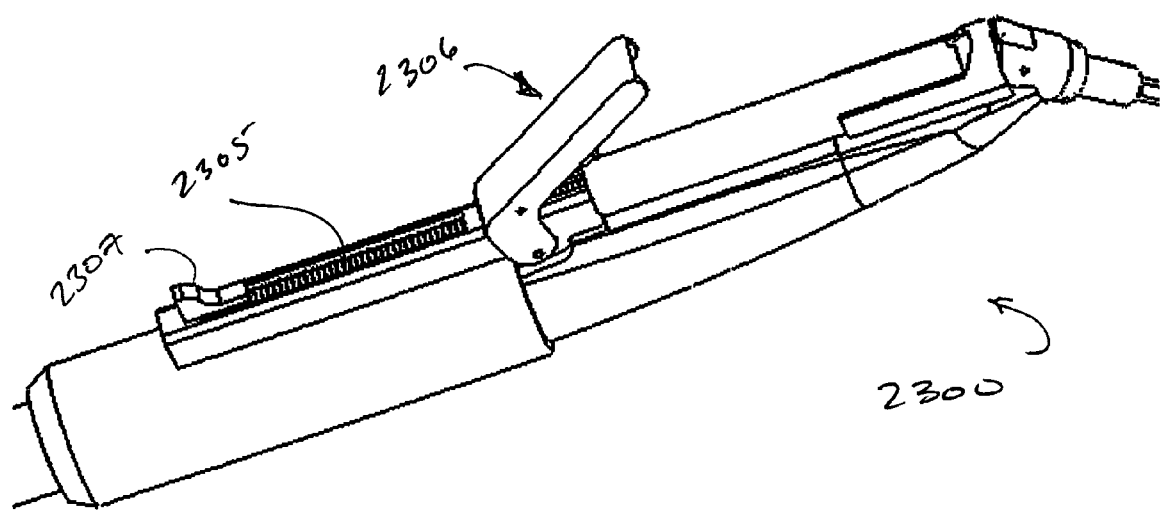
FIG. 69A is a perspective view of the dispensing mechanism of FIG. 69 having a cover.

As shown in FIG. 69, the delivery of the medication can also be done in one embodiment of an injection system 2300, with a gear rack 2305 and a spring-loaded lever 2306 assembly. FIG. 69A shows the gear rack 2305 with a cover. The cover can reduce the chances of a glove getting stuck in the rack. As shown in FIG. 69A, a lever 2307 is connected to the rack 2305 to assist in removing the rack from the ampoule. The top surface of the cover can have markings, such as a scale, and the lever 2307 can be used to indicate the amount of solution being delivered. Solution is delivered as the end user depresses the spring-loaded lever 2306. The rack 2305 assembly moves forward to contact a cartridge plunger that delivers the medication. In still other embodiments, the delivery of the medication can be done with an air driven mechanism, with an electronic mechanism, or with a motorized dispensing mechanism.

3. Cartridge Rotation

As shown in FIGS. 70-74, according to one embodiment, an injection system 2400 comprises a rotary mechanism 2402. The rotary mechanism 2402 preferably is capable of rotating a cartridge 2404. Rotation of the cartridge 2404 can minimize the risk of a torsional overload that may take place at the interfaces of needle 2406, hub 2408 and collet 2410 assemblies. A torsional overload can result in the debonding of a needle 2406 with resptect to a hub 2408 and/or a needle hub assembly 2408 can slip inside a collet 2410 and thereby reduce the needle RPM. Reducing the needle RPM can make drilling inside bone difficult, causing the needle 2406 to stuck inside the bone. Thus, to minimize frictional losses that may take place between the needle 2406 and ampoule 2404, the injection system 2400 of the illustrated embodiments includes a mechanism for cartridge rotation.

The embodiment of FIGS. 70-74 illustrates a passive mechanism 2402 in which the ampoule 2404 sits on one or more rollers 2412, or any other bearing suitable for allowing rotation. As the needle 2406 rotates, the ampoule 2404 will also rotate freely as there is a frictional coupling between the needle 2406 and the ampoule 2404 via a silicone stopper 2414.

Figure 73:
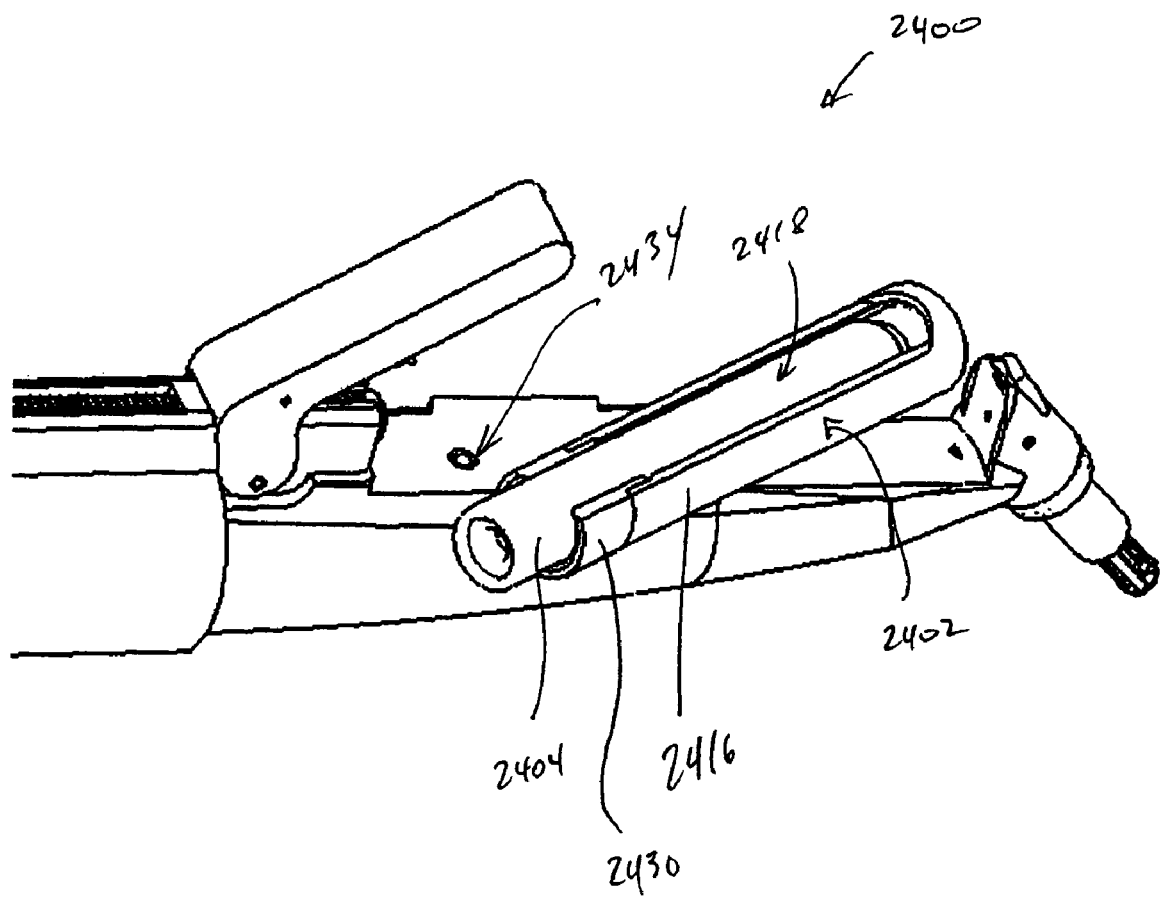
FIG. 73 is a perspective view of the injection system of FIG. 70.

As shown in FIG. 73, an outer shell 2416 of the passive mechanism 2402 can swivel up or sideways to facilitate the loading of the cartridge 2404. The shell 2416 can have an opening 2418 at the top or side to allow the end user to view the cartridge 2404 and determine the amount of medication that is being delivered. The shell 2416 can also be coated with friction reduction coating to reduce or prevent galling of cartridge 2404 and or rollers 2412. The shell can also be part of the handpiece body, in which case one or more rollers are placed within the cartridge cavity.

Figure 70:
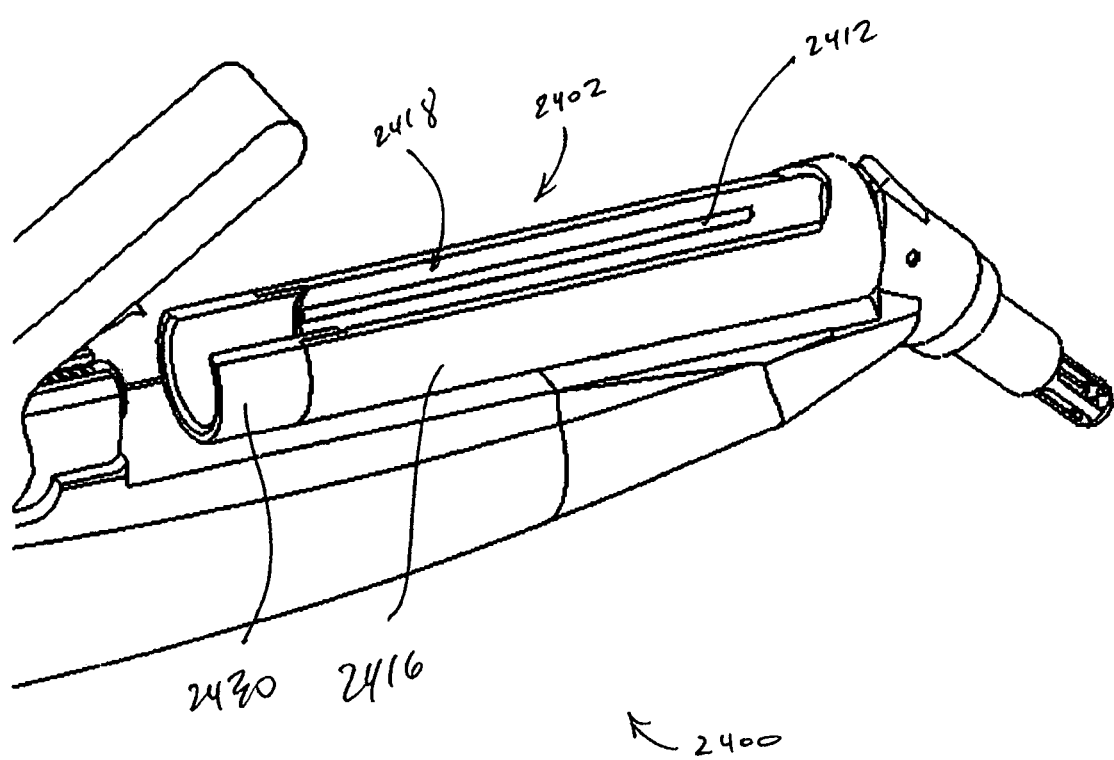
FIG. 70 is a perspective view of another embodiment of an injection system, having a roller bearing mechanism.
Figure 71:
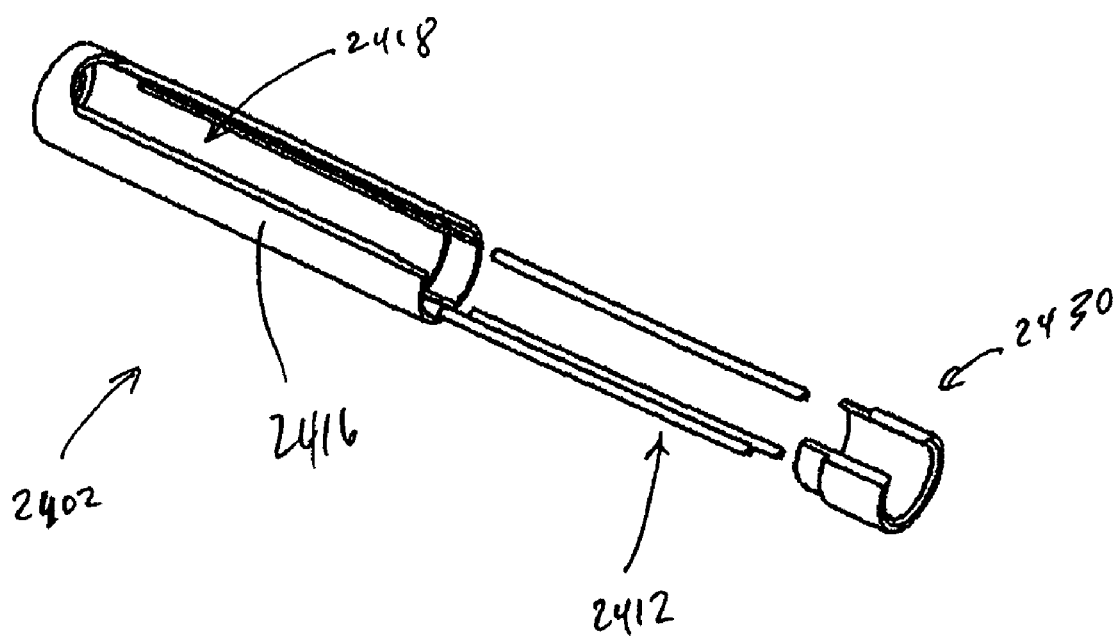
FIG. 71 is an exploded view of the roller bearing mechanism of the injection system of FIG. 70.

In one embodiment, the rollers 2412 can be retained in a cage. In another embodiment, the rollers 2412 can be assembled inside the outer shell 2416, as shown in FIGS. 70-71. In another embodiment, ball bearings can be positioned in different linear locations within the shell 2416. The balls can be placed between the shell 2416 and an inner ring like some other ball bearings that are commercially available, or in any other suitable fashion.

Figure 72:
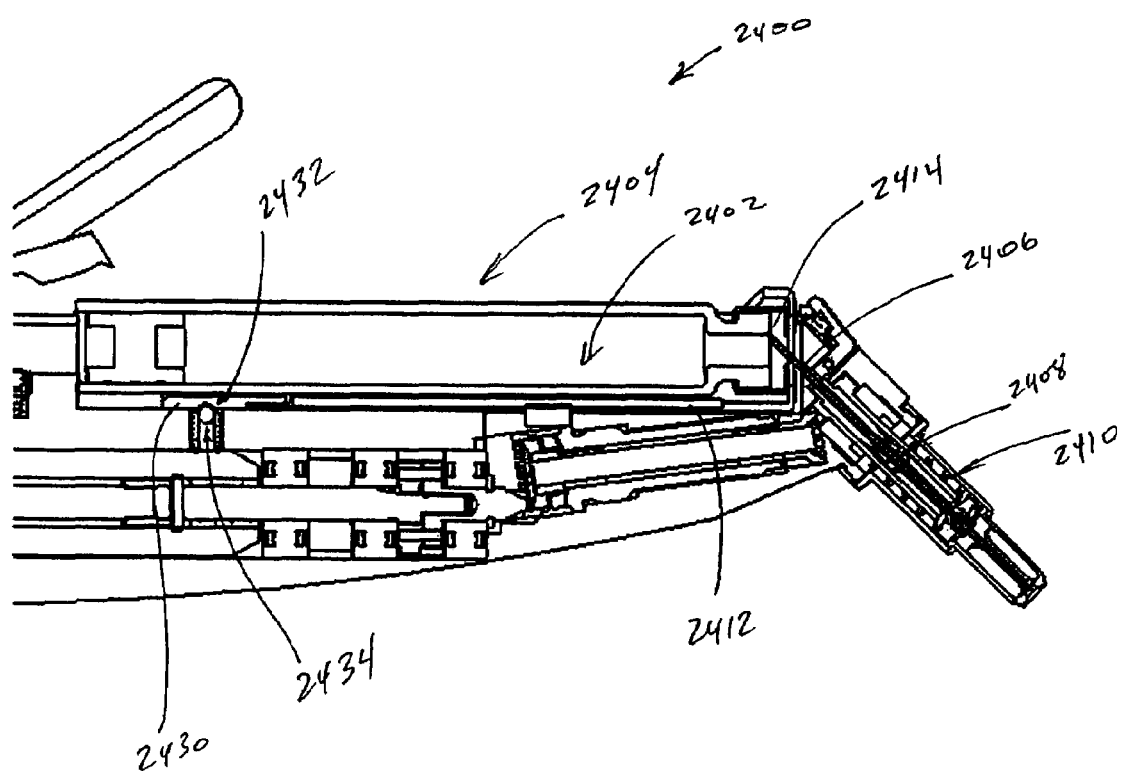
FIG. 72 is a sectional view of the injection system of FIG. 70.

A retainer 2430 is press fitted, laser welded, or otherwise coupled to the shell 2416. As shown in FIGS. 72-73, the retainer 2430 can have a rounded indentation 2432 to allow for a ball plunger 2434 to lock the shell 2416 in its place and prevent the shell 2416 from moving during use.

Figure 74:
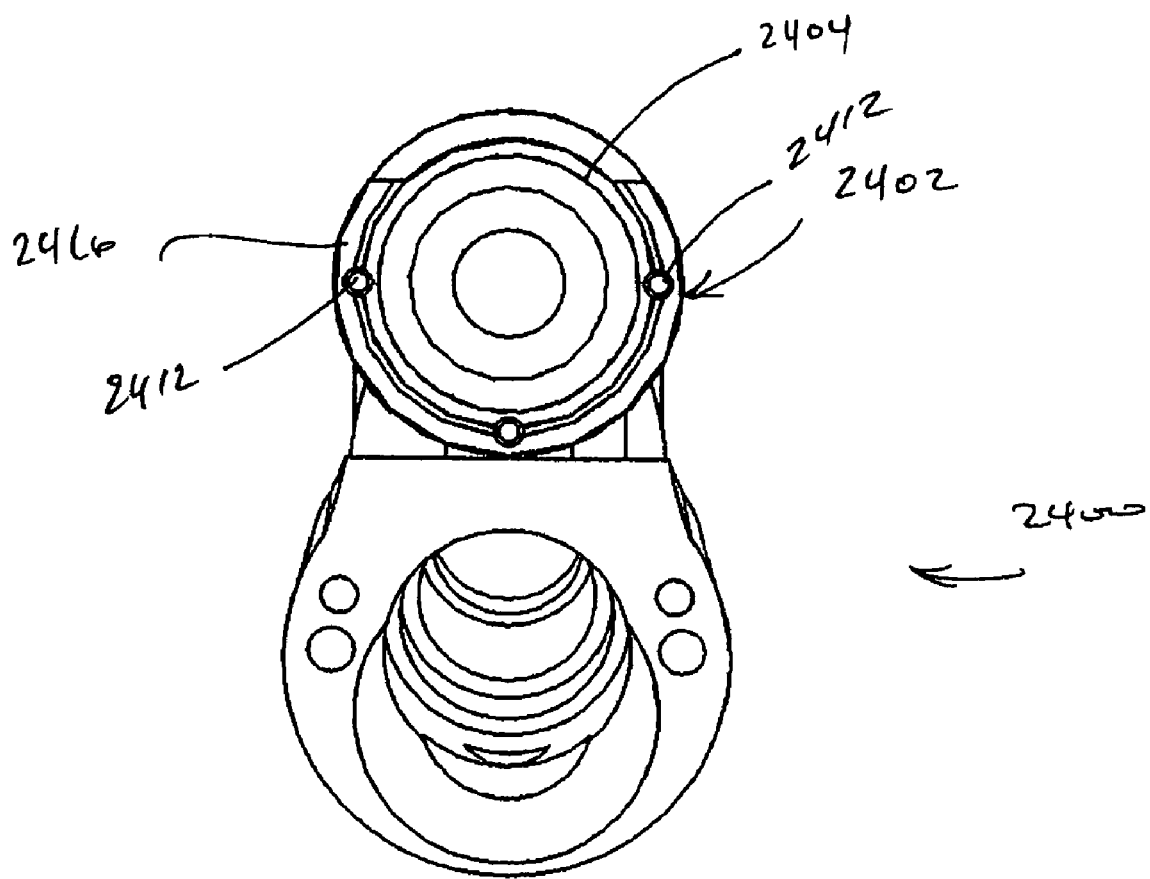
FIG. 74 is a view of the roller bearing mechanism of the injection system of FIG. 70.

As shown in FIG. 74, rollers 2412 preferably are placed inside the shell 2416 or within the handpiece body to create a diameter that is slightly larger than the outside diameter of the cartridge 2404 to allow the cartridge 2404 to have free rotational movement.

Figure 75:
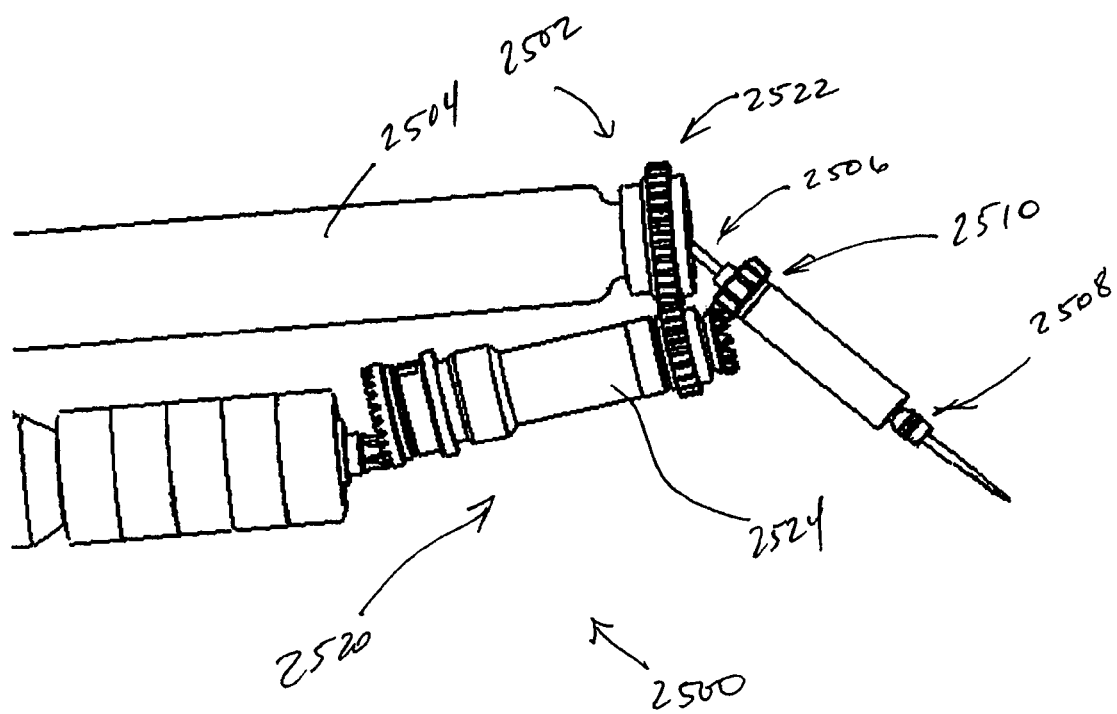
FIG. 75 is a perspective view of a gear motor mechanism of another embodiment of an injection system.
Figure 76:
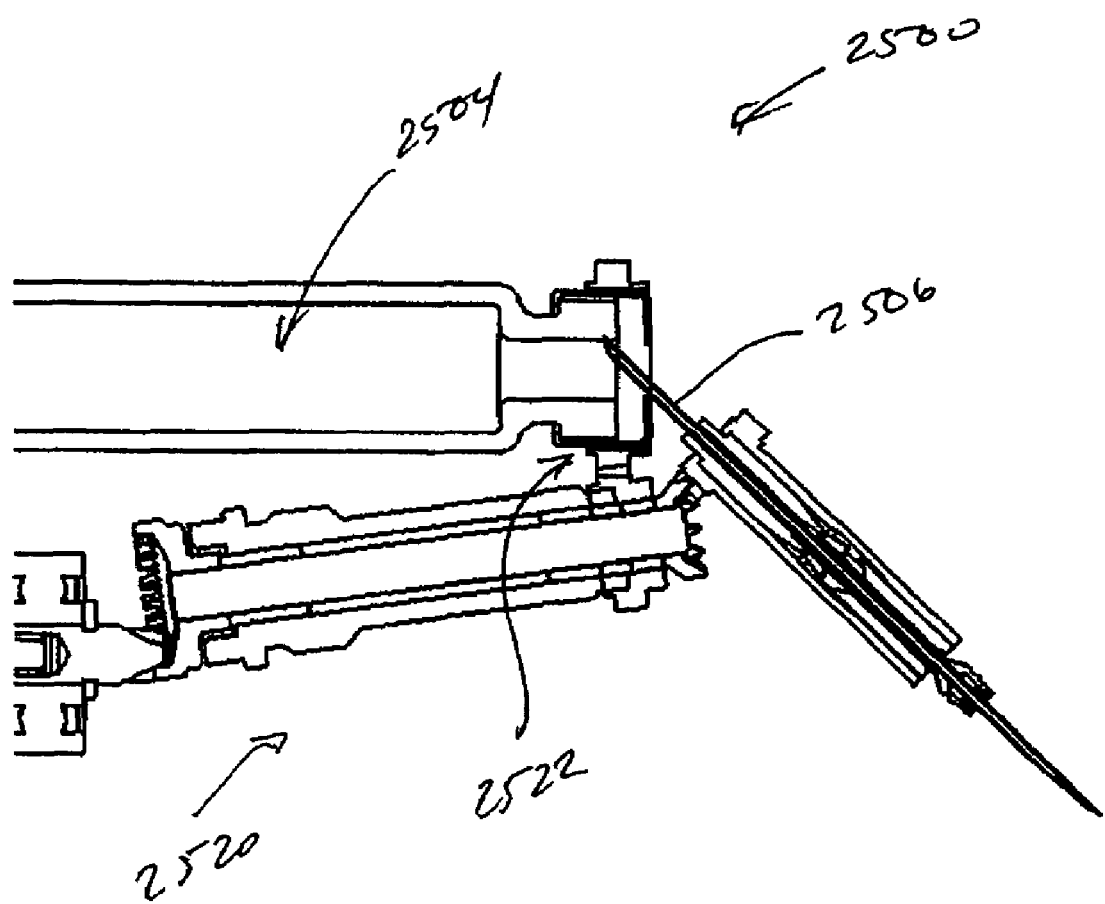
FIG. 76 is a sectional view of the embodiment of FIG. 75.

FIGS. 75-76 illustrate an injection system 2500 having an active mechanism 2502 for rotating the ampoule 2504. In this embodiment, the ampoule 2504 is connected to a gear train 2520 via a gear 2522. According to one embodiment, the ampoule 2504 will continually rotate as a needle 2506 rotates to prevent a torsional overload.

In the embodiment illustrated in FIGS. 75-76, the cartridge rotates by having its front end closely fitted inside the gear 2522 that mates with an intermediate gear mechanism 2524 that also rotates the chuck or collet 2510 that holds the needle 2506. As the needle 2506 rotates, the cartridge rotates at the same time. Alternately, the cartridge 2504 can rotate by having its face pushed up against the face of the gear 2522 using the force generated by the push rod of the delivery mechanism. Accordingly, torsional overload that can take place at the interfaces of needle 2506, hub 2508 and collet 2510 assemblies preferably can be avoided.

Figure 77:
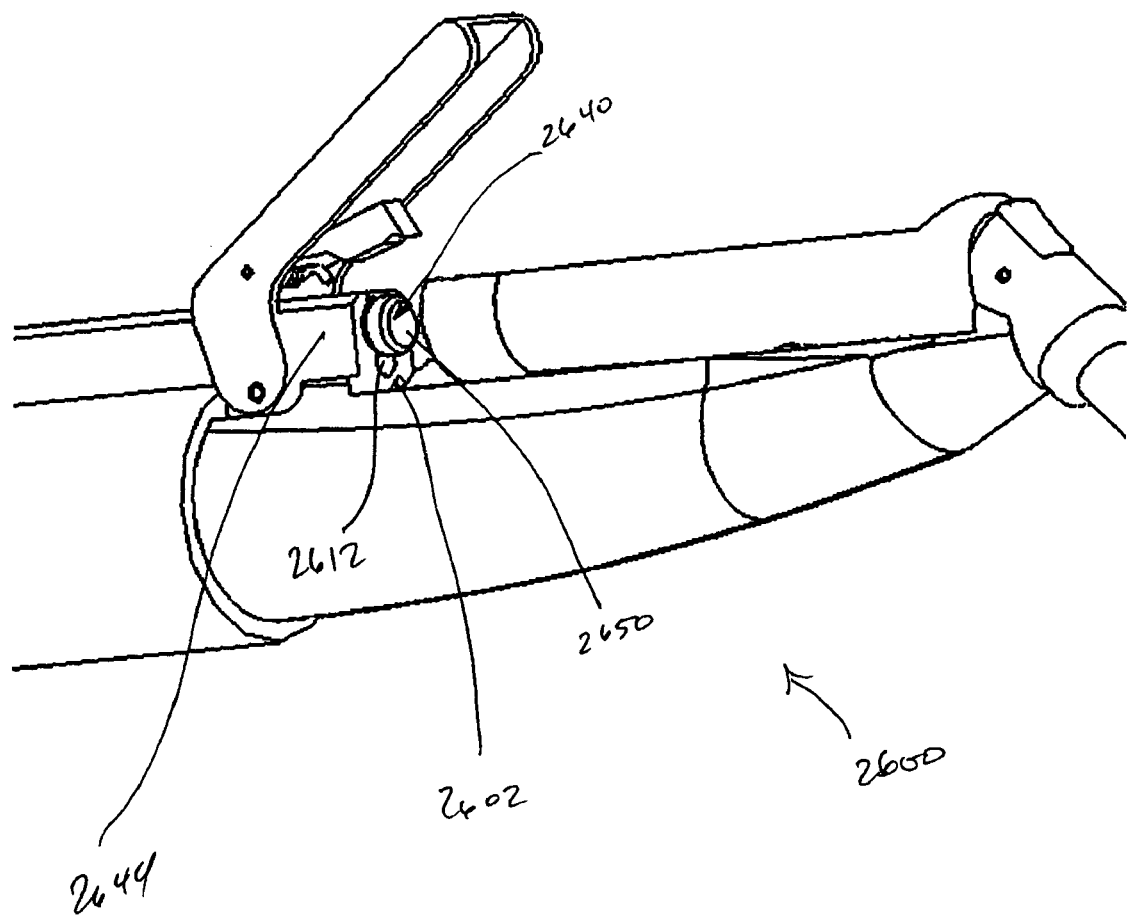
FIG. 77 is a perspective view of another embodiment of an injection system having a rotating push rod mechanism.
Figure 78:
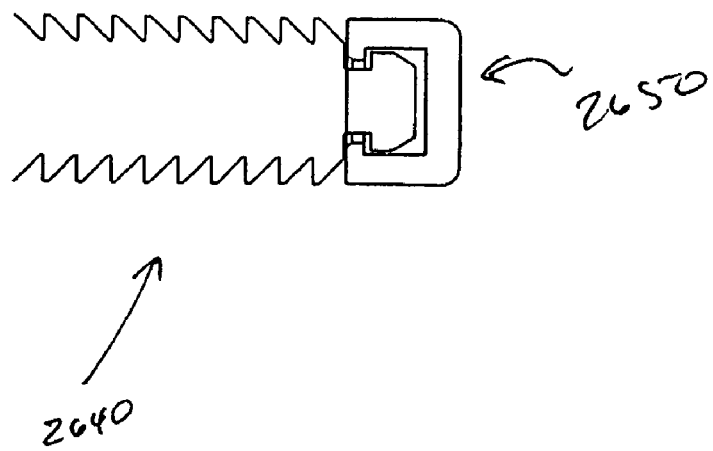
FIG. 78 is a sectional view of another embodiment of an injection system having a push rod mechanism with a rotating tip.
Figure 79:
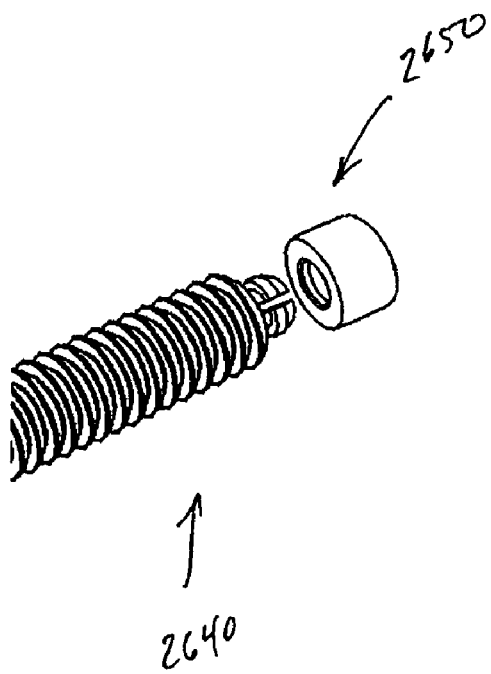
FIG. 79 is a perspective view of the push rod mechanism of FIG. 78.

As shown in FIGS. 77-79, in some embodiments, an injection system 2600 comprises a push rod 2640 for contacting a cartridge plunger (not shown), and a rotary mechanism 2602 to prevent torsional overload between the mating surfaces of the push rod 2640 and cartridge plunger of the cartridge or ampoule (not shown). As the cartridge rotates the push rod 2640 can also rotate freely by incorporating one or more rollers 2612 and/or ball bearings within a push rod housing 2644 or by inserting a loosely fitted tip 2650 at the end of the push rod 2640 that the tip 2650 can rotate as it makes contact with a rotating surface of the cartridge plunger. In one embodiment, the push rod 2640 is on roller bearings 2612 or ball bearings to minimize frictional forces on the cartridge while the rod 2640 is pushing against the cartridge plunger. In one embodiment, the push rod 2640 can be assembled with the tip 2650 that freely rotates as it is pushing up against the face of the cartridge plunger during medication delivery.

In some embodiments, an advantage of the aforementioned mechanisms is to reduce or eliminate static friction between the needle and the cartridge, and to introduce dynamic friction. Dynamic friction is lower than the static friction, which preferably results in lower torsional losses, thereby reducing the chances of debonding and/or needle slippage inside the collet.

D. Advantages of Some Embodiments

Many features and advantages have been described in connection with the embodiments disclosed herein. In one embodiment, a gripping mechanism for needles, files, drills, burrs, and/or endodontics tools can be attached to and/or be part of a driving device, static device, syringe, or intraosseous injection system. The mechanism preferably squeezes the tool using a collet or chuck device, which allows for a quick connect/disconnect of the tool. In one embodiment, the mechanism is connected to a motor having a torque limiting feature and/or an automatically reversible rotation at a predetermined amount of torque. These features preferably protect the patient and the end user from injuries related to applying excessive torque to the tool. The mechanism, preferably permits the proximal end of the needle or tool bit to penetrate directly into an ampoule or cartridge without the need for additional intermediate pieces. These embodiments can eliminate the need for an additional needle or device, providing a cost effective, easy to use, and safe product. The mechanism preferably also permits the use of hollowed-out files or drills that can penetrate the ampoule or cartridge. As explained above, the cartridge can contain a wide range of composites or medications, including antibiotics. The file or drill can also penetrate an ampoule that contains liquid solutions to prevent overheating of the site and/or to irrigate the canal. Alternatively, the mechanism can be attached to, or be part of, a syringe for static needle or tool applications to facilitate the loading and/or removal of the tool or working piece. The mechanism is not limited to use with intraosseous injection systems. The mechanism can also be used in other types of injections where the tool or working piece is rotated, oscillated, inserted and/or pushed. The mechanism is also broadly usable for gripping a wide range of endodontic tools, medical tools, and/or veterinary medicine tools. Accordingly, in one embodiment, the gripping mechanism preferably prevents premature dislodging of the tool, facilitates connection of the tool to the handpiece, prevents premature breakage of the tool, eliminates unnecessary components, reduces the generation of heat at the working site, and protects the patient and user during use of the handpiece. The gripping mechanism can be used for static, oscillating, and/or rotating dental applications. Some embodiments with a rotating or oscillating gripping mechanism have a driving connection. Some embodiments having a static gripping mechanism do not have a gear mechanism. The gripping mechanism preferably allows for a straightforward loading and unloading of the needle or tool using a carrier, with or without a hub. In one embodiment, the sleeve provides relatively instant coverage of the needle as it is inserted or removed from the site, prevents the needle from bending during use, and protects the patient and user while using or disposing needles. The sleeve can also be used to control the depth of insertion of a drill or a file.

Figure 7:
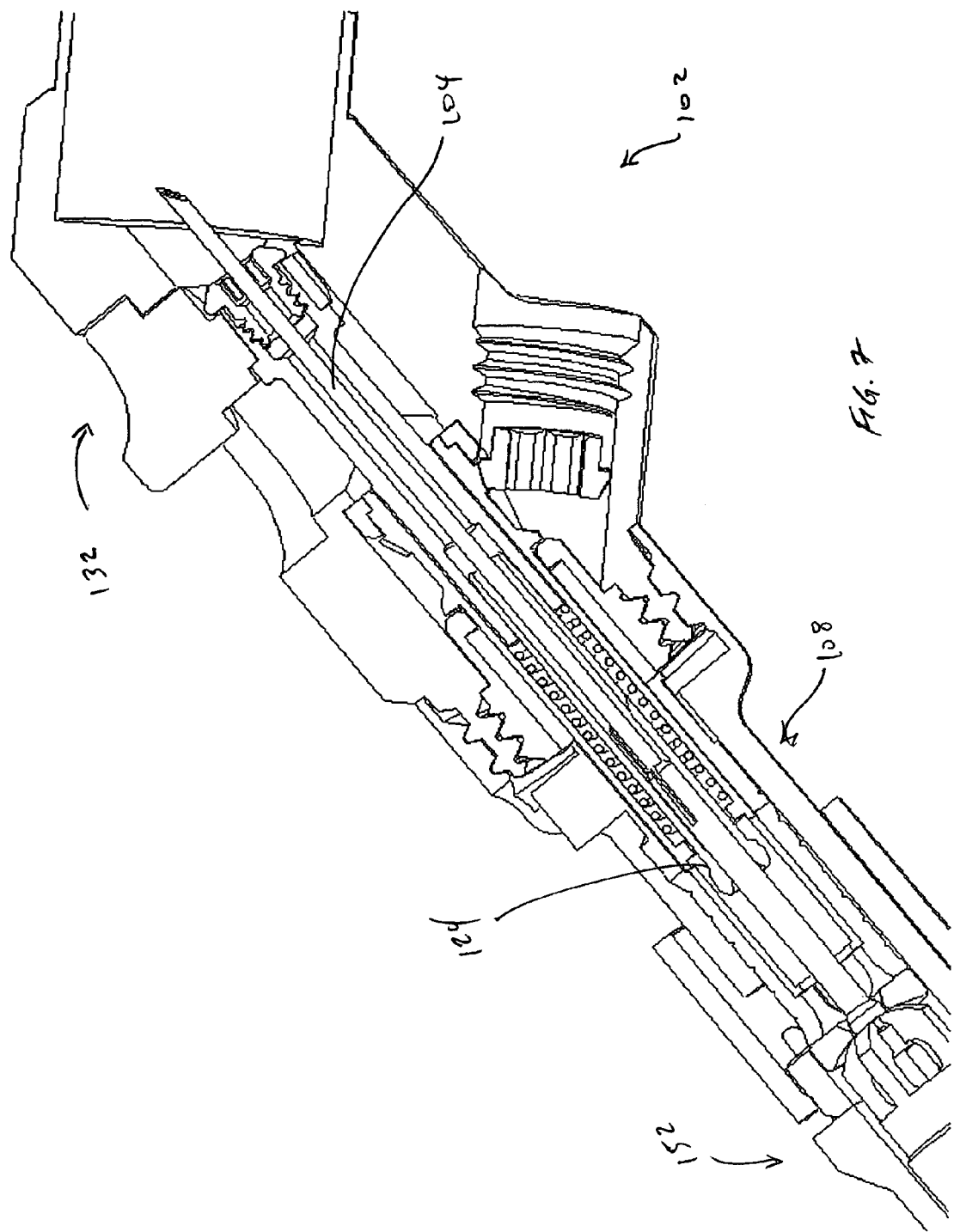
FIG. 7 is a sectional view of the tool and tool carrier assembly of FIG. 3 loading the tool into the handpiece of the system of FIG. 1, with the collet mechanism of the system closed to grasp the tool.
Figure 8:
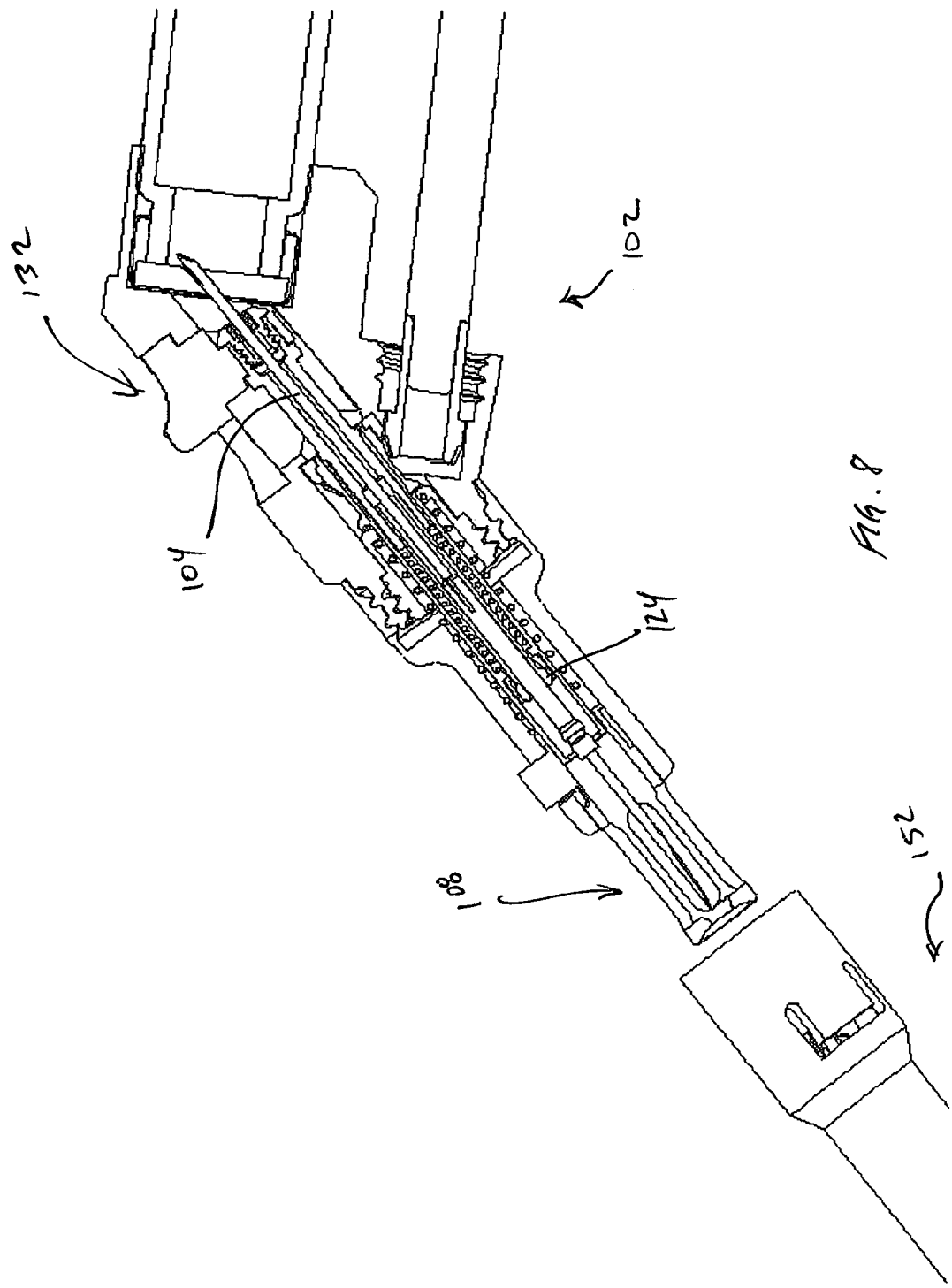
FIG. 8 is a sectional view of the tool and tool carrier assembly of FIG. 3 loading the tool into the handpiece of the system of FIG. 1, with the collet mechanism of the system closed to grasp the tool, and the tool carrier assembly partially withdrawn such that a sleeve of the system at least partially covers the tool.
Figure 80:
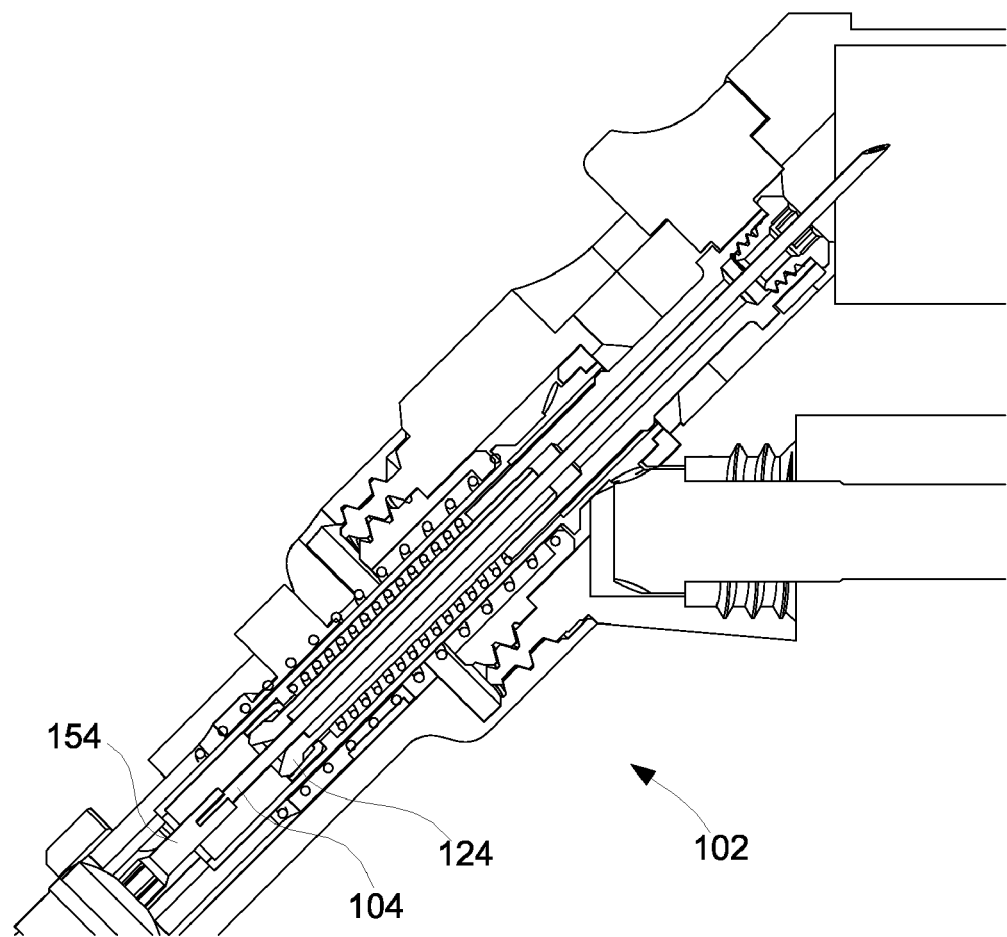
FIG. 80 is a sectional view of the tool and carrier assembly similar to the view of FIG. 7 that shows the collet mechanism of the system closed to grasp a portion of the tool not covered by the hub.

In operation one uses the gripping device for needles, endodontic, or dental tools such as endodontic files in a normal approach for injection, or any other type of dental applications. First, the gripping device is opened using a button, or any other component for opening the gripping feature chuck or collet. Then, while the button is activated, the tool is inserted into the gripping opening. A carrier can be used during the loading process to aid and protect the end user while delivering the tool into the collet. At the time when the tool reaches the desired depth, the button can be deactivated, causing the gripping feature 124 to apply hoop stresses on the outer diameter of the tool 104 as shown in FIG. 80 and/or hub 154 as shown in FIG. 7 to hold the tool 104 firmly in place. Once the application is completed, the button is activated to cause the tool to disengage the gripping device. The tool can be disposed into an appropriate receptacle with or without the use of the carrier Accordingly, one embodiment of a gripping mechanism comprises a housing having a distal end that holds an inner housing having a gripping component, an optional spring, and a retainer. The housing has a proximal end, and a body that holds a switch. In some embodiments, the housing has a motor gear shaft. The gripping mechanism preferably holds the dental tool, e.g., a needle, a file, directly as shown in FIG. 80 or through a stiff or flexible hub (e.g., the hub 154 in FIG. 7) to prevent premature dislodging. In some embodiments, the gripping mechanism has a gear element that is connected to a motor to allow for the tool to rotate or oscillate. The gripping mechanism can protect the user by having a motor that reverses the rotation when it reaches a predetermined torque to prevent breakage of the tool. The tool can be packaged and/or coupled with a carrier to assist in the loading and unloading process of the tool from the gripping mechanism. The gripping mechanism can be adapted for use with any suitable static or syringe device. The gripping mechanism preferably allows for the delivery of medications such as antibiotics, composites, and or filling material, such as guttapurcha, or irrigation solutions into the root canal through the use of the tool, e.g., a hollow file, a needle. The gripping mechanism preferably eliminates the need for hypodermnic needles and/or intermnediate components to deliver anesthesia after an intraosseous perforator penetrates the site, because the gripping mechanism permnits the direct attachment of the perforator into the cartridge and/or ampoule. [bold added for emphasis ]

The various devices, methods, procedures, and techniques described above provide a number of ways to carry out the invention. Of course, it is to be understood that not necessarily all objectives or advantages described may be achieved in accordance with any particular embodiment described herein. Also, although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, the invention is not intended to be limited by the specific disclosures of preferred embodiments herein.

What is claimed is:

1. A device for intraosseous delivery of solutions, comprising:
 a housing that receives a solution cartridge having a penetrable seal on one end thereof, the solution cartridge holding a solution therein;

a gripping device having an open position to receive a needle and having a closed position to grip the needle, the needle having a hollow bore extending therethrough from a proximal end to a distal end thereof, the gripping device holding the needle with the proximal end of the needle in the solution and with the distal end of the needle exposed for engagement with a material to be drilled;

a rotating mechanism that rotates the gripping device to rotate the needle; and a dispensing mechanism that applies pressure to the solution within the solution cartridge to force the solution from the solution cartridge through the hollow bore of the needle to eject the solution from the distal end of the needle.

2. The device as defined in claim 1, wherein the gripping device comprises a collet mechanism.

3. The device as defined in claim 1, wherein the gripping device comprises a chucking mechanism that grips the needle in a region closer to the proximal end of the needle than to the distal end of the needle.

4. The device as defined in claim 1, wherein the dispensing mechanism comprises a push rod that applies pressure to the solution within the solution cartridge.

5. The device as defined in claim 1, wherein the dispensing mechanism comprises a spring-loaded lever and a rack, and wherein the rack axially advances to reduce the volume of the cartridge as the spring-loaded lever is manually depressed.

6. The device as defined in claim 1, wherein the dispensing mechanism comprises a gear and a plunger, and wherein the plunger axially advances to reduce the volume of the cartridge.

7. The device as defined in claim 1, wherein the gripping device is configured to receive a standard type needle.

8. The device as defined in claim 7, wherein the standard type needle comprises a hub covering a first portion of the outer surface of the needle, and wherein the gripping device is configured to grip a second portion of the outer surface of the needle not covered by the hub.

9. The device as defined in claim 1, wherein the distal end of the needle comprises one or more bevels.

10. The device as defined in claim 1, wherein the rotating mechanism is configured to be coupled to an electric motor.

11. The device as defined in claim 1, wherein the rotating mechanism is configured to be coupled to an air supply.

12. The device as defined in claim 1, wherein the rotating mechanism is configured for cordless operation.

13. The device as defined in claim 1, further comprising a sleeve configured to extend over at least a portion of the needle when the needle is gripped by the gripping device.

14. A device for intraosseous delivery of solutions, comprising:

a housing that receives a solution cartridge having a penetrable seal on one end thereof, the solution cartridge holding a solution therein;

a gripping device having an openposition to receive a needle and having a closed position to grip the needle, the needle having a hollow bore extending therethrough from a proximal end to a distal end thereof, the gripping device holding the needle with the proximal end of the needle in the solution and with the distal end of the needle exposed for engagement with a material to be drilled;

a rotating mechanism that rotates the gripping device to rotate the needle; and a dispensing mechanism that applies pressure to the solution within the solution cartridge to force the solution from the solution cartridge through the hollow bore of the needle to eject the solution from the distal end of the needle, wherein the gripping device comprises a chucking mechanism that grips the needle in a region closer to the proximal end of the needle than to the distal end of the needle, and wherein the chucking mechanism comprises a radially expandable collet that expands to receive the needle and that contracts to hold the needle.

15. The device as defined in claim 14, wherein the radially expandable collet is responsive to a force to contract about the needle.

16. The device as defined in claim 15, further comprising a biasing member to bias the collet to a compressed position to contract about the needle.

17. The device as defined in claim 14, wherein the gripping device comprises a plurality of lever arms.

18. The device as defined in claim 14, wherein the solution cartridge has a first axis and wherein the needle rotates about a second axis, the second axis being at an angle with respect to the first axis.

19. The device as defined in claim 14, wherein the gripping device is configured to receive a standard type needle.

20. The device as defined in claim 19, wherein the standard type needle comprises a hub covering a first portion of the outer surface of the needle, and wherein the gripping device is configured to grip a second portion of the outer surface of the needle not covered by the hub.

21. The device as defined in claim 14, wherein the rotating mechanism is configured to be coupled to an electric motor.

22. The device as defined in claim 14, wherein the rotating mechanism is configured to be coupled to an air supply.

23. The device as defined in claim 14, wherein the rotating mechanism is configured for cordless operation.

24. The device as defined in claim 14, further comprising a sleeve configured to extend over at least a portion of the needle when the needle is gripped by the gripping device.

25. A device for intraosseous delivery of solutions, comprising:

a housing that receives a solution cartridge having a penetrable seal on one end thereof, the solution cartridge holding a solution therein;

a gripping device having an open position to receive a needle and having a closed position to grip the needle, the needle having a hollow bore extending therethrough from a proximal end to a distal end thereof, the gripping device holding the needle with the proximal end of the needle in the solution and with the distal end of the needle exposed for engagement with a material to be drilled;

a rotating mechanism that rotates the gripping device to rotate the needle; and a dispensing mechanism that applies pressure to the solution within the solution cartridge to force the solution from the solution cartridge through the hollow bore of the needle to eject the solution from the distal end of the needle, wherein the gripping device comprises a plurality of lever arms.

26. The device as defined in claim 25, wherein the gripping device is configured to receive a standard type needle.

27. The device as defined in claim 26, wherein the standard type needle comprises a hub covering a first portion of the outer surface of the needle, and wherein the gripping device is configured to grip a second portion of the outer surface of the needle not covered by 28. The device as defined in claim 25, wherein the rotating mechanism is configured for cordless operation.

29. The device as defined in claim 25, further comprising a sleeve configured to extend over at least a portion of the needle when the needle is gripped by the gripping device.

30. A device for intraosseous delivery of solutions, comprising:
- a housing that receives a solution cartridge having a penetrable seal on one end thereof, the solution cartridge holding a solution therein;
- a gripping device having an open position to receive a needle and having a closed position to grip the needle, the needle having a hollow bore extending therethrough from a proximal end to a distal end thereof, the gripping device holding the needle with the proximal end of the needle in the solution and with the distal end of the needle exposed for engagement with a material to be drilled;
- a rotating mechanism that rotates the gripping device to rotate the needle; and
- a dispensing mechanism that applies pressure to the solution within the solution cartridge to force the solution from the solution cartridge through the hollow bore of the needle to eject the solution from the distal end of the needle,
- wherein the solution cartridge has a first axis and wherein the needle rotates about a second axis, the second axis being at an angle with respect to the first axis.

31. The device as defined in claim 30, wherein the gripping device comprises a collet mechanism.

32. The device as defined in claim 30, wherein the gripping device comprises a chucking mechanism that grips the needle in a region closer to the proximal end of the needle than to the distal end of the needle.

33. The device as defined in claim 32, wherein the chucking mechanism comprises a radially expandable collet that expands to receive the needle and that contracts to hold the needle.

34. The device as defined in claim 33, wherein the radially expandable collet is responsive to a force to contract about the needle.

35. The device as defined in claim 33, further comprising a biasing member to bias the collet to a compressed position to contract about the needle.

36. The device as defined in claim 30, wherein the gripping device comprises a plurality of lever arms.

37. The device as defined in claim 30, wherein the gripping device is configured to receive a standard type needle.

38. The device as defined in claim 37, wherein the standard type needle comprises a hub covering a first portion of the outer surface of the needle, and wherein the gripping device is configured to grip a second portion of the outer surface of the needle not covered by the hub.

39. The device as defined in claim 30, wherein the rotating mechanism is configured for cordless operation.

40. The device as defined in claim 30, further comprising a sleeve configured to extend over at least a portion of the needle when the needle is gripped by the gripping device.

41. A device for intraosseous delivery of solutions, comprising:
- a housing that receives a solution cartridge having a penetrable seal on one end thereof, the solution cartridge holding a solution therein;
- a gripping device having an open position to receive a rotatable tool and having a closed position to grip the tool, the tool having a hollow bore extending therethrough from a proximal end to a distal end thereof, the gripping device holding the tool with the proximal end of the tool in the solution and with the distal end of the tool exposed for engagement with a material;
- a rotating mechanism that rotates the gripping device to rotate the tool; and
- a dispensing mechanism that applies pressure to the solution within the solution cartridge to force the solution from the solution cartridge through the hollow bore of the tool to eject the solution from the distal end of the tool.

42. The device as defined in claim 41, wherein the tool comprises one of a needle, a file, a drill bit or a burr.

43. A method for preparing a device for intraosseous delivery of solutions, comprising:
- positioning a solution cartridge in a housing, the solution cartridge having a penetrable seal on one end thereof, the solution cartridge holding a solution therein;
- opening a gripping device to an open position to receive a needle, the needle having a hollow bore extending therethrough from a proximal end to a distal end thereof;
- inserting the proximal end of the needle through the gripping device to position the proximal end of the needle in the solution;
- closing the gripping device to a closed position to grip the needle, the gripping device holding the needle with the proximal end in the solution and with the distal end of the needle exposed for engagement with a material to be drilled; and
- applying a rotational force to the gripping device to rotate the needle held by the gripping device.

44. The method as defined in claim 43, wherein the gripping device comprises a collet mechanism.

45. The method as defined in claim 43, wherein the gripping device comprises a chucking mechanism that grips the needle in a region closer to the proximal end of the needle than to the distal end of the needle.

46. The method as defined in claim 43, wherein the needle is a standard type needle having a hub covering a first portion of the outer surface of the needle, and the method further comprises gripping a second portion of the outer surface of the needle not covered by the hub.

47. A method for preparing a device for intraosseous delivery of solutions, comprising:
- positioning a solution cartridge in a housing, the solution cartridge having a penetrable seal on one end thereof, the solution cartridge holding a solution therein;
- opening a gripping device to an open position to receive a needle, the needle having a hollow bore extending therethrough from a proximal end to a distal end thereof, wherein the gripping device comprises a chucking mechanism that grips the needle in a region closer to the proximal end of the needle than to the distal end of the needle;
- inserting the proximal end of the needle through the gripping device to position the proximal end of the needle in the solution;
- closing the gripping device to a closed position to grip the needle, the gripping device holding the needle with the proximal end in the solution and with the distal end of the needle exposed for engagement with a material to be drilled;
- applying a rotational force to the gripping device to rotate the needle held by the gripping device;
- radially expanding a collet in the chucking mechanism to receive the needle; and
- radially contracting the collet to hold the needle.

48. The method as defined in claim 47, further comprising applying a force to the collet to contract the collet about the needle.

49. The method as defined in claim 48, further comprising biasing the collet to a compressed position to contract the collet about the needle.

50. A method for preparing a device for intraosseous delivery of solutions, comprising:
  positioning a solution cartridge in a housing, the solution cartridge having a penetrable seal on one end thereof, the solution cartridge holding a solution therein;
  opening a gripping device to an open position to receive a needle, the needle having a hollow bore extending therethrough from a proximal end to a distal end thereof;
  inserting the proximal end of the needle through the gripping device to position the proximal end of the needle in the solution;
  closing the gripping device to a closed position to grip the needle, the gripping device holding the needle with the proximal end in the solution and with the distal end of the needle exposed for engagement with a material to be drilled; and
  applying a rotational force to the gripping device to rotate the needle held by the gripping device;
  positioning the solution cartridge in the housing with the solution cartridge oriented along a first axis; and
  rotating the needle about a second axis, the second axis being at an angle with respect to the first axis.

51. The device as defined in claim 50, wherein the gripping device comprises a collet mechanism.

52. The method as defined in claim 50, wherein the gripping device comprises a collet mechanism.

53. The method as defined in claim 50, wherein the gripping device comprises a chucking mechanism that grips the needle in a region closer to the proximal end of the needle than to the distal end of the needle.

54. The method as defined in claim 53, further comprising:
  radially expanding a collet in the chucking mechanism to receive the needle; and
  radially contracting the collet to hold the needle.

55. The method as defined in claim 54, further comprising applying a force to the collet to contract the collet about the needle.

56. The method as defined in claim 55, further comprising biasing the collet to a compressed position to contract the collet about the needle.

57. The method as defined in claim 50, wherein the needle is a standard type needle having a hub covering a first portion of the outer surface of the needle, and the method further comprises gripping a second portion of the outer surface of the needle not covered by the hub.

* * * * *

UNITED STATES PATENT AND TRADEMARK OFFICE
CERTIFICATE OF CORRECTION

PATENT NO.      : 7,588,559 B2  
APPLICATION NO. : 11/089446  
DATED           : September 15, 2009  
INVENTOR(S)     : Aravena et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 715 days.

Signed and Sealed this

Twenty-first Day of September, 2010

David J. Kappos  
*Director of the United States Patent and Trademark Office*

UNITED STATES PATENT AND TRADEMARK OFFICE
CERTIFICATE OF CORRECTION

| | | |
|---|---|---|
| PATENT NO. | : 7,588,559 B2 | Page 1 of 1 |
| APPLICATION NO. | : 11/089446 | |
| DATED | : September 15, 2009 | |
| INVENTOR(S) | : Ines M. Aravena et al. | |

It is certified that error appears in the above-identified patent and that said Letters Patent is hereby corrected as shown below:

In the Specification:

Column 6, line 67, "a chucking a quick" should read --a chucking, a quick--.

Column 16, line 46, "1 75b" should read --175b--.

Column 16, line 47, "1 75b" should read --175b--.

In the Claims:

Claim 14, column 31, line 56, "openposition" should read --open position--.

Claim 27, column 32, line 67, "by" should read --by the hub.--.

Signed and Sealed this
Twelfth Day of July, 2011

David J. Kappos
*Director of the United States Patent and Trademark Office*